(12) United States Patent
Yang et al.

(10) Patent No.: US 10,865,388 B2
(45) Date of Patent: Dec. 15, 2020

(54) METHOD FOR IDENTIFYING ANTI-CANCER AGENTS USING AN IN VITRO CELL CULTURE SYSTEM THAT MAINTAINS CANCER CELL STEMNESS

(71) Applicant: National Taiwan University, Taipei (TW)

(72) Inventors: Pan-Chyr Yang, Taipei (TW); Huei-Wen Chen, Taipei (TW); Wan-Jiun Chen, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 15/513,804

(22) PCT Filed: Sep. 24, 2014

(86) PCT No.: PCT/US2014/057173
§ 371 (c)(1),
(2) Date: Mar. 23, 2017

(87) PCT Pub. No.: WO2016/048299
PCT Pub. Date: Mar. 31, 2016

(65) Prior Publication Data
US 2018/0230435 A1    Aug. 16, 2018

(51) Int. Cl.
| G01N 33/50 | (2006.01) |
| C12N 5/095 | (2010.01) |
| C12N 5/09 | (2010.01) |
| G01N 33/574 | (2006.01) |

(52) U.S. Cl.
CPC .......... *C12N 5/0695* (2013.01); *C12N 5/0693* (2013.01); *G01N 33/5011* (2013.01); *G01N 33/5017* (2013.01); *G01N 33/574* (2013.01); *G01N 33/57492* (2013.01); *G01N 33/57496* (2013.01); *C12N 2501/605* (2013.01); *C12N 2502/30* (2013.01); *G01N 2333/475* (2013.01); *G01N 2333/4706* (2013.01); *G01N 2333/4753* (2013.01); *G01N 2333/52* (2013.01); *G01N 2333/71* (2013.01); *G01N 2333/715* (2013.01); *G01N 2333/7158* (2013.01); *G01N 2800/52* (2013.01)

(58) Field of Classification Search
CPC .................. G01N 33/5011; G01N 33/574
See application file for complete search history.

(56) References Cited

FOREIGN PATENT DOCUMENTS

| WO | WO 2008/068481 A1 | 6/2008 |
| WO | WO 2012/010105 A1 | 1/2012 |
| WO | WO 2012/093173 A1 | 7/2012 |
| WO | WO 2013/126993 A1 | 9/2013 |

OTHER PUBLICATIONS

Chen et al., Cancer-associated fibroblasts regulate the plasticity of lung cancer stemness via paracrine signalling. Nat Commun. Mar. 25, 2014;5:3472. doi: 10.1038/ncomms4472.
Dolznig et al., Modeling colon adenocarcinomas in vitro a 3D co-culture system induces cancer-relevant pathways upon tumor cell and stromal fibroblast interaction. Am J Pathol. Jul. 2011;179(1):487-501. doi:10.1016/j.ajpath.2011.03.015. Epub Apr. 30, 2011.
Franco et al., Cancer associated fibroblasts in cancer pathogenesis. Semin Cell Dev Biol. Feb. 2010;21(1):33-9. doi:10.1016/j.semcdb. 2009.10.010. Epub Nov. 5, 2009.
Navab et al., Prognostic gene-expression signature of carcinoma-associated fibroblasts in non-small cell lung cancer. Proc Natl Acad Sci U S A. Apr. 26, 2011;108(17):7160-5. doi: 10.1073/pnas. 1014506108. Epub Apr. 7, 2011.
Shintani, Yasishi, et al.; "Abstract 54: Cancer-associated fibroblasts induce epithelial-mesenchymal-transition and stemness in non-small-cell lung cancer"; Molecular and Cellular Biology; Published Apr. 2012; pp. 5.
Shintani, Yasushi, et al.; "Pulmonary Fibroblasts Induce Epithelial Mesenchymal Transition and Some Characteristics of Stem Cells in Non-Small Cell Lung Cancer"; Society of Thoracic Surgeons published by Elsevier Inc; Published Mar. 28, 2013; pp. 10.

*Primary Examiner* — Prema M Mertz
(74) *Attorney, Agent, or Firm* — McDermott Will & Emery LLP

(57) ABSTRACT

An in vitro co-culture system comprising cancer-associated fibroblasts (CAFs) and cancer cells for producing and maintaining cancer stem cells and uses thereof for identifying agents capable of reducing cancer cell stemness. Also disclosed herein are a paracrine network through which CAFs facilitate production and/or maintenance of cancer stem cells and the use of components of such a paracrine network for prognosis purposes and for identifying cancer patients who are likely to respond to certain treatment.

10 Claims, 54 Drawing Sheets

Specification includes a Sequence Listing.

e

Subcutaneous xenograft | Meta Lung -tumor

H&E

Nanog

Oct3/4

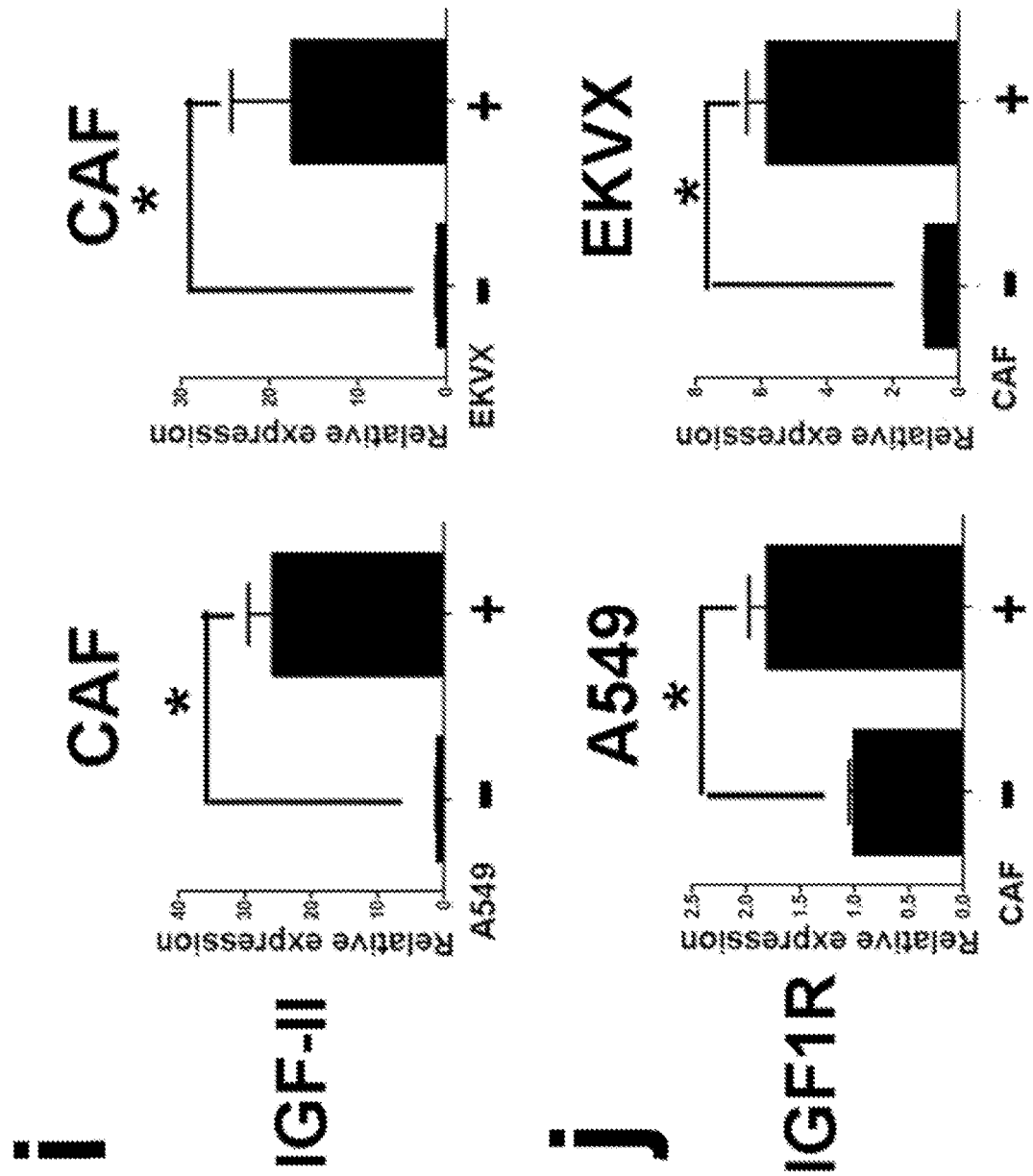

B.

SEQUENCE LISTING

<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
ttcagccaaa cgaccatctg                                       20

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
cacactgccc ctctcacaca t                                     21

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide -continued

<400> SEQUENCE: 3
caccagtccc aaaggcaaac                                              20

<210> SEQ ID NO 4
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 4
ggcggcattt gggataca                                                18

<210> SEQ ID NO 5
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 5
tacaaagggc catcgttcat c                                            21

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 6
gcagaagctg ggtgtcatag gt                                           22

<210> SEQ ID NO 7
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 7
tccttcaaac gtgctgacat ct                                           22

<210> SEQ ID NO 8
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 8
gccaccttgc aggttcga                                                18

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 9
tcctggctaa cgacaaatac ga                                           22

```
<210> SEQ ID NO 10
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 10
tttcacgtct tggtgccttt t                                          21

<210> SEQ ID NO 11
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 11
tctctagttc cccacctcaa tcc                                        23

<210> SEQ ID NO 12
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 12
ccaacatgac ttgcgactac gt                                         22

<210> SEQ ID NO 13
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 13
caaatgtcag ccctggagtt c                                          21

<210> SEQ ID NO 14
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 14
gctaaaatgc tggcacccta aa                                         22

<210> SEQ ID NO 15
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 15
atgcgggact ggctcaag                                              18

<210> SEQ ID NO 16
<211> LENGTH: 19
<212> TYPE: DNA
<213> ORGANISM: Artificial Sequence
<220> FEATURE:
<223> OTHER INFORMATION: Synthetic Oligonucleotide
```

```
<400> SEQUENCE: 16
gcccacctgg acacaacac                                                    19

<210> SEQ ID NO 17
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 17
catccgcaaa gtgactgaag ag                                                22

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
ctggaacggt gaaggtgaca                                                   20

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19
gaaccacact cggaccacat c                                                 21

<210> SEQ ID NO 20
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 20
cccatttccc tcgtttttct t                                                 21

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
gccttctgcg tcacaccatt                                                   20

<210> SEQ ID NO 22
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 22
tctgtcatgg tggaaagatg ga                                                22
```

```
<210> SEQ ID NO 23
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 23
tccggacacg aggaatcag                                               19

<210> SEQ ID NO 24
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 24
cacggaggat gcggtctta                                               19

<210> SEQ ID NO 25
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 25
tggaacatcg tcgagcaatt t                                            21

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 26
cagacccacc agctgacttc tt                                           22

<210> SEQ ID NO 27
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 27
gggccacgtc aggttgac                                                18

<210> SEQ ID NO 28
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 28
ccctcacaat tgcacatgtc a                                            21

<210> SEQ ID NO 29
<211> LENGTH: 19
<212> TYPE: DNA
<213> ORGANISM: Artificial Sequence
<220> FEATURE:
<223> OTHER INFORMATION: Synthetic Oligonucleotide
```

```
<400> SEQUENCE: 29
ttgtcaccca aggccatgt                                           19

<210> SEQ ID NO 30
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 30
cctggtcgaa actcatcaga ttc                                      23

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
ccgatagctc gaaggcaaaa                                          20

<210> SEQ ID NO 32
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 32
gatatccggg acaccagttc ag                                       22

<210> SEQ ID NO 33
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 33
cagtcagaag gttgttgtcc tcat                                     24

<210> SEQ ID NO 34
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 34
ggaccgggtt gctgaaaag                                           19

<210> SEQ ID NO 35
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 35
ctgtactgaa ctccgttgtg atagc                                    25
```

```
<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
cggccacatt gtgaactttg                                              20
```

METHOD FOR IDENTIFYING ANTI-CANCER AGENTS USING AN IN VITRO CELL CULTURE SYSTEM THAT MAINTAINS CANCER CELL STEMNESS

CROSS-REFERENCE TO RELATED APPLICATIONS

This application is a national stage filing under 35 U.S.C. § 371 of international Application No. PCT/US2014/057173, filed Sep. 24, 2014, the entire content of which is herein incorporated by reference.

BACKGROUND OF THE INVENTION

Lung cancer is the most common fatal malignancy worldwide. Siegel et al., *CA Cancer J Clin* 62, 10-29 (2012). Due to the success of driver gene identification and specific targeted therapy, many lung cancer patients show good initial responses. However, most patients eventually develop drug resistance and relapse within 1 year. Kobayashi, et al. *N Engl J Med* 352, 786-792 (2005); and Sequist, et al., *J Clin Oncol* 25, 587-595 (2007). Current anticancer strategies indicate that most traditional interventions are aimed at cancer cells of an unspecified type, although solid tumors represent an organized, heterogeneous cell population. Egeblad, et al., *Dev Cell* 18, 884-901 (2010). The complicated cell-cell interactions that form the tumor microenvironment (or niche) involve a small population of cells termed cancer stem/initiating cells (CSCs). These cells are believed to represent the cause of most malignant tumors, and both CSCs and the tumor niche play major roles in cancer recurrence, metastasis and drug resistance. Eramo, et al., *Oncogene* 29, 4625-4635 (2010); Joyce, et al., *Nat Rev Cancer* 9, 239-252 (2009); Reya, et al., *Nature* 414, 105-111 (2001); and McCarthy, *Nat Rev Cancer* 12, 152-153 (2012).

The CSC theory is based on the presence of a subpopulation of tumorigenic stem-like cells with true multipotency and asymmetric division ability, which enable these cells to self-renew, differentiate into specialized cell types and develop into cancer. Reya et al., 2001; and Wang, et al., *Trends Cell Biol* 15, 494-501 (2005). The phenotype of "cancer stemness" may be the driving force behind carcinogenesis (Eramo et al., 2010), and CSCs may contribute to chemo- or radio-resistance and metastasis (Malanchi, et al. *Nature* 481, 85-89 (2012); Pardal, et al., *Nat Rev Cancer* 3, 895-902 (2003); and Clevers, et al., *Nat Med* 17, 313-319 (2011)). Increasing evidence shows that CSCs are not only present in leukemia but also in various solid tumors, including lung cancer. Zhang, et al. *Cell* 148, 259-272 (2012); Kim, et al. *Cell* 121, 823-835 (2005); and Eramo, et al. *Cell Death Differ* 15, 504-514 (2008). Although lung CSCs can be isolated from side populations (SPs) through specific markers such as CD133 and aldehyde dehydrogenase (ALDH) (Ho, et al., *Cancer Res* 67, 4827-4833 (2007); Vermeulen, et al. *Proc Natl Acad Sci USA* 105, 13427-13432 (2008); and Sullivan, et al. *Cancer Res* 70, 9937-9948 (2010)), it remains difficult to maintain the stemness characteristics of CSCs in vitro for detailed studies (Ho et al., 2007; and Bertolini et al., 2009). To maintain a quiescent state, most stem cells (e.g., embryonic, induced pluripotent stem cells and even lung stem cells) depend on direct contact in the microenvironment or the presence of "feeder cells". Fuchs et al., 2004; Sneddon et al., 2007; Ling, et al. *Proc Natl Acad Sci USA* 103, 9530-9535 (2006); Takahashi, et al., *Cell* 126, 663-676 (2006); Thomson et al., 1998; and Williams, et al. *Nature* 336, 684-687 (1988). Interestingly, recent discoveries have also indicated that the tumor microenvironment may promote and enhance tumorigenicity under inflammatory or transforming growth factor-beta (TGF-β) signals. Chaffer, et al. *Cell* 154, 61-74 (2013); Schwitalla et al., 2013; and Ghajar, et al. *Nat Cell Biol* 15, 807-817 (2013). In human lung cancer, the tumor microenvironment contains an abundance of cancer-associated fibroblasts (CAFs). Kalluri et al., 2006. CAFs differ morphologically and functionally from normal fibroblasts, and they are activated and responsive to cross-talk with cancer cells during carcinogenesis. Kojima, et al. *Proc Natl Acad Sci USA* 107, 20009-20014 (2010); and Bremnes, et al. *J Thorac Oncol* 6, 209-217 (2011).

SUMMARY OF THE INVENTION

In the present disclosure, cancer-associated fibroblast (CAF) feeders from clinical lung cancer patients were demonstrated as being important to maintain and enrich the population of cancer stem cells (CSCs) as a sustainable sphere-forming primary lung CSC culture. This CSC/CAF co-culture system would be useful for subsequent investigations into how the tumor microenvironment maintains cancer stemness, the signaling involved in cancer cell differentiation and even anti-CSC drug development. Most importantly, the findings disclosed herein revealed that CSC growth was regulated in a paracrine manner by CAFs through the IGF-II/IGF1R/Nanog pathway. In particular, the inhibition of IGF1R signaling using a specific antibody or inhibitors could suppress cancer stemness and tumor growth. Lastly, such results were in a cohort of 80 stage I NSCLC patients and it was determined that the pathophysiological significance of IGF-II/IGF1R/Nanog paracrine signaling on lung cancer progression. Together, these findings show that tumor microenvironment CAFs play an important role in maintaining cancer stemness.

Accordingly, provided herein are methods for producing or maintaining cancer stem cells (CSCs) in vitro, an in vitro co-culturing system, and uses thereof for identifying drug candidates that are capable of reducing cancer cell stemness, methods for assessing the survival rate of a cancer patient, and a kit for performing such a method.

In one aspect, the present disclosure features an in vitro co-culture system, comprising cancer associated fibroblasts (CAFs) and a population of cancer cells, wherein the CAFs are CD90$^+$, and wherein the CAFs maintain stemness of the cancer cells in the co-culture system. For example, the in vitro co-culture system may comprise cancer stem cells, which can be Oct3/4$^+$ and Nanog$^+$. In some embodiments, the CAFs are obtained from a cancer patient, such as a lung cancer patient, a breast cancer patient, a kidney cancer patient, a prostate cancer patient, an ovary cancer patient, a skin cancer patient, a cervical cancer patient, a colon cancer patient, a liver cancer patient, a melanoma patient, an oral cancer patient, or a pancreatic cancer patient. In one example, the cancer patient is a non-small cell lung cancer patient.

Alternatively or in addition, the population of cancer cells include lune cancer cells, breast cancer cells, kidney cancer cells, prostate cancer cells, ovary cancer cells, skin cancer cells, cervical cancer cells, colon cancer cells, liver cancer cells, melanoma cells, oral cancer cells, or pancreatic cancer cells. In one example, the cancer cells are non-small cell lung cancer cells.

In another aspect, the present disclosure provides a method for producing or maintaining cancer stem cells (CSC) in vitro, the method comprising: (i) providing a population of cancer cells; (ii) providing cancer-associated fibroblasts (CAFs), which are CD90$^+$; and (iii) co-culturing the population of cancer cells with the CAFs to produce or maintain cancer stem cells in the culture, which can be Oct3/4$^+$ and Nanog$^+$ cells.

The population of cancer cells may be from an established cancer cell line. Alternatively, the population of cancer cells may be primary cancer cells obtained from a cancer patient. The population of cancer cells may include, but are not limited to, lung cancer cells, breast cancer cells, kidney cancer cells, prostate cancer cells, ovary cancer cells, skin cancer cells, cervical cancer cells, colon cancer cells, liver cancer cells, melanoma cells, oral cancer cells, or pancreatic cancer cells. In one example, the population of cancer cells include non-small cell lung cancer cells.

The CAFs can be obtained from a cancer patient, including, but not limited to, a lung cancer patient, a breast cancer patient, a kidney cancer patient, a prostate cancer patient, an ovary cancer patient, a skin cancer patient, a cervical cancer patient, a colon cancer patient, a liver cancer patient, a melanoma patient, an oral cancer patient, or a pancreatic cancer patient. In one example, the CAFs are obtained from a non-small cell lung cancer patient. Alternatively, the CAFs can be from an established CAF cell line.

Further, the present disclosure provides a method for identifying an anti-cancer drug, comprising: (i) co-culturing cancer cells and cancer-associated fibroblasts (CAFs) in the presence of a drug candidate, wherein the CAFs are CD90$^+$; (ii) determining the level of cancer cell stemness in the co-culture, and (iii) identifying the drug candidate as an anti-cancer drug, if the level of cancer stemness in the co-culture is decreased as compared to that of a co-culture of cancer cells and CAFs in the absence of the drug candidate.

The cancer cells may be from an established cancer cell line. Alternatively, the cancer cells are primary cancer cells obtained from a cancer patient. In some examples, the cancer cells are lung cancer cells, breast cancer cells, kidney cancer cells, prostate cancer cells, ovary cancer cells, skin cancer cells, cervical cancer cells, colon cancer cells, liver cancer cells, melanoma cells, oral cancer cells, or pancreatic cancer cells. In one example, the cancer cells are non-small cell lung cancer cells.

The CAFs can be obtained from a cancer patient, e.g., a lung cancer patient, a breast cancer patient, a kidney cancer patient, a prostate cancer patient, an ovary cancer patient, a skin cancer patient, a cervical cancer patient, a colon cancer patient, a liver cancer patient, a melanoma patient, an oral cancer patient, or a pancreatic cancer patient. In one example, the cancer patient is a non-small cell lung cancer patient. Alternatively, the CAFs can be an established CAF cell line.

In any of the methods described herein, the level of cancer cell stemness is represented by the number of cancer stem cells (CSC) in the co-culture, wherein the CSCs are Oct3/4$^+$ and Nanog$^+$. Alternatively or in addition, the level of cancer cell stemness is represented by the drug resistance of the cancer cells in the co-culture. In other embodiments, the level of cancer cell stemness is represented by the level of one or more of IGF-II, HGF, LIF, and SDF1 expressed in the CAFs, the level of one or more of IGF1R, IGF2R, LIFR, CXCR4, and Nanog expressed in the cancer cells, or both. In another example, the level of cancer cell stemness is represented by the ratio of CSCs to total cells in a cancer cell colony formed in the co-culture.

Moreover, the present disclosure provides a method for assessing the survival rate of a cancer patient, the method comprising: (i) providing a tumor tissue of a cancer patient; (ii) measuring the level of IGF-II expressed in cancer-associated fibroblasts (CAFs) in the tumor tissue; (iii) measuring the level of IGF1R, Nanog, or both expressed in cancer cells in the tumor tissue; and (iv) assessing the survival rate of the cancer patient based on the level of IGF-II expressed in CAFs and the level of IGF1R, Nanog, or both expressed in the cancer cells. If the level of IGF-II and the level of IGF1R, Nanog, or both are higher than predetermined values, it indicates that the patient has a poor survival rate. If the level of IGF-II and the level of IGF1R, Nanog or both are lower than the predetermined values, it indicates that the patient has a good survival rate.

In some examples, the level of IGF-II and the level of IGF1R, Nanog, or both are measured by Immunohistochemistry. The survival rate can be overall survival rate or relapse-free survival rate.

The cancer patient may have lung cancer, breast cancer, kidney cancer, prostate cancer, ovary cancer, skin cancer, cervical cancer, colon cancer, liver cancer, melanoma, oral cancer, or pancreatic cancer. In one example, the patient has non-small cell lung cancer.

In yet another aspect, the present disclosure provides a kit for assessing cancer cell stemness, comprising: (i) a first agent for detecting IGF-II, HGF, LIF, SDF1; DLL1, Jagged1, IBP5, thrombospondin1, PLAU, or Decorin, and (ii) a second agent for detecting IGF1R, IGF2R, LIFR, CXCR4, HGFR, Notch3, or Nanog. The first agent, the second agent, or both may be antibodies. In some embodiments, the first agent is an antibody specific to IGF-II. Alternatively or in addition, the second agent is an antibody specific to IGF1R or Nanog.

In one example, the second agent is an antibody specific to IGF1R. The kit may further comprise a third agent for detecting Nanog, e.g., an anti-Nanog antibody.

Further, the present disclosure provides a method for treating lung cancer, comprising administering to a subject in need thereof an effective amount of an anti-lung cancer drug, wherein the subject is a lung cancer patient having an elevated level of IGF-II in cancer-associated fibroblasts and an elevated level of IGF1R or Nanog in cancer stem cells. The anti-lung cancer drug is a drug that interferes with the IGF-II/IGF1R signaling pathway. In some embodiments, the drug is an antibody that specifically binds IGF-II or IGF1R.

Also within the scope of the present disclosure is an image-based high content assay for assessing stemness of cancer cells, the assay comprising: (i) providing a sample comprising both cancer cells and cancer-associated fibroblasts; (ii) staining the sample with a first agent for detecting Nanog, wherein the first agent is conjugated with a first label directly or indirectly; (iii) staining the sample with a second agent for detecting CD90, wherein the second agent is conjugated with a second label directly or indirectly, the second label being different from the first label; (iv) imaging the sample stained with the first and second agents; and (v) determining stemness of the cancer cells in the sample based on the signals released from the first and second labels. The first label, the second label, or both may be fluorescent dyes. The assay may further comprise staining the sample with a third agent for detecting nuclei, which may be DAPI. In some examples, the first agent, the second agent, or both are antibodies.

In some embodiments, step (ii) may be performed by reacting the sample with the first agent, which is an antibody specific to Nanog, and conjugating the antibody that is bound to the sample with a secondary antibody labeled with TRITC. In some examples, the second agent may be an anti-CD90 antibody labeled with FITC.

In some embodiments, step (v) may be performed by identifying cancer cell colonies and assessing the stemness of one or more cancer cell colonies, which is represented by the ratio of the number of Nanog-positive cells to the number of total cells in each cancer cell colony.

In any of the image-based high content assays described herein, the sample is a co-culture of the cancer cells and cancer-associated fibroblasts. The co-culture may further comprise a candidate compound and the assay may further comprise determining whether the candidate compound is an anti-cancer drug, wherein a reduced level of cancer cell stemness in the presence of the candidate compound as relative to that in the absence of the candidate compound indicates that the candidate compound is an anti-cancer drug.

The cancer cells in the sample can be lung cancer cells, breast cancer cells, kidney cancer cells, prostate cancer cells, ovary cancer cells, skin cancer cells, cervical cancer cells, colon cancer cells, liver cancer cells, melanoma cells, oral cancer cells, or pancreatic cancer cells. In one example, the cancer cells are non-small cell lung cancer cells.

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

Figure 1:
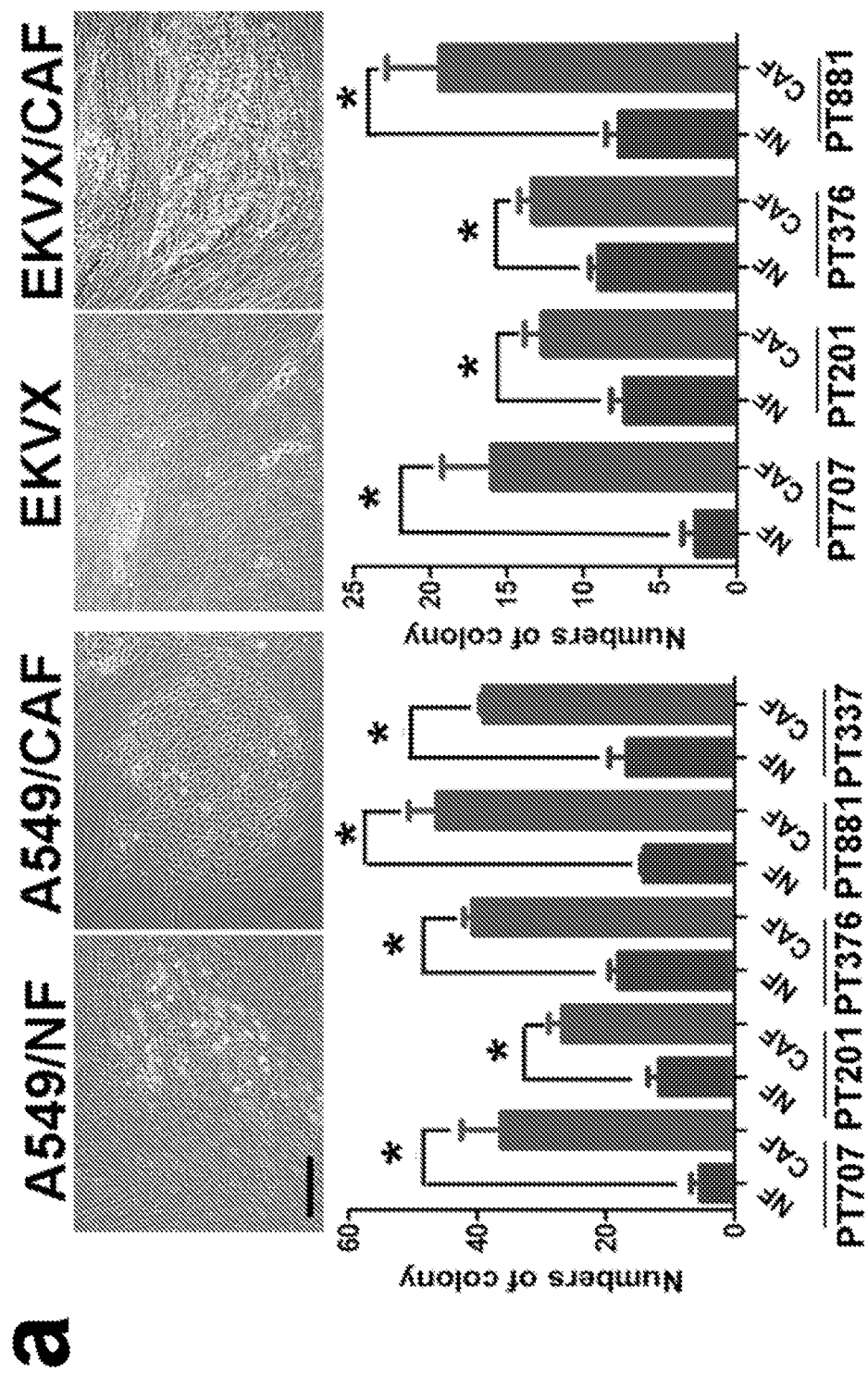
FIG. 1 include diagrams showing the role of CAFs or NFs as feeders to promote tumorigenicity and up-regulate stemness markers in lung cancer cells. (a): photo and charts showing the colony-formation ability of A549 and EKVX cell lines co-cultured with paired CAFs or NFs from different lung cancer patients (N=4~5 patients, PT707, 201, 376, 881 and 337). Scale bar, 100 μm. (b): charts showing RT Q-PCR analysis of the stem cell markers Oct3/4 and Nanog in A549 and EKVX cells cultured with or without NFs and CAFs (N=3~4 patients, PT707, 201, 376 and 881) (c): a photo showing immunofluorescent staining for Nanog in A549 and EKVX cells cultured with or without CAFs. The nuclei were stained with DAPI. Scale bar, 100 μm. (d): a photo showing a PKH26 retention assay with A549 and EKVX cells. The cells were pre-stained with the PKH26 red fluorescent dye, and the cells were cultured with or without CAFs Scale bar, 100 μm. (e): photos showing primary cultured lung cancer cell lines (CL141, CL83, CL25 and CL152), which were co-cultured with CAFs, and the cancer cell lines that formed spheroid-like colonies were examined. Scale bar, 200 μm. (f): charts showing RT Q-PCR analysis of the stem cell marker Nanog in CL141, CL83, CL25 and CL152 cells cultured with or without CAFs (N=3). (g): photo and charts showing lung CSCs (CLS1) derived from lung cancer tissue formed spheres after culturing with CAFs for 2-10 days (upper panel). RT Q-PCR analysis of Oct3/4, Sox2 and Nanog expression in CLS1 cells. RNA was extracted from the CLS1 spheres cultured with CAFs (CLS1/CAF co-culture) or CLS1 cells cultured without CAFs after passage 4 (CLS1 p4). An embryonic stem cell line, H9, was used as the positive control, and CAFs or NFs were used as the feeder cell controls (lower panel) (N=3). (h): photos showing immunofluorescence characterization of CLS1 cells and CAFs; the CLS1 cells expressed Oct3/4 and Nanog, whereas CAFs expressed CD90. The nuclei were stained with DAPI. Scale bar, 100 μm. The data represent the mean±S.D. and were tested for significance using two-way ANOVA with Tukey's post hoc corrections (a) or the Student's t-test (b-g); *P<0.05. The data are representative of at least three independent biological experiments, with three or more replicates in each experiment. (I) diagram showing surface markers of CAFs.
Figure 1:
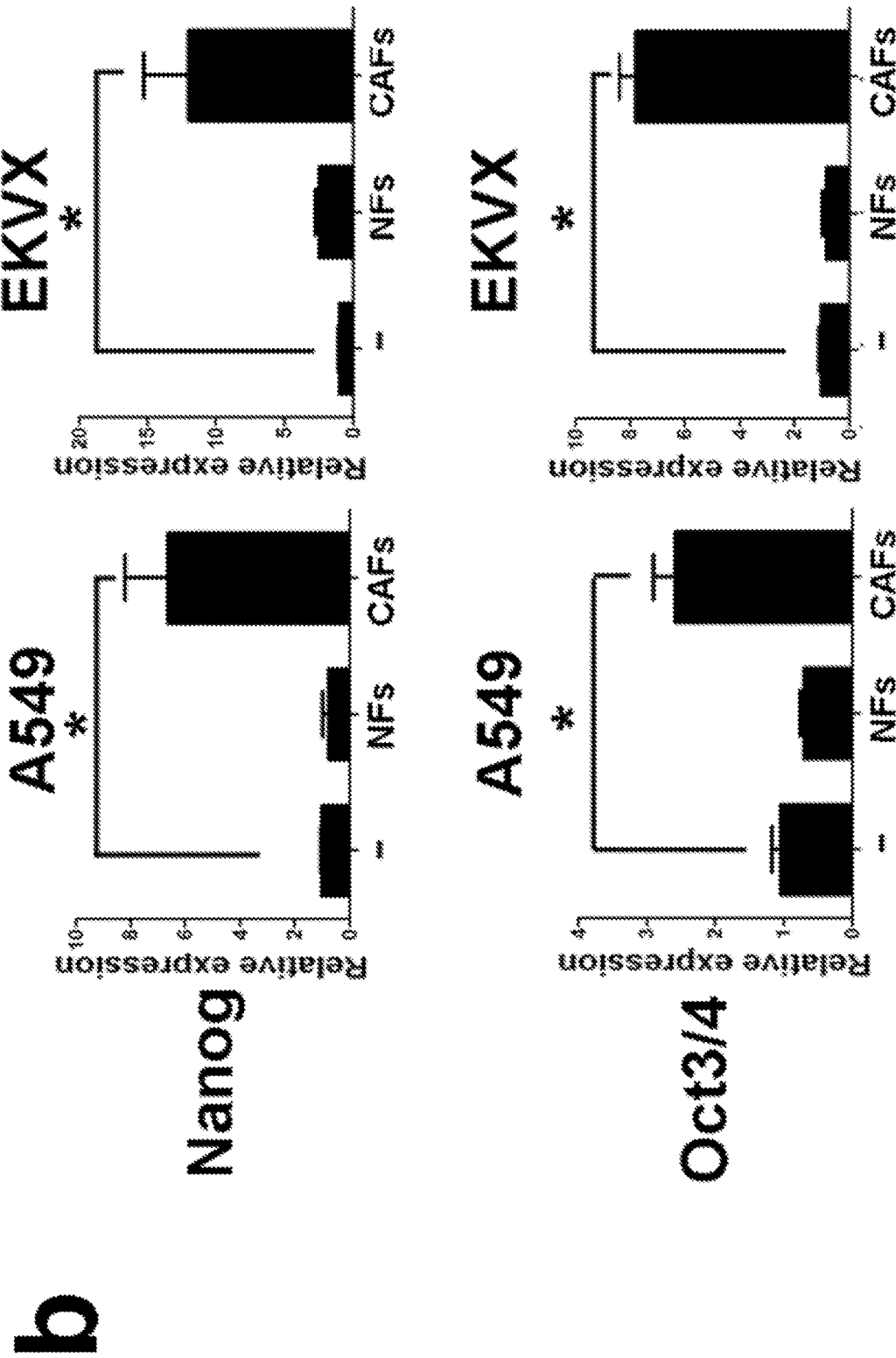
Figure 1:
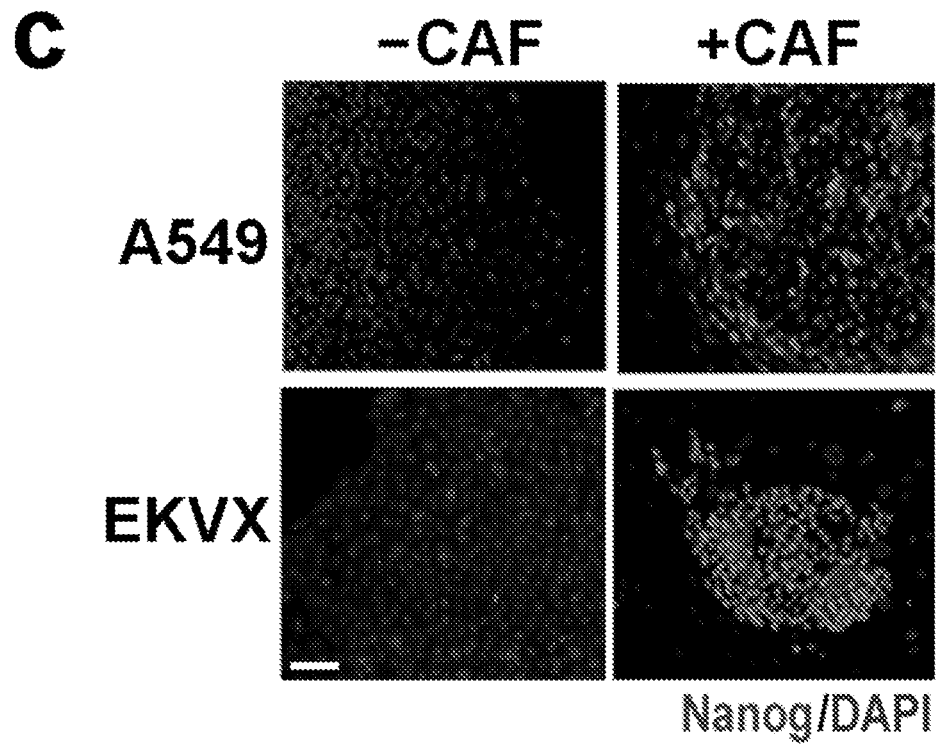
Figure 1:
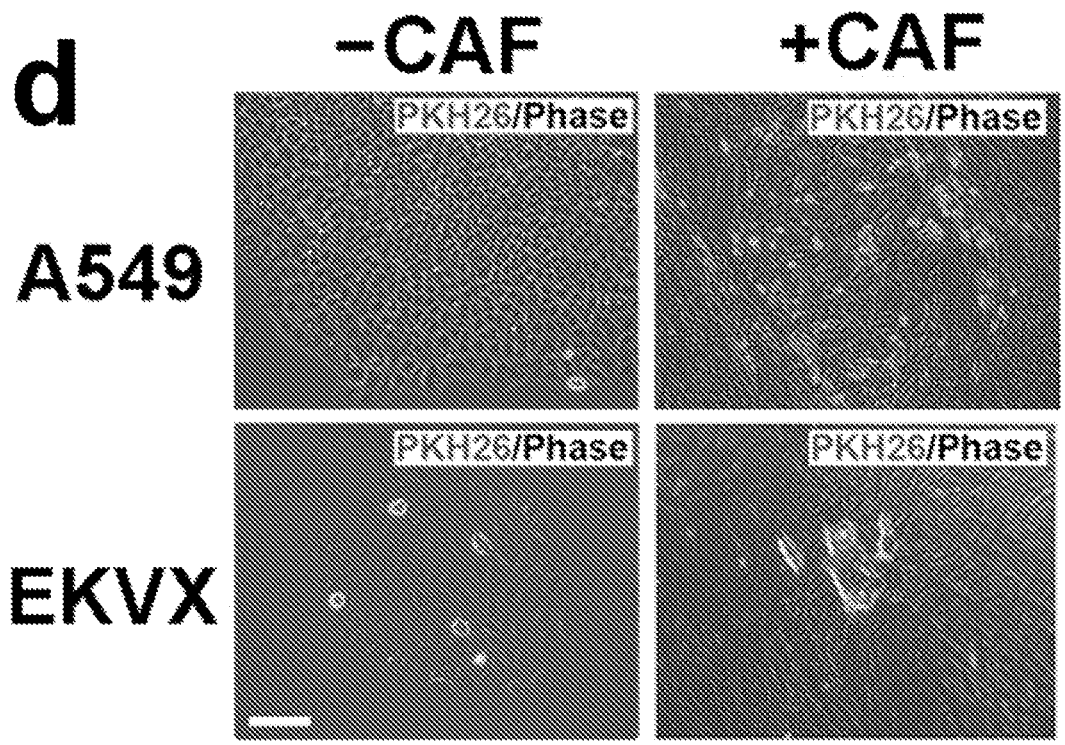
Figure 1:
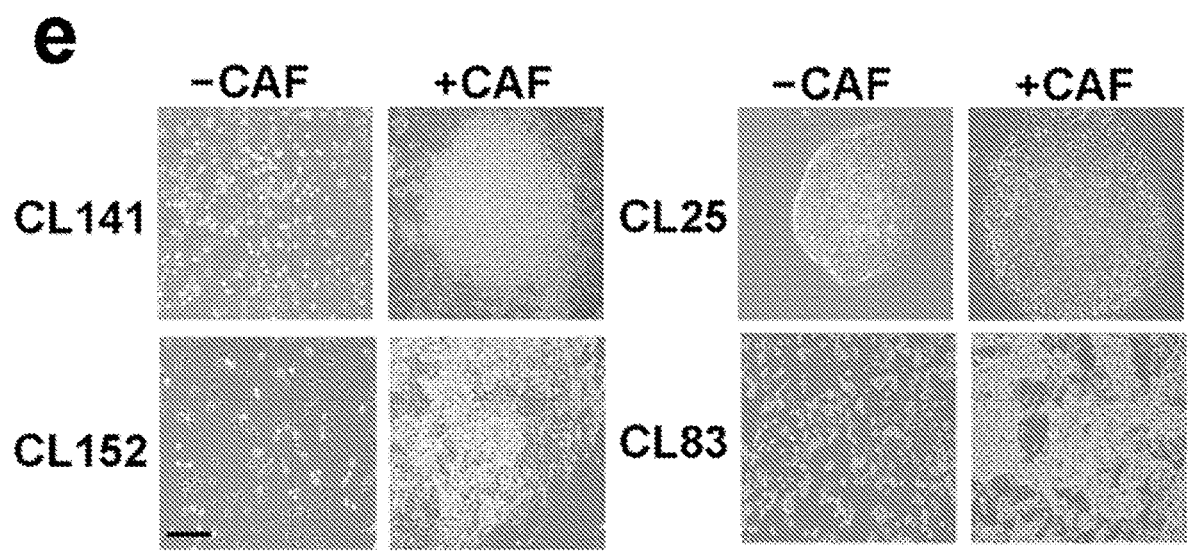
Figure 1:
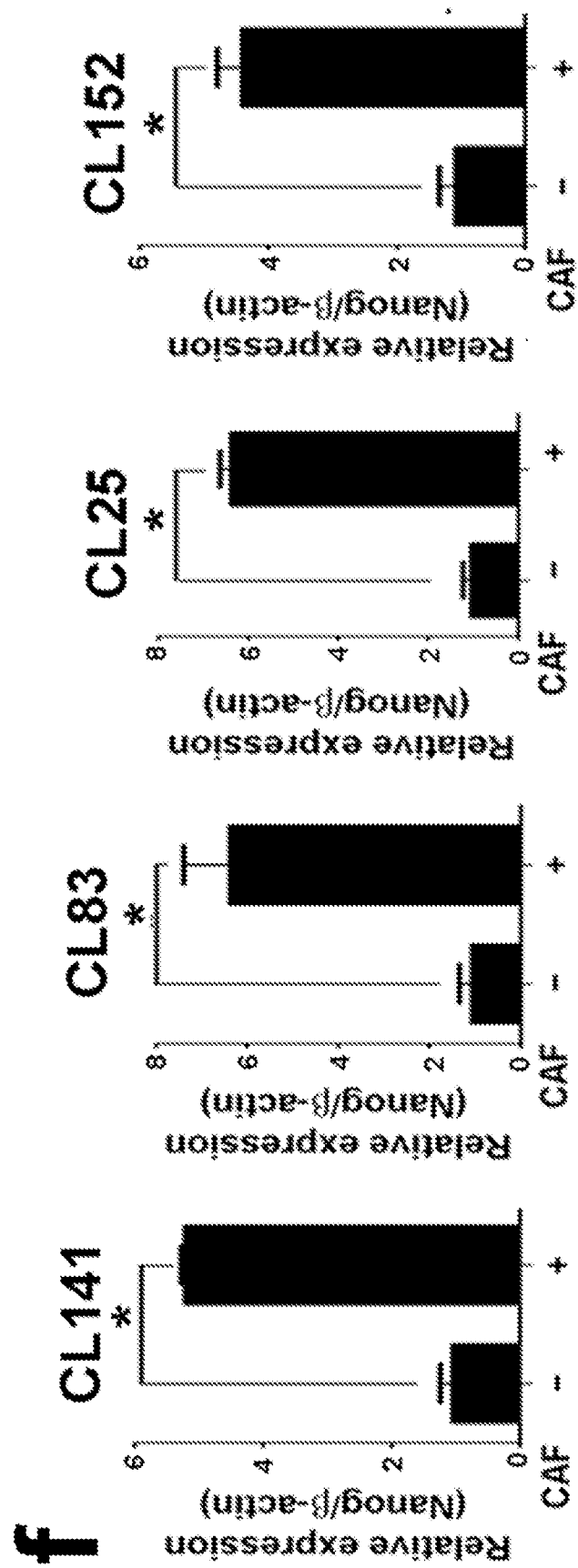
Figure 1:
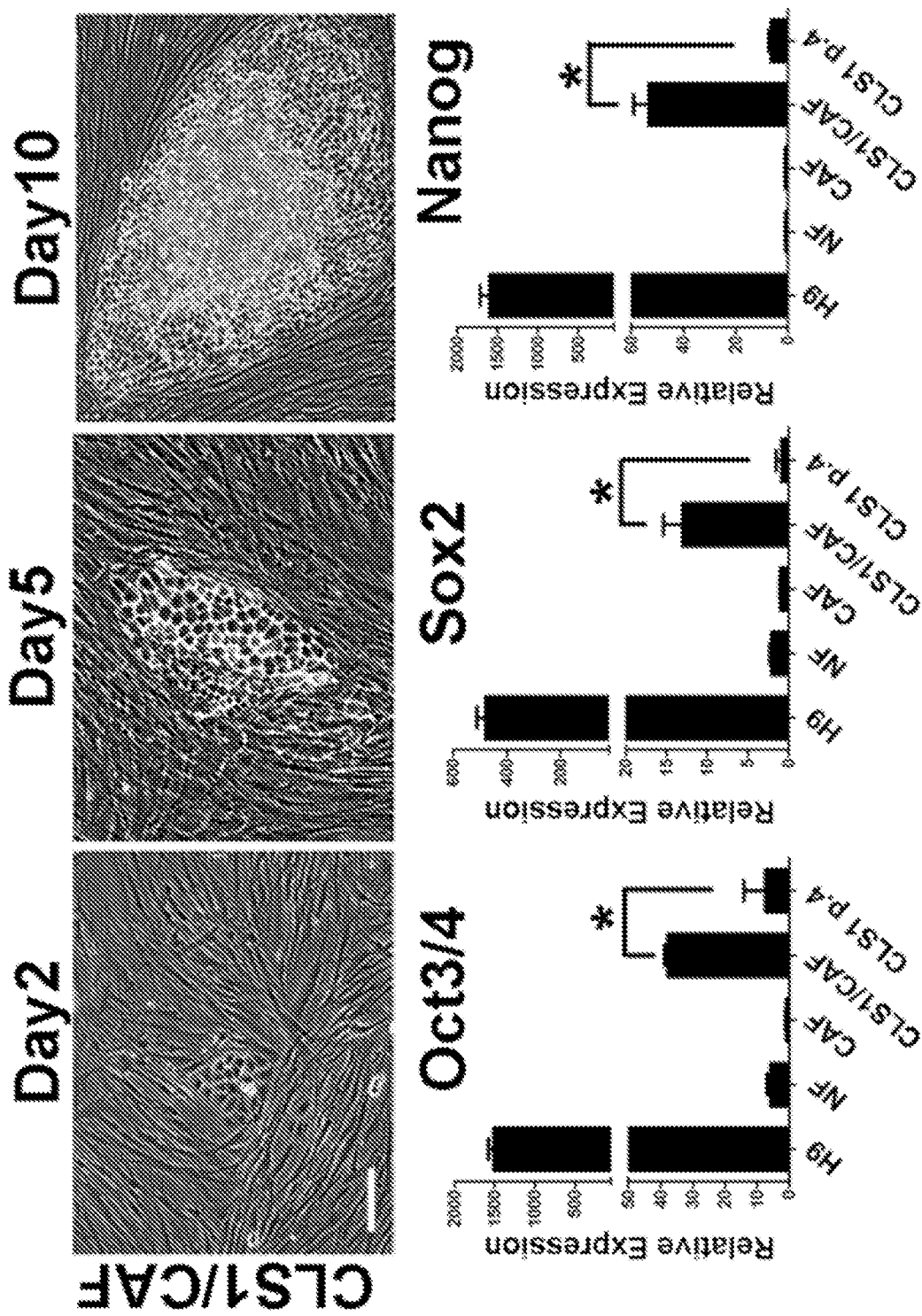
Figure 1:
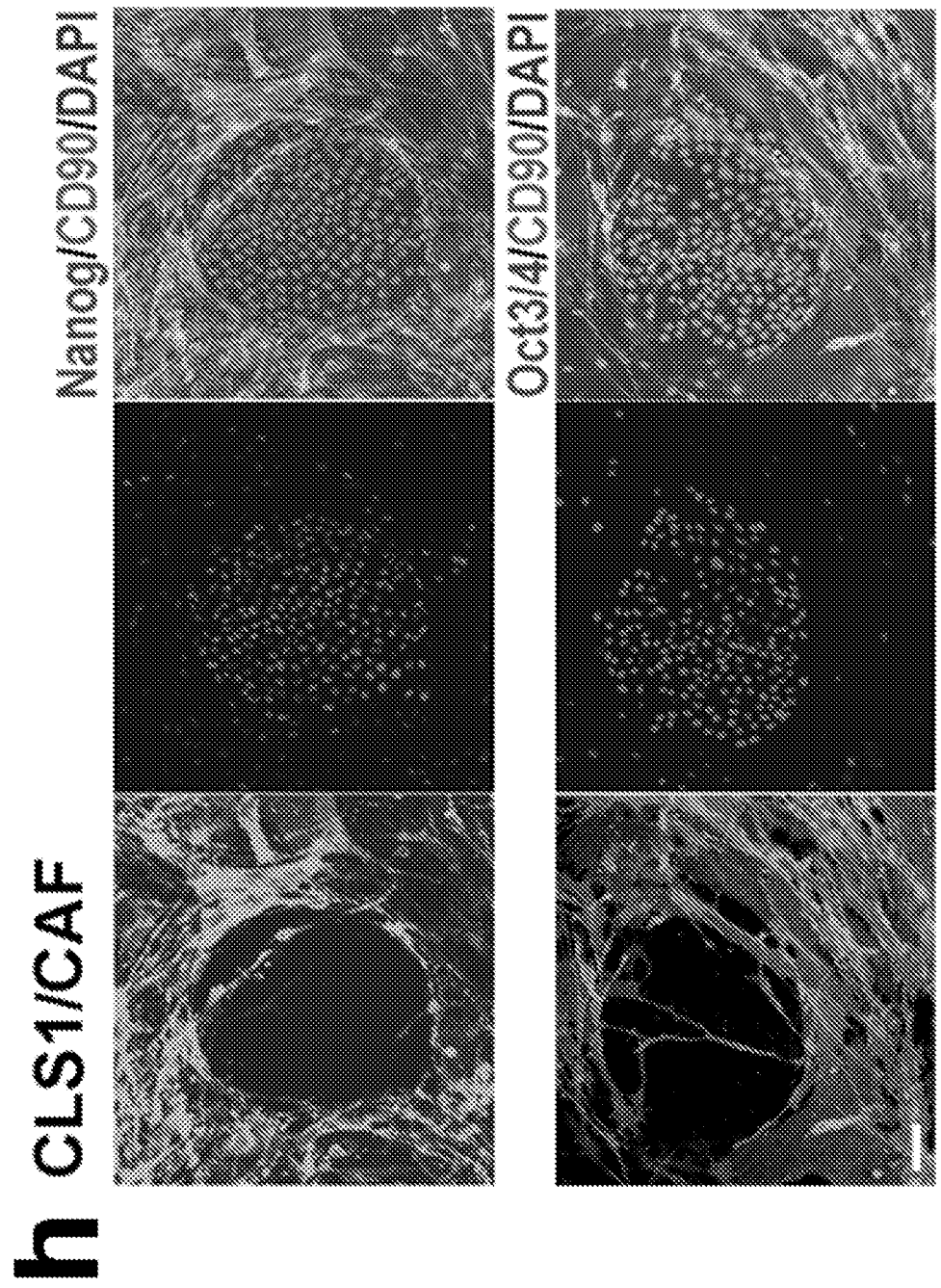
Figure 1:
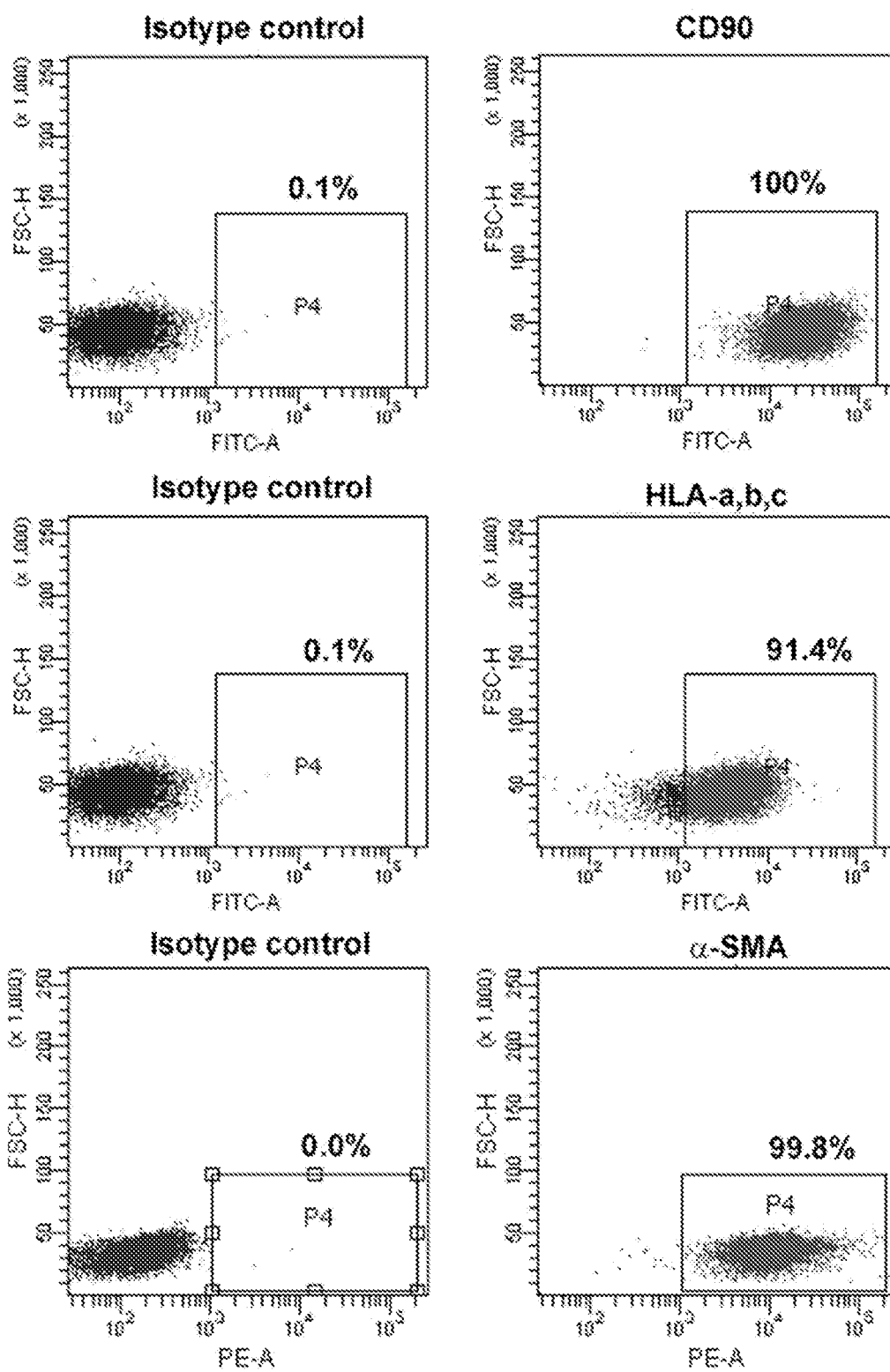

Cancer stem cells (CSCs) are a promising target for treating cancer, yet how CSC plasticity is maintained in vivo is unclear. Maintaining CSC plasticity in vitro would be difficult. The present disclosure is based at least in part on the establishment of sustainable primary cultures of Oct3/4 (+)/Nanog(+) lung CSCs fed with CD90(+) cancer-associated-fibroblasts (CAFs) to preserve cancer stem cells in the tumor microenvironment. Further, the transcriptomic approach was applied to identify a paracrine-network on the niche that supports and enriches CSCs through dedifferentiation and reacquisition of stem-cell-like properties. Specifically, IGF1R signaling was found to be activated in cancer cells in the presence of CAFs expressing IGF-II. The IGF-II/IGF1R signaling induces Nanog expression and promote stemness. Moreover, this paracrine signaling predicts overall and relapse-free survival in early stage (e.g., stage-I) cancer patients (e.g., lung cancer such as non-small-cell-lung-cancer (NSCLC) patients). Further, IGF-II/IGF1R signaling blockade inhibits Nanog expression and attenuates cancer stem cell features. The data presented herein demonstrate CAFs constitute the supporting niche for cancer stemness, and targeting this paracrine signaling may present a new therapeutic strategy for cancer such as NSCLC.

Accordingly, provided herein are an in vitro co-culture system for producing and/or maintaining cancer cell stemness and uses thereof for identifying drug candidates that are capable of reducing cancer cell stemness and thus be effective in treating cancer. Also within the scope of the present disclosure are CAF/CSC biomarkers for use in assessing cancer patient survival rate and for use in identifying cancer patients who are more likely to response to treatment targeting cancer stem cells, and kits for use in identifying cancer stem cells. Further, the present disclosure provides a high content assay for identifying cancer stem cells in a cancer sample.

I. In Vitro Co-Culturing System Comprising Cancer-Associated Fibroblasts (CAFs) and Cancer Cells for Maintaining Cancer Cell Stemness Described herein is an in vitro co-culture system comprising CAFs and cancer cells, in which CAFs facilitate maintenance of cancer cell stemness and methods of using such an in vitro co-culturing system for producing and/or maintaining cancer stem cells and for identifying drug candidates that are capable of reducing stemness of cancer cells. As used herein, the term "stemness" refers to the ability of a cell to self-renew and to generate an additional, phenotypically distinct cell type.

Cancer stem cells (CSCs) are cancer cells that exhibit stem-cell like properties. CSCs often exhibit at least one hallmark of cancer, and is capable of generating at least one additional, phenotypically distinct cell type. Furthermore, cancer stem cells are capable of both asymmetric and symmetric replication. It is appreciated that a cancer stem cell may result from differentiated cancer cells that acquire stemness traits and/or stem cells that acquire phenotypes associated with cancer cells. Alternatively, cancer stem cells can reconstitute non-stromal cell types within a tumor.

CAFs are a population of fibroblasts isolated from tumor stroma. CAFs can be large, spindle-shaped mesenchymal cells that share characteristics with smooth muscle cells and fibroblast. Kharaishvili et al., *Cancer Cell International* 2014, 14:41. They are typically characterized as having a hyper-proliferative phenotype and are capable of secreting increased amounts of growth factors, extracellular matrix components, and matrix metalloproteineases, which promote tumor growth.

The CAFs used in the in vitro co-culturing system can be primary cells obtained from a cancer patient (a human patient having a solid tumor), including, but not limited to, a lung cancer patient, a breast cancer patient, a kidney cancer patient, a prostate cancer patient, an ovary cancer patient, a skin cancer patient, a cervical cancer patient, a colon cancer patient, a liver cancer patient, a melanoma patient, an oral cancer patient, or a pancreatic cancer patient. Such a cancer patient may have not subjected to prior treatment, including chemotherapy and irradiation therapy. In some examples, the CAFs are obtained from a lung cancer patient, such as a non-small cell lung cancer patient or a small-cell lung cancer patient. The CAFs for use in the co-culture system described herein may be obtained from cancer patients of various stages, e.g., an early stage or a late stage. In some examples, the CAFs are obtained from state I lung cancer patients, such as stage I NSCLC patients. CAFs may be obtained from tumor tissues or tissues surrounding a tumor following the methods described in Example 1 below, See also Navab et al., 2011; and Tesei et al., 2009, the relevant disclosures are incorporated by reference herein. Alternatively, the CAFs used herein can be established cell lines.

The CAFs can be co-cultured with a population of cancer cells under suitable conditions allowing for proliferation and maintenance of cancer stem cells. In some instances, the population of cancer cells contain CSCs and the co-culture with CAFs maintain the stemness of the cancer cells. Maintaining stemness of cancer cells includes preserving the stem cell properties of the CSCs contained in the population of cancer cells. It also includes the de-differentiation and reacquisition of stem cell-like properties of already differentiated cancer cells. The population of cancer cells may be primary cancer cells obtained from a human cancer patient (e.g., a human patient having a solid tumor), such as those disclosed herein, e.g., a lung cancer patient. Such a cancer patient may have not subjected to prior treatment, including chemotherapy and irradiation therapy. Alternatively, the population of cancer cells may be established cancer cell lines. In a preferred embodiments, the CAFs and cancer cells are of the same type of cancer. For example, both the CAFs and cancer cells may be derived from lung cancer, such as non-small cell lung cancer or small-cell lung cancer.

In one example, a culture dish can be pre-seeded with CAF feeder cells (e.g., $1 \times 10^5$ to $1 \times 10^6$ cells per well). A population of cancer cells at a density of, e.g., 2,500 to 7,500 viable cells/ml, may be placed in the culture dish and co-cultured with the CAF feeder cells. The ratio of CAFs to cancer cells may range from 100:1 to 5:1 (e.g., 50:1, 20:1, or 10:1). Stemness of the cancer cells co-cultured with the CAF feeders may be assessed by determining the ability of cancer cells in colony formation following methods known in the art. See Examples below. Stemness of cancer cells can also be assessed by measuring CSC markers, such as IGF1R, Oct3/4, and Nango, as described herein. Alternatively, stemness of cancer cells can be determined by the image-based high content assay described herein.

The in vitro co-culturing system described herein provides a platform for identifying anti-cancer drug candidates that target cancer stem cells. Cancer stem cells have been reported to constitute a small fraction (e.g., 0.1% to 10%) of all cancer cells in a tumor. Such type of cancer cells are critical in initiating cells in the genesis of cancer as well as in the progression of cancer by evolving cells with phenotypes distinct from previous generations. Cancer stem cells typically have slow growth and replication rates and are believed to be the hardest cells to eradicate in a cancer. It was suggested that residual cancer stem cells can facilitate the replication of an entire cancer following the elimination of all other cancer cells. Thus, drug candidates capable of targeting cancer stem cells would be of particular importance in cancer treatment.

To determine whether a candidate compound is capable of reducing cancer cell stemness, such a candidate compound can be added into the in vitro co-culturing system as described herein. After being cultured under suitable conditions for a suitable period, the level of cancer cell stemness in the co-culture system can be compared with a control co-culture system that does not contain the candidate compound. If the level of cancer cell stemness in the presence of the candidate compound is reduced as compared to that in the absence of the drug candidate, it indicates that the candidate compound may be an anti-cancer drug that targets cancer stem cells.

Figure 4:
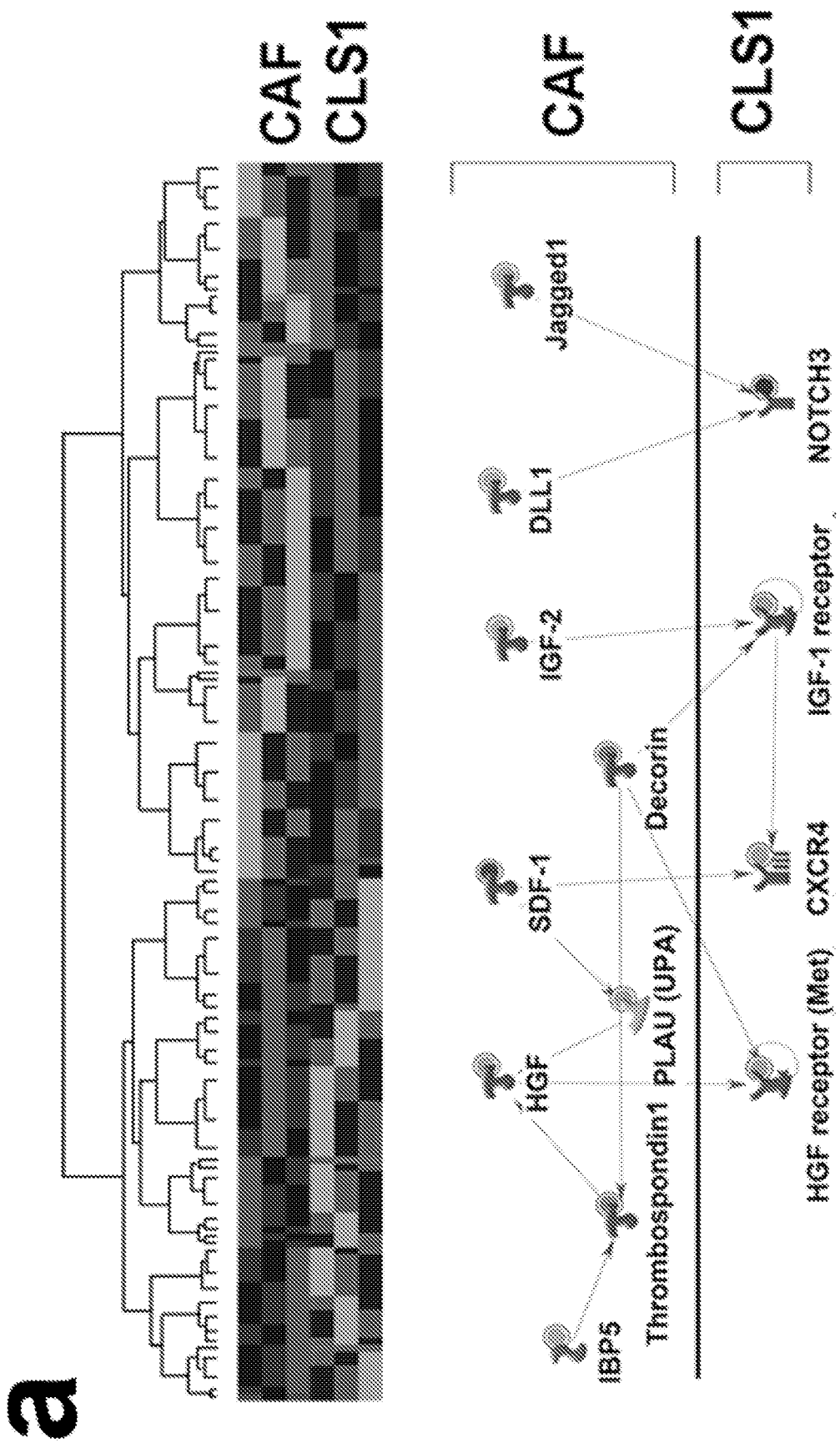
FIG. 4 includes diagrams showing paracrine networks and the corresponding receptor pathways in CSC and CAF crosstalk. (a): a diagram showing hierarchical clustering of differentially expressed genes in CSC (CLS1) cells cultured with or without CAFs. (b): charts showing RT Q-PCR validation of the paracrine regulatory pathway. CLS1 cells were derived from CLS1 spheres, dissociated to single cells and then sub-cultured without CAFs for different numbers of passages (p3, p6 and p14). CAFs served as the feeder cell control (N=3). (c): a chart showing RT Q-PCR analysis of the stem cell marker Nanog in CLS1 cells cultured in conditioned medium. The conditioned medium was collected from CLS1 cells co-cultured with CAFs (N=3). (d): diagrams showing antibody arrays, which were used to examine the growth factors secreted by CAFs or the CLS1 cells cultured with or without CAFs in serum-free RPMI medium for 24 h. The arrays were scanned and quantified, and the levels were normalized to those of the positive controls. (e): a diagram showing the semi-quantitative results of cytokine expression levels, which are represented as a heat map. (f): a chart showing RT Q-PCR analysis of the stem cell marker Nanog in CLS1 cells treated with the following cytokines: IGF-II (10 ng/ml); IGFBP1 (10 ng/ml); IGFBP2 (10 ng/ml); IGFBP3 (10 ng/ml); IGFBP4 (10 ng/ml); bFGF (10 ng/ml); HGF (10 ng/ml); PARC (10 ng/ml); sCD14 (500 ng/ml) and GM-CSF (1 ng/ml) (N=3). (g): a chart showing RT Q-PCR analysis of the stem cell marker Nanog in CLS1 cells treated with IGF-II (10 ng/ml) and combination of HGF (10 ng/ml) and sCD14 (500 ng/ml) (N=3). (h): photos showing immunofluorescence, which shows that IGF1R and IGF-II differentially localize in CLS1 cells and CAFs. IGF1R staining was observed in lung CSCs (red, upper panel). CD90-positive CAFs (green) showed staining for IGF-II (red, lower panel). The nuclei were stained with DAPI (blue; N=3). Scale bar, 50 μm. (i): charts showing RT Q-PCR analysis of IGF-II in CAFs obtained from patients and cultured with or without cancer cells (N=6 with A549 cells and N=9 with EKVX cells). (j): charts showing RT Q-PCR analysis of IGF1R in cancer cell (A549 or EKVX) cultured with or without CAFs obtained from patients (N=4 patients). (k): a schematic illustration showing the crosstalk between CSCs and CAFs that may contribute to cancer stemness. The data represent the mean±S.D. and were tested for significance using the Student's t-test (b-c, i-j) or one-way ANOVA with Tukey's post hoc corrections (f-g); *P<0.05. The data are representative of at least three independent biological experiments, with three or more replicates in each experiment.
Figure 4:
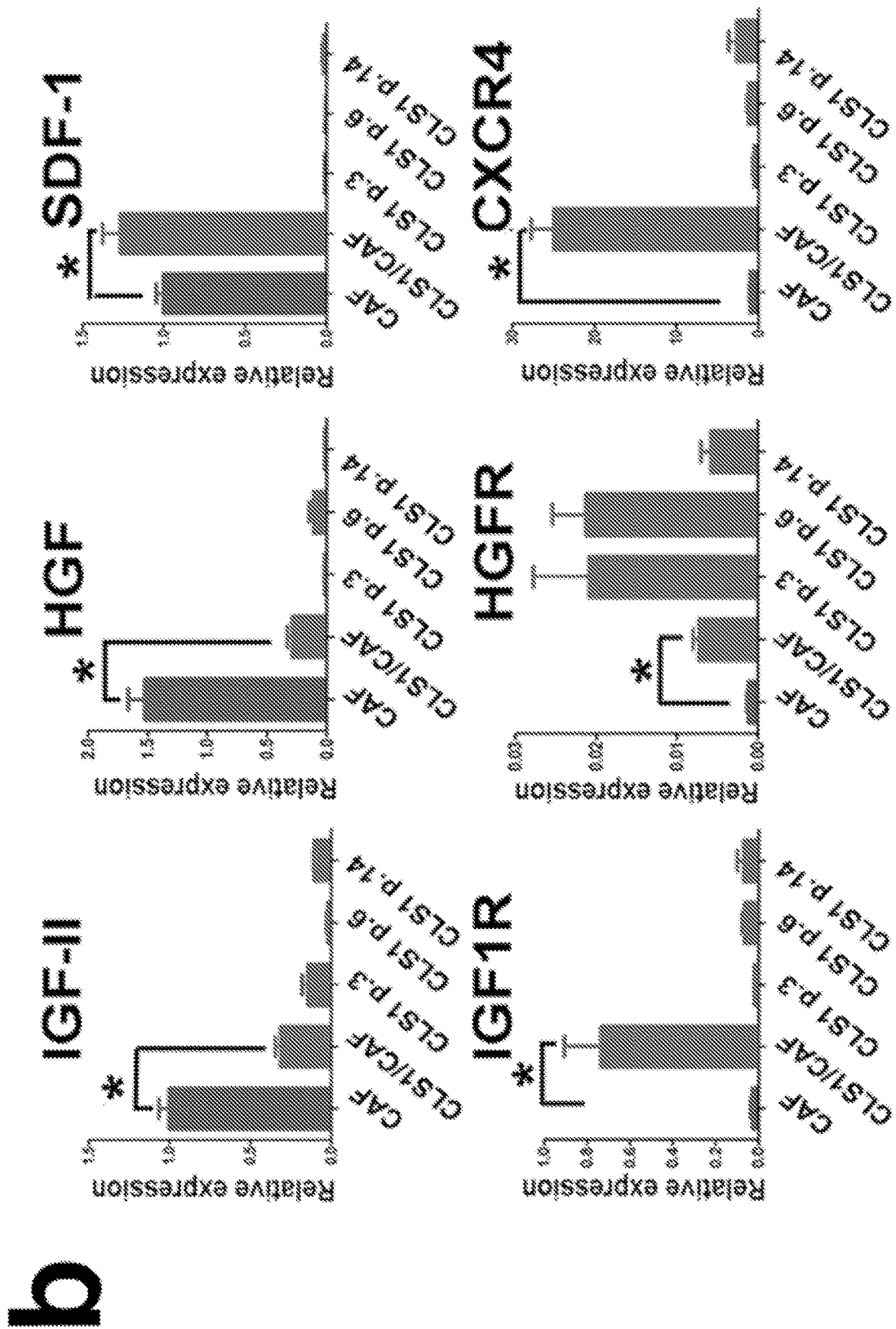
Figure 4:
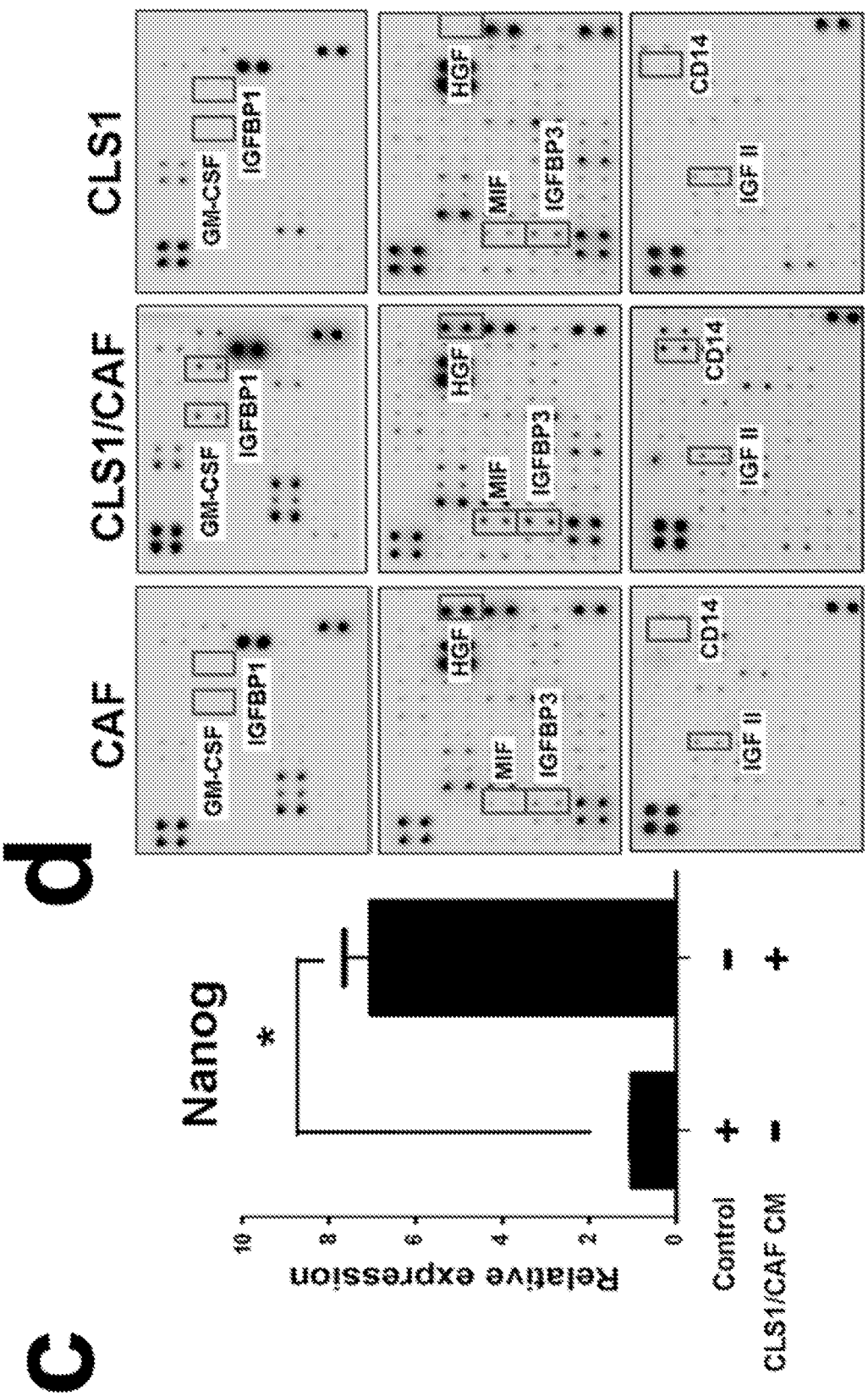
Figure 4:
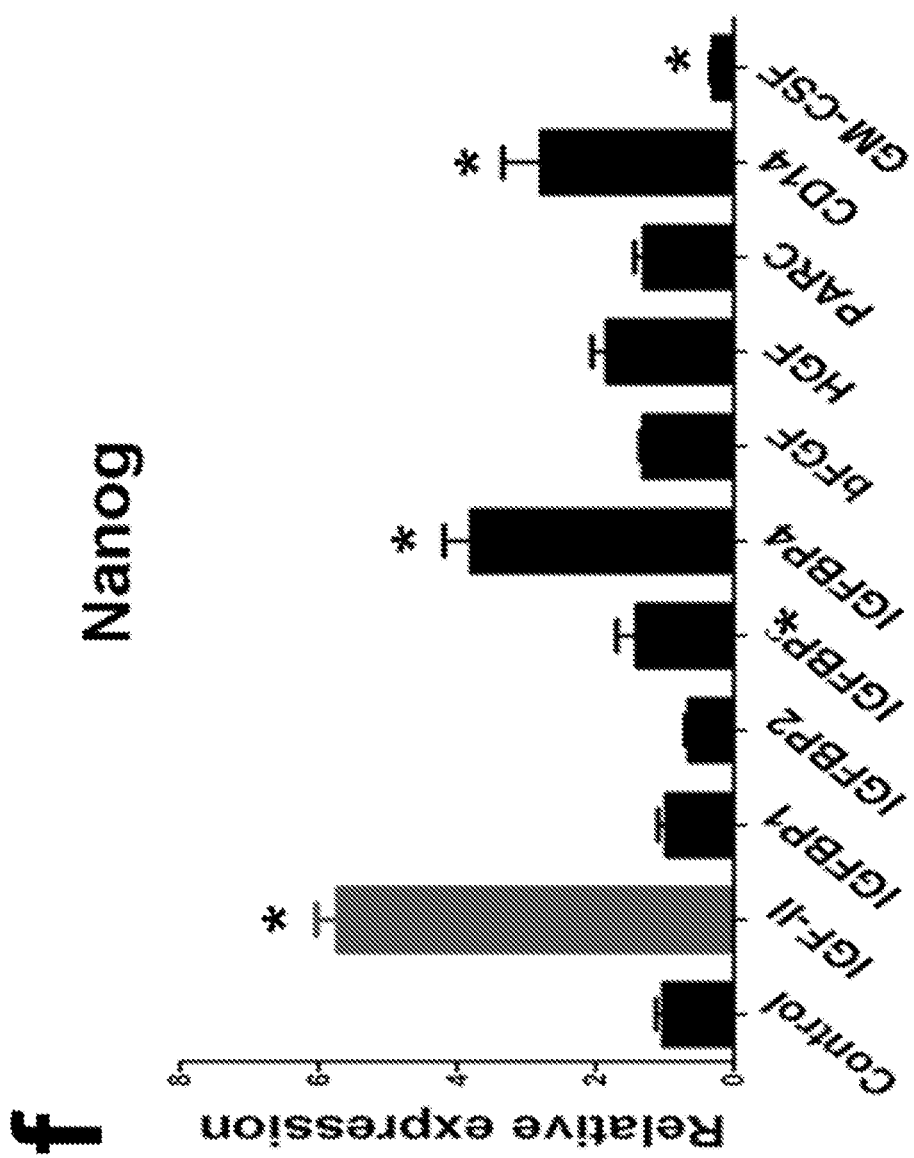
Figure 4:
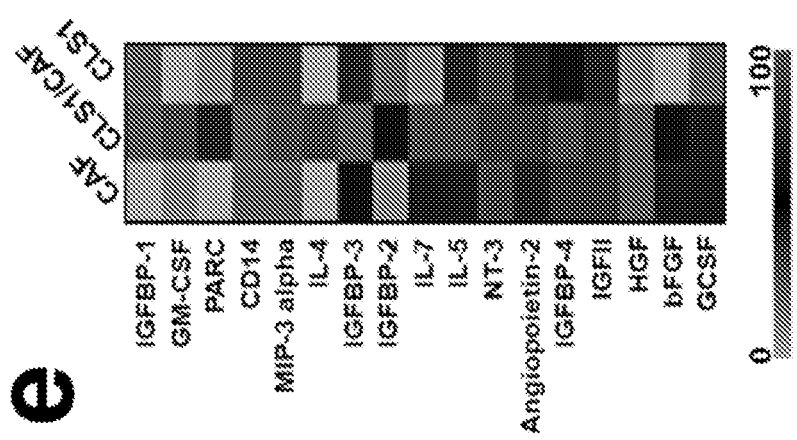
Figure 4:
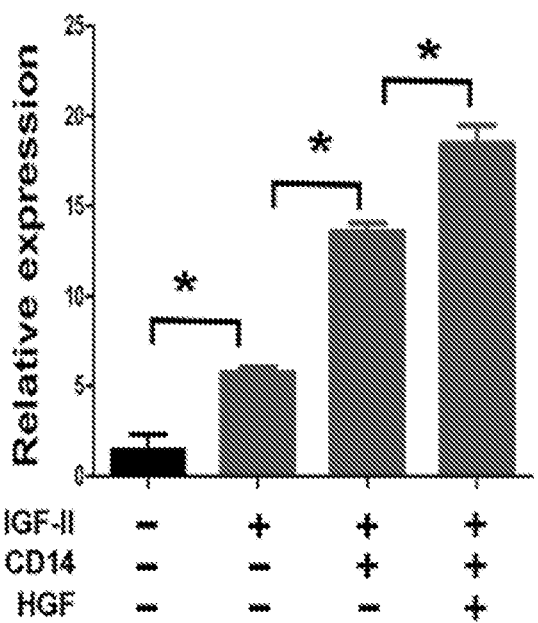
Figure 4:
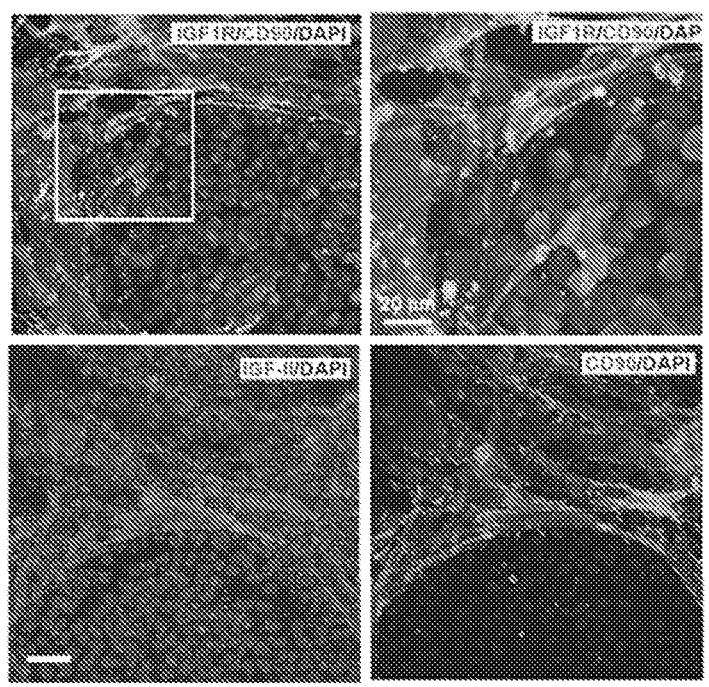
Figure 4:
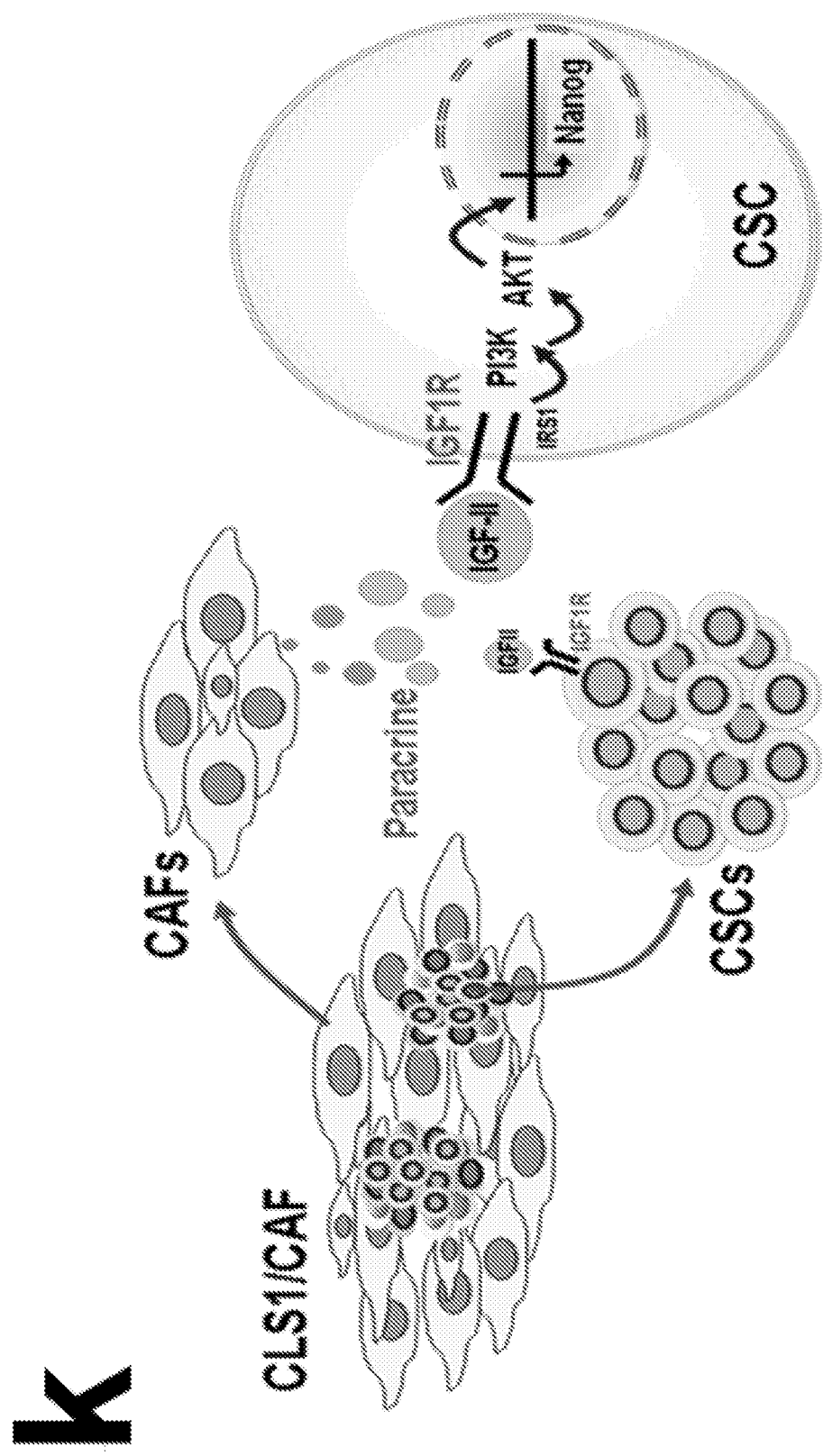

In some examples, the level of cancer cell stemness can be determined by measuring the number of $Oct3/4^+$ and $Nanog^+$ cells in the co-culture, which represent CSCs. In other examples, the level of cancer cell stemness can be determined by the level of drug resistance of the cancer cells in the co-culture. A high drug resistance represents a high cancer cell stemness. In yet other examples, the level of cancer cell stemness can be determined by measuring the level of one or more of the components of the paracrine network described herein (see FIG. 4), including IGF-II, HGF, LIF, and SDF1 expressed in the CAFs, the level of one or more of IGF1R, IGF2R, LIFR, CXCR4, and Nanog expressed in the cancer cells, or both. Expression levels of one or more of these cell surface markers can be measuring by a routine method, for example, FACS analysis or immunohistochemistry staining.

Once a candidate compound is identified in the screening method described herein, using the in vitro co-culturing system, such a candidate compound can be subject to further investigation via routine technology to confirm its anti-cancer activity, particularly its anti-cancer stem cell activity.

II. Paracrine Network that Regulates Cancer Cell Stemness

Another aspect of the present disclosure is based on the discovery of a paracrine network by which CAFs enrich CSCs through de-differentiation and reacquisition of stem cell-like properties. In particular, the IGF-II/IGF1R signaling pathway was found to play an important role in this paracrine network, triggering expression of Nanog in CSCs. It was discovered that this paracrine network represents reliable biomarkers for predicting overall and lapse-free survival in early stage of cancer patients, for example, in stage I of non-small cell lung cancer patients. Thus, one or more components of this paracrine network may be applied in the cancer prognostic methods as described herein.

Any of the components of the paracrine network disclosed herein, or a combination thereof, can be used as prognostic markers to assess survival rate (e.g., overall survival rate or relapse-free survival rate) of a cancer patient (e.g., those described herein such as a lung cancer patient, for example, a non-small cell lung cancer patient, or a small-cell lung cancer patient) in an early stage, for example, stage I of a NSCLC patient. Exemplary components of the paracrine network are provided in FIG. 4. Examples include, but are not limited to, IGF-II, hepatocyte growth factor (HGF), LIF, and stromal cell-derived factor 1 (SDF1) expressed in CAFs, and the corresponding receptors expressed in CSCs, e.g., IGF1R, IGF2R, HGF receptor (HGFR), LIFR, and C-X-C chemokine receptor type 4 (CXCR4). Other biomarkers such as Nanog and IGF-binding proteins (IGFBPs) in CSCs also can be used as the prognostic markers. In one example, the biomarkers used in the prognostic method described herein include IGF-II expressed by CAFs and IGF1R or Nanog expressed by CSCs. See also Example 1 below.

To practice this method, a tissue sample containing cancer cells and CAFs can be collected from a cancer patient (e.g., having a solid tumor such as those described herein) via routine methods. The expression level(s) of one or more of the biomarkers described herein can be measured via, e.g., IHC analysis as described above. The levels of the one or more biomarkers thus obtained can be normalized and optionally processed following the procedures described above to generate an expression profile of the sample. An elevated expression level of the one or more biomarkers (e.g., IGF-II and IGF1R or Nanog) as compared to a predetermined value indicates that the patient has a poor survival rate. On the other hand, a lower expression level of the one or more biomarkers as compared to the predetermined value indicates that the patient has a good survival rate. In some examples, the predetermined value may represent the average expression level of a biomarker in a population of an early stage cancer patients (e.g., Stage I NSCLC patients). Based on the patient's survival rate as assessed by the prognostic method described herein, an appropriate treatment can be determined.

Any of the prognostic biomarkers can also be used for identifying cancer patients who are more likely to respond to cancer therapy, such as cancer therapy that targets the IGF-II/IGF1R signaling pathway (e.g., antibodies specific to IGF-II or IGF1R). Thus, provided herein are methods for treating a cancer patient who exhibited an elevated level of one or more of the biomarkers as described herein with an agent that interferes with the IGF-II/IGF1R signaling pathway. In some examples, the cancer patient can have a solid tumor, such as lung cancer (e.g., NSCLC or SCLC), breast cancer, kidney cancer, prostate cancer, ovary cancer, skin cancer, cervical cancer, colon cancer, liver cancer, melanoma, oral cancer, or pancreatic cancer. The patient may have an elevated level IGF-II expressed by CAFs and/or an elevated level of IGF1R and/or Nanog expressed by CSCs as determined by, e.g., an IHC assay. Agents that can interfere with the IGF-II/IGF1R signaling pathway may include, but not limited to, anti-IGF-II antibodies, or anti-IGF1R antibodies.

The present disclosure also provides kits for use in identifying cancer stem cells and the level of cancer cell stemness in a sample. Such kits can include a first agent for detecting a first biomarker of the paracrine network (e.g., IGF-II expressed by CAFs) and a second agent for detecting a second biomarker of the paracrine network (e.g., IGF1R or Nanog expressed by CSCs) and optionally a third agent for detecting a third biomarker of the paracrine network (e.g., IGF1R if the second agent is specific to Nanog or Nanog if the second agent is specific to IGF1R).

In some examples, the first, second, and/or third agents are antibodies specific to the biomarkers. An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used in the methods described herein can be murine, rat, human, or any other origin (including chimeric or humanized antibodies). Any of the antibodies described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In some embodiments, the kit can comprise instructions for use in accordance with any of the methods described herein. The included instructions can comprise a description of using the first, second, or third agent for measuring the level of the corresponding biomarkers as expressed by a population of cells of interest (CAFs or CSCs). The kit may further comprise a description of selecting an individual suitable for the analysis.

The kits of this invention are in suitable packaging. Suitable packaging includes, but is not limited to, vials, bottles, jars, flexible packaging (e.g., sealed Mylar or plastic bags), and the like.

III. High-Content Assay (HCA) for Identifying Cancer Stem Cells

Also described herein is an image-based high content assay (HCA) for analyzing the level of cancer cell stemness in a sample comprising both cancer cells and CAFs. A schematic illustration of an exemplary HCA method is provided in FIG. 14a.

This assay may involve the use of a first agent for detecting a maker of CAFs (e.g., CD90) and a second agent for detecting a marker of cancer stem cells (e.g., Nanog). In some embodiments, the first agent, the second agent, or both can be antibodies. For example, the first agent can be an anti-CD90 antibody and the second agent can be an anti-Nanog antibody.

To perform an HCA, CSCs can be cultured in the presence of CAFs as feeder cells. The ratio of CSCs to CAFs may range from 1:100 to 1:5 (e.g., 1:50, 1:20, or 1:10). The CSCs and CAFs may be co-cultured under suitable conditions for a suitable period (e.g., 72 hours) to allow formation of cancer cell colonies, a feature of cancer stem cells. Cell clusters greater than 10,000 $\mu m^2$ may be deemed as a cell colony.

A sample containing CSCs and CAFs can be reacted with the first agent and the second agent as described herein. In some embodiments, the first agent, the second agent, or both are directly conjugated with labels, for example, fluorescent dyes, wherein the first agent and the second agent are conjugated with different labels. In other embodiments, one or both of the first and second agents are not directly labeled. In that case, a secondary agent (labeled) that is specific to either the first or the second agent may be used to such that a label is indirectly conjugated to the first or second agent.

In one example, the CSC/CAF-containing sample is stained with an anti-Nanog antibody and an anti-CD90 antibody, the latter being conjugated with FITC. After being washed sufficiently to remove unbound antibodies, the sample is further reacted with a secondary antibody that is specific to the anti-Nanog antibody. The secondary antibody can be labeled with TRITC.

The CSC/CAF-containing sample may further stained with an agent that recognizes nuclei (DAPI).

The stained samples may be imaged, e.g., using a high-content analysis platform with a 4× objective. See Example 2 below. The images can be analyzed using methods known in the art, for example, the MetaXpress® software (Molecular Devices). The cancer cell nuclei (CD90-) can be identified using, e.g., Multi-Wavelength Cell Scoring. Cancer cell colonies can then be identified using the methods described herein (see Example 2). The number of Nanog$^+$ cells (e.g., TRITC-stained cell), representing CSCs, and the total cell number can be determined. The stemness of each cancer colony can be calculated as the ratio of Nanog-positive (TRITC-stained) cells to total cells. The colony density can be defined as the total cell count divided by the colony area.

The total number of CAF feeder cells can be determined by countering CD90$^+$ (e.g., FITC positive) cells. Cells per colony and the total stem cell number of all colonies in each well can be determined by the average cells per colony and the total cells of all colonies in each well respectively. Stem cells per colony and total colony stem cells can be calculated by the average stem cells per colony and the total stem cells of all colonies in each well, respectively.

The HCA method can be used as a high-throughput screening platform for identifying drug candidate capable of reducing cancer cell stemness. For example, a candidate compound can be added to the CSC/CAF co-culture, which can be incubated under suitable conditions for a suitable period. The level of cancer stemness can be determined as described herein. If the candidate compound reduces cancer cell stemness as relative to that in the absence of the candidate compound, such a candidate compound can be identified as a potential anti-cancer drug capable of reducing cancer cell stemness.

This screening platform can be applied to identify drug candidate for treating any types of cancer, in particularly solid tumors, depending upon the type of CSCs/CAFs used in the HCA method. For example, the CSCs and CAFs may be derived from a patient having, e.g., lung cancer, breast cancer, kidney cancer, prostate cancer, ovary cancer, skin cancer, cervical cancer, colon cancer, liver cancer, melanoma, oral cancer, or pancreatic cancer.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Cancer-Associated Fibroblasts Regulate the Plasticity of Lung Cancer Stemness Via Paracrine Signaling The present study relates to a sustainable primary culture of Oct3/4(+)/Nanog(+) lung CSCs fed with CD90(+) cancer-associated-fibroblasts (CAFs) to further advance preserving stem cells in the tumor microenvironment. Here, a transcriptomic approach was applied and a paracrine-network was identified as the niche that supports and enriches CSCs through dedifferentiation and reacquisition of stem-cell-like properties. Specifically, it was observed that IGF1R signaling activation in cancer cells in the presence of CAFs expressing IGF-II can induce Nanog expression and promote stemness. Moreover, this paracrine signaling predicts overall and relapse-free survival in stage-I non-small-cell-lung-cancer (NSCLC) patients. Further, IGF-II/IGF1R signaling blockade inhibits Nanog expression and attenuates cancer stem cell features. Data from this study demonstrates that CAFs constitute the supporting niche for cancer stemness, and targeting this paracrine signaling may present a new therapeutic strategy for NSCLC. Chen et al., *Nature Communication*, 5:3472 (2014), the content of which is incorporated by reference herein.

Materials and Methods (i) Lung Cancer Cell Lines, Patients and Tumor Specimens

The human NSCLC cell lines NCI-A549, NCI-H460, H1975 and NCI-EKVX were obtained from the National Cancer Institute (National Institutes of Health, Bethesda, Md., USA) or the American Type Culture Collection (ATCC, Manassas, Va., USA). Human lung cancer cell lines CL25, CL83, CL141 and CL152 were established using primary cultures from lung cancer patients with adenocarcinomas. The cells were cultured in RPMI 1640 medium supplemented with 10% FBS at 37° C. under a humidified atmosphere consisting of 20% $O_2$ and 5% $CO_2$.

Lung tumor tissue specimens were obtained from patients (N=80) with histologically confirmed NSCLC who had undergone complete surgical resections. The enrolled patients were classified as stage I, and they had not been previously treated with neoadjuvant chemotherapy or irradiation therapy. All specimens were formalin-fixed, sectioned, stained with H&E and examined through microscopy. Pathological staging was performed according to the international staging system for lung cancer. Zuo, et al. *J Cell Biochem* 113:2567-2575 (2012).

(ii) Primary Cultures of Lung Cancer Stem Cells (CSCs), Cancer-Associated Fibroblasts (CAFs) and Normal Fibroblasts (NFs)

Human lung CSCs and CAFs were harvested from freshly resected lung tumor tissues from lung cancer patients who underwent surgical resections. The demographic information of some of the patients is provided in Table 2 below. Tumors and paired normal tissues were harvested within 30 min after resection to isolate primary lung CSC, CAF and NF cultures using a modified protocol. Navab, et al. *Proc Natl Acad Sci USA* 108:7160-7165 (2011); and Tesei, et al. *Cell Prolif* 42: 298-308 (2009).

Lung CSCs were isolated from cancer-associated regions of resected tissues from NSCLC patients and were cultured and maintained with feeder cells, i.e., stromal fibroblasts. The samples were procured and utilized according to approved IRB protocols for research on human subjects. Non-cancer associated stromal was sampled by a pathologist at least 5 cm away from neoplastic lesions (under sterile conditions) within 30 min after resection, as determined by gross examination at the time of surgical excision and subsequent histological analysis. The tissues were processed based on a previously described protocol with modifications. Dontu, et al. *Genes Dev* 17:1253-1270 (2003). In brief, the tissues were minced and incubated for 6-12 h in the presence of deoxyribonuclease 1 (1 mg/ml; Bioshop) and protease (1 mg/ml; Sigma) in S-MEM medium (GIBCO) at 4° C. After digestion, cell clumps were sieved through a 40-µm cell strainer (Falcon) to obtain single-cell suspensions. The collected cells were cultured at different cell densities ($5\times10^5$) in a 24-well plate with the modified culture conditions in RPMI1640 with 10% FBS at 37° C. in a humidified atmosphere containing 20% $O_2$ and 5% $CO_2$. After 30 days of culture, sphere-like colonies could be identified with the surrounding stroma cells. Sub-culturing of sphere-like cells was performed as previously described with some modifications. Dontu, et al., 2003. The spheres were collected through gentle centrifugation (58 g, 800 rpm) after 7-10 days and dissociated enzymatically (10 min in 0.05% trypsin, 0.53 mM EDTA.4Na; Invitrogen) and mechanically using a fire-polished Pasteur pipette. The cells obtained from dissociation were passaged through a 40-µm sieve and analyzed microscopically for single-cell status. The cells, at a density of 5,000 viable cells/ml, were plated in plates pre-seeded with stromal cells as feeders ($5\times10^5$ cells/well). For the single cell/well clone experiments, the cells were plated in 96-well plates using a cell sorter during FACS (FACS Ariel), and the wells had been pre-seeded with feeder cells (2,000 cells/well). Sub-culturing of lung CSCs was performed as previously described with some modifications. Dontu et al., 2003. Briefly, spheres were collected through gentle centrifugation (58 g, 800 rpm), enzymatic digestion (10 min with 0.25% trypsin, 1 mM EDTA; Invitrogen) and mechanic disruption. The lung CSCs obtained from this dissociation were passaged through a 100-µm strainer, and the sieved cells were analyzed microscopically. The single cells, at a density of 5,000 viable cells/ml, were plated on 10-cm dishes pre-seeded with CAF feeder cells ($5\times10^5$ cells/well).

(iii) Colony Purification Using the Cyntellect LEAP™ System

Cancer cells were dissociated to single cells using trypsin in an EDTA-containing solution, and the single-cell suspension (500 viable cells/well) was added to C-Lect™ 6-well plates pre-seeded with stromal cells ($5\times10^4$ cells/well). After colony formation, individual cells were purified using the LEAP™ system (Cyntellect). The LEAP™ Stem Cell Colony Purification Application Guide was followed. The plate was loaded into the LEAP™ instrument and processed using the colony purification application protocol. Image processing and gating of the colony purification region was performed with square shapes. The LEAP™ system displayed images of the selected cells for preview. Cell ablation was individually targeted using a green laser. After LEAP processing, the cultured cells were removed from the well with trypsin and cultured using standard cell culturing conditions.

(iv) Real-Time Reverse Transcriptase (RT) Q-PCR

The expression level of stemness-related genes and validation of the Affymetrix microarray data for CAF, CLS1/CAF and CLS1 were performed through RT Q-PCR using an ABI Prism 7900 Sequencer (Applied Biosystems). The primers were designed using Primer Express 3.0 (Applied Biosystems) as shown in the table below:

TABLE 1

Primer list for Q-PCR

| Gene symbol | Unigene ID | Forward primer | SEQ ID NO: | Reverse primer | SEQ ID NO: |
|---|---|---|---|---|---|
| POU5F1 | Hs.24918 | TTCAGCCAAACGACCATCTG | 1 | GAACCACACTCGGACCACATC | 19 |
| SOX2 | Hs.518438 | CACACTGCCCCTCTCACACAT | 2 | CCCATTTCCCTCGTTTTTCTT | 20 |
| NANOG | Hs.661360 | CACCAGTCCCAAAGGCAAAC | 3 | GCCTTCTGCGTCACACCATT | 21 |
| IGF-II | Hs.523414 | GGCGGCATTTGGGATACA | 4 | TCTGTCATGGTGGAAAGATGGA | 22 |
| IGF1R | Hs.649408 | TACAAAGGGCCATCGTTCATC | 5 | TCCGGACACGAGGAATCAG | 23 |
| IGF2R | Hs.487062 | GCAGAAGCTGGGTGTCATAGGT | 6 | CACGGAGGATGCGGTCTTA | 24 |
| TGFBR1 | Hs.494622 | TCCTTCAAACGTGCTGACATCT | 7 | TGGAACATCGTCGAGCAATTT | 25 |
| SMAD2 | Hs.12253 | GCCACCTTGCAGGTTCGA | 8 | CAGACCCACCAGCTGACTTCTT | 26 |
| TCF21 | Hs.78061 | TCCTGGCTAACGACAAATACGA | 9 | GGGCCACGTCAGGTTGAC | 27 |
| EGR1 | Hs.326035 | TTTCACGTCTTGGTGCCTTTT | 10 | CCCTCACAATTGCACATGTCA | 28 |
| LIF | Hs.2250 | TCTCTAGTTCCCCACCTCAATCC | 11 | TTGTCACCCAAGGCCATGT | 29 |
| LIFR | Hs.133421 | CCAACATGACTTGCGACTACGT | 12 | CCTGGTCGAAACTCATCAGATTC | 30 |
| HGF | Hs.396530 | CAAATGTCAGCCCTGGAGTTC | 13 | CCGATAGCTCGAAGGCAAAA | 31 |
| HGFR | Hs.132966 | GCTAAAATGCTGGCACCCTAAA | 14 | GATATCCGGGACACCAGTTCAG | 32 |
| SPARC | Hs.111779 | ATGCGGGACTGGCTCAAG | 15 | CAGTCAGAAGGTTGTTGTCCTCAT | 33 |
| DCN | Hs.156316 | GCCCACCTGGACACAACAC | 16 | GGACCGGGTTGCTGAAAAG | 34 |
| THBS1 | Hs.164226 | cATCCGCAAAGTGACTGAAGAG | 17 | CTGTACTGAACTCCGTTGTGATAGC | 35 |
| ACTB | Hs.520640 | CTGGAACGGTGAAGGTGACA | 18 | CGGCCACATTGTGAACTTTG | 36 |

TATA-box binding protein (TBP) and β-actin were used as internal controls. The expression levels were normalized to TBP and defined as $-\Delta CT = -[CT_{target} - CT_{TBP}]$. The relative expression ratio was calculated as the fold change relative to the control ($2^{-\Delta\Delta CT}$). The experiments were performed in triplicate.

(v) Immunoflurescence Microscopy

Cells were fixed with 4% paraformaldehyde in phosphate buffered saline (PBS) at room temperature. A standard immunofluorescence protocol was followed. Ginestier, et al. Cell Stem Cell 1:555-567 (2007). Blocking and hybridization were performed in 3% (wt/vol) bovine serum albumin (BSA) in PBS. Monoclonal antibodies (mAbs) targeting Nanog (ReproCELL; 1:300) and Oct3/4 (H134; Santa Cruz; 1:100), as well as CD90 FITC-conjugated (5E10; BD Pharmingen; 1:100), cytokeratin-7 (Dako; 1:50), cytokeratin-20 (Dako; 1:25), keratin-5/6 (Thermo; 1:10), and thyroid transcription factor (TTF1; Dako) antibodies, were used. The stained cells were examined using an Axiovert 200 microscope (Carl Zeiss, Gottingen, Germany), a confocal laser scanning microscope (Clsi, Nikon, Japan) with MetaXpress® (Molecular Devices) or flow cytometry (FACSAria, Becton Dickinson).

(vi) PKH26 Retention Assay

Lung CSCs ($10^6$ cells/100 μl) were labeled with 2 μM PKH26 red (Sigma) and incubated for 5 min at room temperature. Bertolini, et al. Proc Natl Acad Sci USA 106:16281-16286 (2009). The labeled cells were washed three times with culture medium. The labeled cells were co-cultured with or without CAFs for 1 week. Distinctly red-fluorescent, stained cells were monitored using fluorescence microscopy.

(vii) Ultra-Low Sphere Forming Assay

An ultra-low sphere-forming assay was performed as previously described (Dontu, et al., 2003) and modified as the following procedures. A single-cell suspension of lung CSCs in MCDB201 serum-free medium (Invitrogen) supplemented with 20 ng/ml EGF (Sigma) and 20 ng/ml bFGF (Invitrogen) was seeded in ultra-low adherent 24-well plates (Corning, Corning, N.Y., USA; 200 viable cells/well). The medium was supplemented with fresh growth factors twice weekly. After 3 weeks, the spheres were examined under the Axiovert 200 microscope.

(viii) SP Analysis

Hoechst staining was performed as previously described (Goodell et al., J Exp Med 183: 1797-1806; 1996) and modified as the following procedures. The cells were suspended at a density of $1 \times 10^6$ cells/ml in prewarmed PBS (Invitrogen), and Hoechst 33342 dye (Invitrogen) was added at a final concentration of 5 μg/ml in the presence or absence of reserpine (50 μM; Sigma). The cells were incubated at 37° C. for 120 min with intermittent shaking, and at the end of the incubation, the cells were washed with PBS, centrifuged at 4° C. and resuspended in PBS. Propidium iodide (2 μg/ml; Invitrogen) was added to gate viable cells. The suspension was then filtered through a 40-μM cell strainer to obtain a single-cell suspension before cell sorting. Analysis and sorting were performed using the FACSAria instrument (Becton Dickinson). The Hoechst 33342 dye was excited at 375 nm, and the fluorescence was analyzed by dual-wavelength detection (blue, 450/20; red, 670LP).

(ix) ALDEFLUOR Assay

ALDH activity of cells was measured using the ALDEFLUOR assay kit (StemCell Technologies) based on the manufacturer's protocol and a previous report. Ginestier, et al., 2007. After different treatments, the cells were suspended in the ALDEFLUOR assay buffer containing the ALDH substrate BODIPY-aminoacetaldehyde (BAAA, 1 mM per $1 \times 10^6$ cells, incubate 30 min at 37° C.). As a negative control, the cell sample was treated with diethylaminobenzaldehyde (DEAB), a specific ALDH inhibitor. Nonviable cells were identified by propidium iodide staining and analysis using the FACSAria instrument (Becton Dickinson).

(x) Drug Resistance Assay

An MTT [3-(4,5-dimethylthiazolyl-2)-2,5-diphenyltetrazolium bromide] (Sigma) assay was performed to determine cell proliferation. Briefly, CLS1/CAF and CLS1 cells were added to 96-well plates at a density of $5 \times 10^3$ cells/well. After incubating for 24 h, the cells were serum-starved overnight. The cells were then treated with different concentrations (0-50 µM) of the drugs docetaxel, cisplatin, etoposide and vinorelbine for 48 h. After 48 h, the culture medium containing 0.5 mg/ml MTT was added to each well. After 1.5 h of incubation, the medium was removed, and DMSO was added to the plates. The color intensity of the solubilized formazan was measured at 570 nm in an ELISA plate reader (Vector3; Perkin-Elmer, USA).

(xi) Xenograft Tumor Formation in SCID Mice

Six-week-old male SCID mice were used for the subcutaneous injection of lung cancer cells or CSCs in low doses ($10^6$, $10^5$, $10^4$, $10^3$ or $10^2$ viable cells in 100 µl of HBSS mixed in Matrigel). The mice were monitored for 8 weeks, and the incidence of tumor formation and metastasis was examined. The tumor sections were stained with hematoxylin and eosin (H&E) and analyzed by IHC using antibodies targeting Nanog (ReproCELL), Oct3/4 (Santa Cruz; H-134) and vimentin (NCL-L-VIM-V9). The staining was visualized using an Ultra Vision detection system with an HPR polymer (Dako) and the diaminobenzidine (DAB) chromogen (Dako) followed by counterstaining with hematoxylin.

(xii) Gene Expression Profiling and Pathway Analysis

The gene expression profiling map of CAF, CLS1/CAF and CLS1 was obtained using the Affymetrix GeneChip system (Affymetrix, Inc., Santa Clara, Calif., USA) according to the manufacturer's protocol. Gene expression profiling was performed using the Affymetrix GeneChip system (Affymetrix, Inc., Santa Clara, Calif., USA) according to the manufacturer's protocol.

The array data were processed by the National Taiwan University Microarray Core Facility for Genomic Medicine. Briefly, total RNA isolated from CAFs, lung CSCs and cancer cells was used to generate cDNA (Superscript Choice System, Gibco BRL Life Technologies) with T7-(dT)$_{24}$ primers. Biotin-labeled ribonucleotides were synthesized using a BioArray high-yield RNA transcript labeling kit (Enzo Diagnostic, Inc.) and hybridized onto the human Genome U133 Plus 2.0 chip (Affymetrix). Gene expression data network and enrichment analysis of the gene list was performed using MetaCore from GeneGo Inc. (genego.com/metacore.php).

(xiii) Human Chemokine and Cytokine Antibody Arrays

Human cytokine antibody arrays (C Series 4000, Ray Biotech, Inc.) were used according to the manufacturer's instructions. Acosta, et al., Cell 133:1006-1018 (2008). Briefly, serum-free media from CAF cultures, CLS1/CAF co-cultures and CLS1 cultures were collected and incubated with the blocked membranes for 24 h at 4° C. with gentle shaking. After development, the chemiluminescent signals were captured using the Fujifilm LAS 3000 system (Fujifilm, Tokyo, Japan), and the images were processed with ImageJ software. The intensity of the chemiluminescent signal was normalized to that of the internal positive control.

(xiv) Western Blot Analyses

The detailed procedures were performed as described in Zoller, Nat Rev Cancer 11:254-267 (2011). The primary antibodies for p-IGF1R (Y1316, 6113S; 1:1000), p-AKT (D9E; 1:1000), AKT (927L; 1:1000) and Nanog (D73G4; 1:1000) were purchased from Cell Signaling Technology, Inc., and the primary antibody for IGF1R (C-20; 1:1000) was purchased from Santa Cruz. Monoclonal mouse anti-β-actin (Chemicon, Millipore; 1:5000) was used as a loading control. The membranes were then washed three times with TBST, followed by incubation with horseradish peroxidase (HRP)-conjugated secondary antibody (1:5,000) in TBST/2% skim milk. Bound antibody was detected using the Enhanced Chemiluminescence System (Santa Cruz, Calif.). Chemiluminescent signals were captured using the Fujifilm LAS 3000 system (Fujifilm, Tokyo, Japan). All experiments were performed at least three times in duplicate.

(xv) Immunohistochemistry Analysis Tumor Samples from Lung Cancer Patients

The detailed procedures were performed as described in Wielenga, et al. Am J Pathol 154:515-523 (1999) and modified as the following procedures. IHC staining of tumor tissue samples from patients with NSCLC was performed using a modified UltraVision quanto HRP-DAB detection system (Thermo, UK). The sections used for IHC analysis of IGF-II, IGF1R, Nanog, and proliferating cell nuclear antigen (PCNA) protein expression were first autoclaved in Antigen Retrieval AR-10 Solution (Biogenex) or Antigen Retrieval Citra Solution (Biogenex) at 121° C. for 10 min. The samples were then treated with 3% $H_2O_2$-methanol and sequentially subjected to incubation with Ultra V Block (Lab Vision Corporation) for 10 min and incubation with a polyclonal anti-IGF-II antibody (MBS551011, MyBioSource; 1:100), a polyclonal anti-IGF1R beta antibody (#3027, Cell signaling; 1:20), a rabbit monoclonal anti-Nanog (D73G4, Cell signaling; 1:300) and mouse monoclonal anti-PCNA (PC-10, Thermo Scientific; 1:400) for 2 h at room temperature. Detection of the immunostaining was performed using the Super Sensitive Non-Biotin Polymer HRP Detection System (BioGenex), according to the manufacturer's instructions.

(xvi) Statistical Analysis

The Kaplan-Meier method was used to estimate overall or relapse-free survival curves and the log-rank test was performed to test the difference between survival curves. Cut-off values for separations of high/low risk groups were median of risk scores. The multivariable Cox proportional-hazards regression analysis with covariates age, gender, cell type, tumor Size, tumor grade, proliferating cell nuclear antigen (PCNA) as a proliferative marker, IGF-II expression (high vs. low), IGF1R expression (high vs. low), and Nanog expression (high vs. low) was used to evaluate the independent prognostic factors. The quantitative in vitro and in vivo data are presented as the mean±standard deviation (S.D.) unless otherwise noted. Student's t-tests were used in two group comparison. One-way or two-way analysis of variance (ANOVA) methods with Tukey's post hoc correlations were used for multiple groups comparisons. All tests were two-tailed and P values <0.05 were considered significant.

Results
(i) CAFs from Primary Lung Tumors Support Lung CSC Growth

To investigate whether CAFs from NSCLC patients (see Table 2 below) could provide the niche for cancer stemness, CAFs from tumor tissues were cultured as feeders to examine stemness characteristics in A549 and EKVX lung cell lines and primary lung cancer cells (CL25, CL83, CL141, and CL152; FIG. 1).

TABLE 2

Patient demographics, tumor stage, pathological diagnosis

| Patients | Age | Sex | TNM | Stage | Histology | Primary cultured Cell |
|---|---|---|---|---|---|---|
| PT013 | 54 | F | T1bN0 | Stage IA | ADC | Cancer cell and CAFs |
| PT207 | 67 | M | T4N | Stage IV | ADC | Cancer cell and CAFs |
| PT220 | 71 | M | T3N3M1b | Stage IV | SCLC | Cancer cell and CAFs |
| PT270 | 63 | M | T3N3M1a | Stage IV | ADC | Cancer cell and CAFs |
| PT281 | 72 | M | T2bN0 | Stage IIA | ADC | CAFs and NFs |
| PT290 | 84 | M | T3N0 | Stage IIB | SCC | Cancer cell and CAFs |
| PT337 | 87 | F | T2aN0 | Stage IB | ADC | CAFs and NFs |
| PT376 | 84 | M | T4N0 | Stage IIIB | SCC | CAFs and NFs |
| PT450 | 46 | M | T4N3M1b | Stage IV | ADC | Cancer cell and CAFs |
| PT704 | 47 | F | T2aN0 | Stage IIA | ADC | CAFs and NFs |
| PT881 | 49 | M | T3N0 | Stage IIB | SCC | CAFs and NFs |
| CLS1 | 87 | M | T2bN0 | Stage IIIA | ASC | Cancer cell and CAFs |

ASC: Adenosquamous carcinoma; ADC: Adenocarcinoma; SCC: Squamous cell carcinoma; SCLC: Small cell lung cancer.

The results showed that CAFs outperformed the paired normal fibroblasts (NFs) in terms of their ability to promote sphere-forming activity (FIG. 1a). Moreover, these spheres were isolated through laser-capture via Laser-Enabled Analysis and Processing (EAP), which efficiently purified lung CSC colonies from the co-culture of CLS1/CAF. The purified spheres showed higher expression levels of the stemness markers Oct3/4 and Nanog when co-cultured with CAFs but not NFs (FIG. 1b). The CAF-co-cultured cancer cells also showed higher immunostaining for the stemness marker Nanog (FIG. 1c). PKH26-retaining cells were only observed in cancer cells co-cultured with CAFs (FIG. 1d). Further, FIGS. 1e and f show that the sphere-forming ability and expression of Nanog in cancer cells enhanced by CAFs were not only observed in cancer cell lines but also in primary lung cancer cells (CL25, CL83, CL141 and CL152) derived from lung adenocarcinoma patients.

(ii) Establish Lung CSC Cell Line Using CAFs as Feeder Cells

Conventional in vitro techniques used for cancer cell isolation have limitations because they cannot enrich and maintain CSCs. To overcome these limitations, CAFs isolated from a lung tumor tissue were used as feeder cells to support CSCs in vitro. These primary lung cancer cells formed spheres when co-cultured with CAFs, a sphere-forming lung CSC line, CLS1, was established. As shown in FIG. 1g, a single CLS1 cell formed a sphere within 10 days of sub-culturing with CAFs, showing high expression levels of Nanog, Sox2 and Oct3/4 (FIG. 1g, h), and demonstrated aneuploidy. In contrast, CAFs displaying a normal karyotype were identified as CD90 positive (FIG. 1h) and expressed the myofibroblast markers α-SMA and HLA-a, b and c. The CLS1 cells were cloned by limited dilution and sub-cultured with CAF feeders for further study. Flow cytometric analysis of fibroblast surface markers defined the phenotype of CAF feeder cells. These CAFs were positively stained with human fibroblast specific CD90, HLA-A, HLA-B, and HLA-C(class I), and miofibroblast α-SMA. FIG. 1I.

Figure 9:
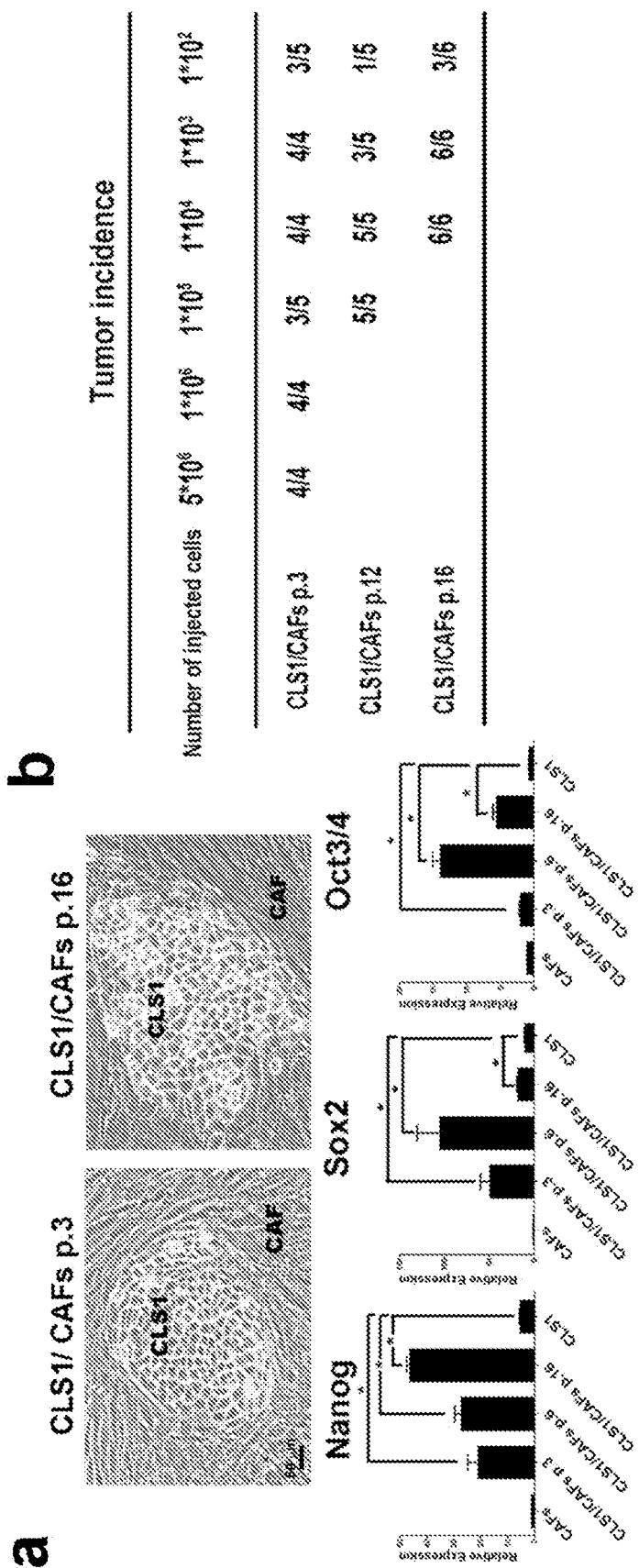
FIG. 9 includes diagrams showing that CAFs co-culture system can be a platform for maintaining lung cancer stemness. (a) Lung CSCs (CLS1) co-cultured with CAFs for 10 days formed similar morphology tumorous spheres in different time point (upper). RT Q-PCR analysis of the stem cell markers Nanog and Oct3/4 in CLS1 cells co-cultured with CAFs (CLS1/CAF) in different passages (CLS1/CAF p.3, CLS1/CAF p.6, and CLS1/CAF p.16) (lower), comparing to CAFs and differentiated CLS1 cells. (N=3) (b) The incidence of mouse xenograft tumors from CLS1/CAF co-cultures in different passage (CLS1/CAF p.3, CLS1/CAF p.12, and CLS1/CAF p.16) (N=4-6 mice) in different cell numbers ($5 \times 10^6$, $1 \times 10^6$, $1 \times 10^5$, $1 \times 10^4$, $1 \times 10^3$, and $1 \times 10^2$ cells) injected subcutaneously into SCID mice. Data represent the mean±S.D. and tested for significance by Student's t-test *$P<0.05$. Data are representative of three independent biological experiments each.

Using CAFs as feeder cells, the CLS1 cells were sub-cultured and maintained their sphere-forming ability with high expression levels of Nanog and Oct3/4 (FIG. 9a), indicating characteristics of cancer cell stemness. To further assess the cancer stemness of CLS1 cells in vivo, a limited dilution of cancer cells was injected into immunodeficient mice as described in Visvader, et al., *Nat Rev Cancer* 8, 755-768 (2008). These results showed that as few as 100 CLS1 cells co-cultured with CAFs could generate xenograft tumors in NOD-SCID mice, and such tumor-initiating ability was maintained after several passages with CAF feeders (FIG. 9b).

(iii) Removal of CAFs from the Co-Culture Reduced the Stemness

Figure 2:
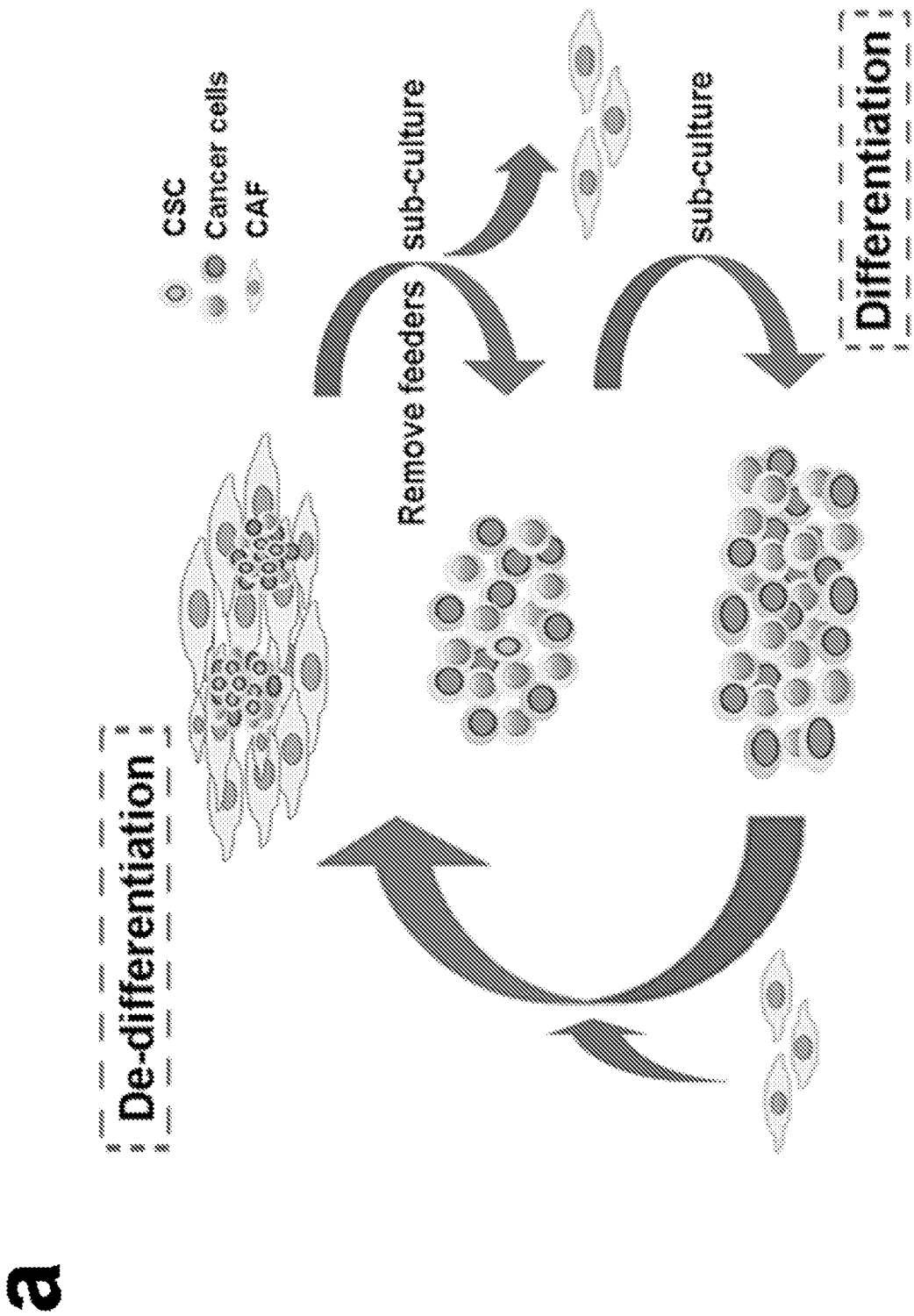
FIG. 2 include diagrams showing lung CSCs (CLS1) maintain cancer stemness and high tumorigenicity when co-cultured with CAF feeders, and lung CSCs differentiate into less tumorigenic cancer cells when cultured without CAF feeders. (a): a schematic illustration showing that differentiated cancer cells would lose their cancer stemness after CAF removal. (b): a diagrams showing RT Q-PCR analysis, which confirmed that the stemness markers Nanog and Oct3/4 were significantly reduced in CLS1 cells following passages without CAFs (from P1 to P14). The data represent the mean±S.D. (N=3), and the different passages of CLS1 cells with CLS1/CAFs were tested by one-way ANOVA with Tukey's post hoc corrections. The data are representative of three independent biological experiments. (c): photos showing immunofluorescence of Oct3/4 in CLS1 cells cultured with (CLS1/CAF) or without CAFs (CLS1) for 5 days. The arrowhead shows glandular-type CLS1 cells that lost Oct3/4 staining after CAF removal. The nuclei were stained with DAPI. Retention assay of PKH26—positively stained cells among CLS1 cells. The cells were pre-stained with the PKH26 red fluorescent dye, and the cells were then co-cultured with or without CAFs for 1 week. Arrows mark the CLS1 cells that retained PKH26 fluorescence. Scale bar, 50 μm. (d): photos showing spontaneous lung metastatic nodules of CLS1/CAF (N=15 mice) and CLS1 (N=10 mice) xenograft tumors (upper), which were stained with H&E (bottom). Scale bar, 100 μm. (e): photos showing IHC analysis for Oct3/4 and Nanog expression in a xenograft tumor (subcutaneous and spontaneous lung metastasis tumor) derived from injection of a CLS1 sphere co-cultured with CAFs. Scale bar, 50 μm.
Figure 2:
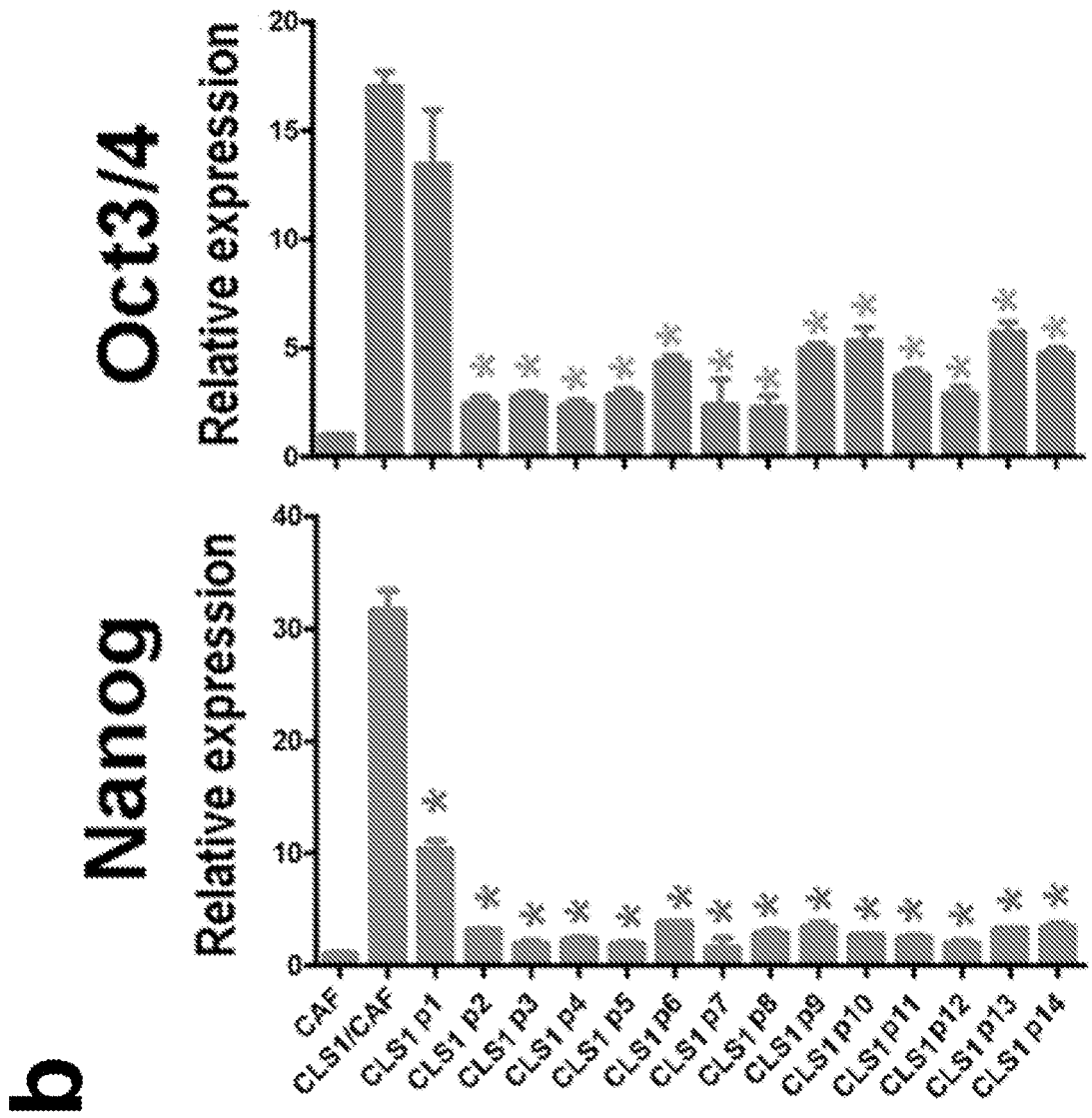
Figure 2:
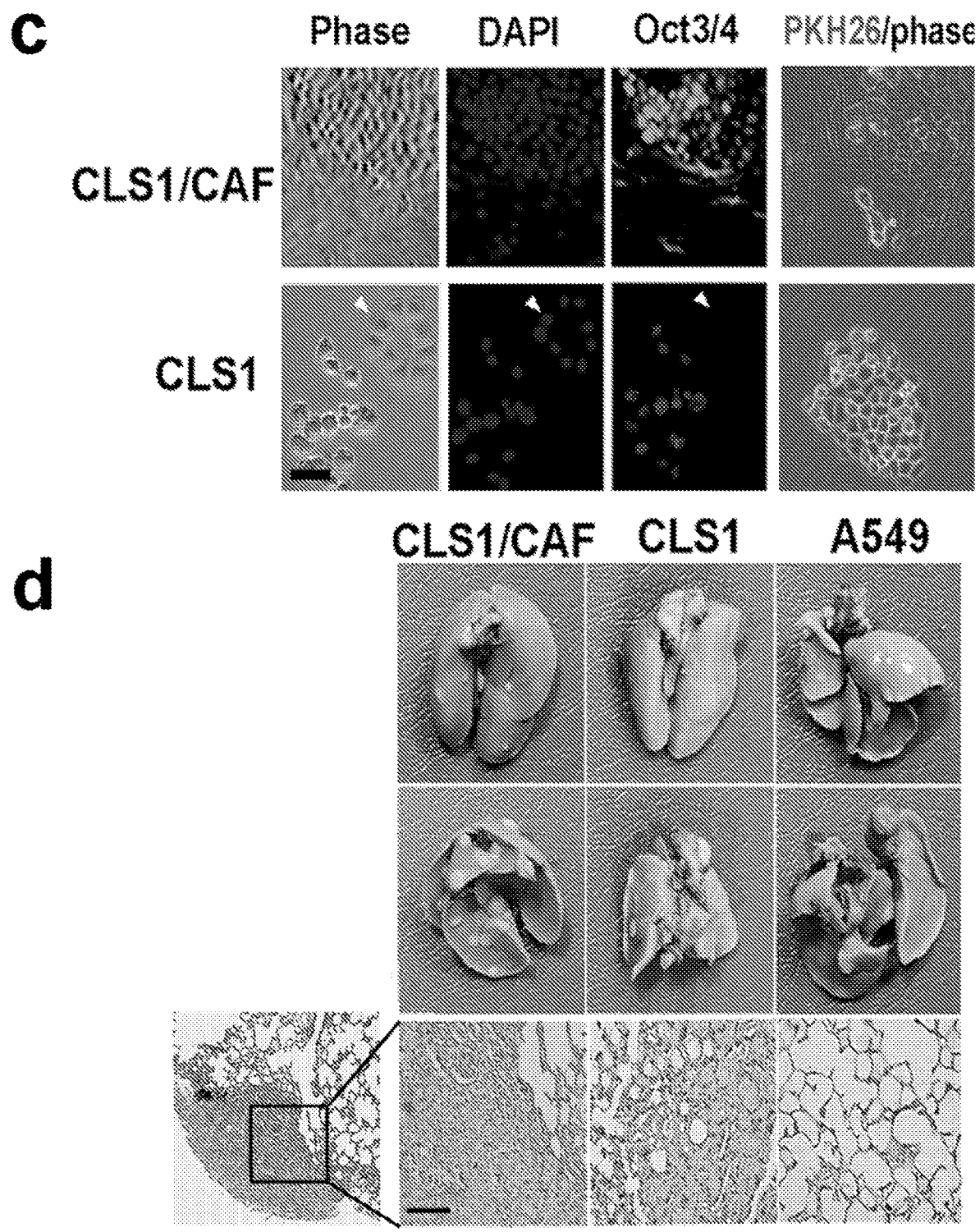
Figure 2:
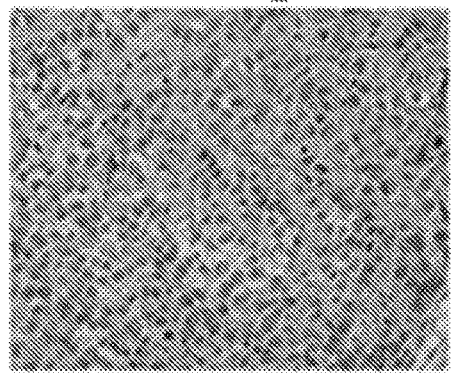
Figure 2:
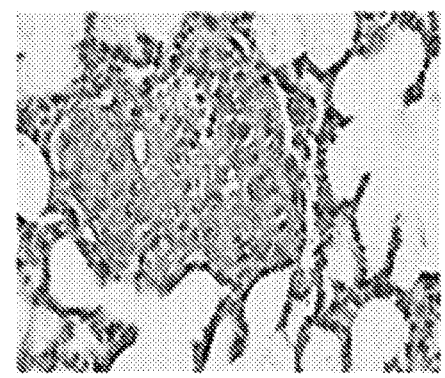
Figure 2:
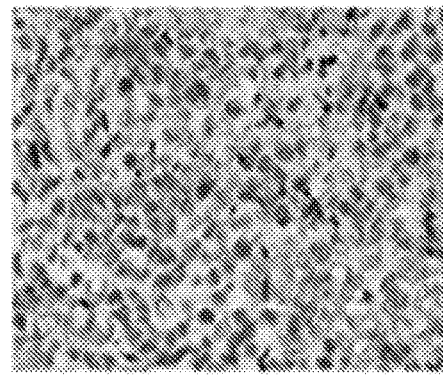
Figure 2:
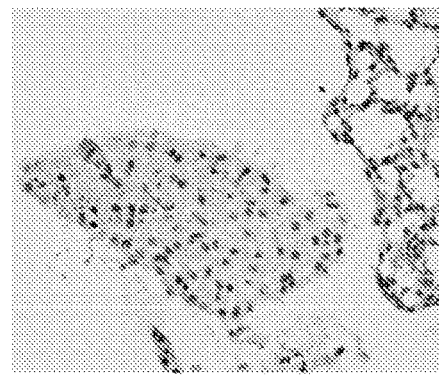
Figure 2:
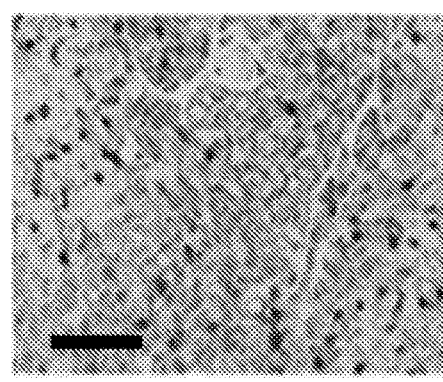
Figure 2:
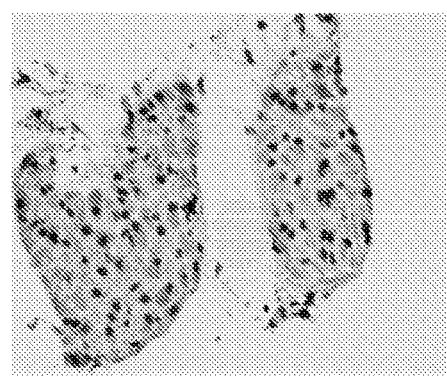

CAF-co-cultured CLS1 cells (CLS1/CAF) maintained their cancer stemness phenotype; however, when CAFs were removed during passaging, such cancer stemness characteristics were lost, followed by the down-regulation of Oct3/4 and Nanog (FIG. 2a, b) as well as a reduction in Oct3/4-positive cells and PKH26-retaining cells (FIG. 2c). Most importantly, the data showed that the tumor-initiating frequency of CLS1/CAF was 1/910, and these cells demonstrated highly metastatic activity (12/15), whereas the tumor-initiating capacity and metastatic ability of CLS1 cells was decreased (1/4,137) after 12 passages without CAFs (see Tables 3 and 4 below).

TABLE 3

TICs Frequency of Cancer cells/CAFs and Differentiated cancer cells.

| Cells | No. cells per injection | No. tumor/No. injections | TICs frequency (95% CI) |
|---|---|---|---|
| CLS1/CAFs | 100 | 10/26 | 1/910 |
|  | 1000 | 16/21 | (1/552-1/1498) |
|  | 10,000 | 20/21 |  |
| CLS1 p.12 | 100 | 0/11 | 1/4137 |
|  | 1000 | 5/11 | (1/2145-1/7979) |
|  | 10,000 | 9/11 |  |
|  | 100,000 | 9/11 |  |
| CL141/CAFs | 100 | 2/6 | 1/670 |
|  | 1000 | 4/6 | (1/271-1/1652) |
|  | 10,000 | 6/6 |  |
| CL141 p.6 | 100 | 0/6 | 1/61,464 |
|  | 1000 | 0/6 | (1/8,704-1/434,022) |
|  | 10,000 | 1/6 |  |
| CL152/CAFs | 100 | 1/6 | 1/9,702 |
|  | 1000 | 1/6 | (1/3,721-1/25,293) |
|  | 10,000 | 3/6 |  |
| CL152 p.6 | 100 | 0/6 | N.D |
|  | 1000 | 0/6 |  |
|  | 10,000 | 0/6 |  |

TABLE 3-continued

TICs Frequency of Cancer cells/CAFs and Differentiated cancer cells.

| Cells | No. cells per injection | No. tumor/No. injections | TICs frequency (95% CI) |
|---|---|---|---|
| A549 | 100 | 0/5 | 1/4244,670 |
|  | 1000 | 0/9 | (1/109,505-1/546,672) |
|  | 10,000 | 1/9 |  |
|  | 100,000 | 2/9 |  |

The tumor-initiating frequency of CSCs (TIFC) was calculated using the L-calc limiting dilution analysis software. CI, confidence interval; N.D., not determined.

TABLE 4

The Metastasis Incidence of CLS1/CAFs, CLS1 and A549 cells

| Cells | Lung metastasis/Mice |
|---|---|
| CLS1/CAFs | 12/15 |
| CLS1 | 2/10 |
| A549 | 0/3 |

The xenograft tumors showed strong Oct3/4 and Nanog staining in cells at subcutaneous and metastatic sites (FIG. 2e). Moreover, these subcutaneous and metastatic lung tumors could be re-cultured, and the primary cultured lung cancer cells from metastatic sites showed a tumorous, spherical phenotype similar to the original CLS1 cells. Repeatedly cultured cancer cells showed the same tumorigenic ability as parental CLS1 cells and formed xenograft tumors in mice at a low cell number (100 cells). See Table 5 below.

TABLE 5

Tumor incidence/Number of Injected Mice

| Number of Injected Cells | $1 \times 10^4$ | $1 \times 10^3$ | $1 \times 10^2$ |
|---|---|---|---|
| Meta lung-tomor | 4/4 | 4/4 | 3/5 |
| SC xenograft | 4/4 | 4/4 | 2/5 |

Co-culture of CAFs with primary lung cancer cells (CL141 and CL152) as well as CLS1 cells can increase sphere-forming ability, larger sphere size and increased tumor-initiating frequency in xenografts compared to cancer cells sub-cultured without CAFs for an additional 3 passages (FIG. 2d). ALDH activity was also reduced after removing CAFs from the co-culture. These results indicated that CAFs act as the key regulator of cancer stemness in primary lung cancer cells.

Assessment of the cellular SP is another method for evaluating cancer stemness ability and drug resistance. CLS1 cells co-cultured with CAFs demonstrated a higher percentage of SP cells compared to other lung cancer cell lines, including CL1-5, A549, H522, H23, Hop62, H322M and EKVX. The SP % of cell lines CL1-5 (adenocarcinoma), A549 (adenocarcinoma), H522 (adenocarcinoma), H23 (adenocarcinoma), Hop62 (adenocarcinoma), H322M (bronchi alveolar carcinoma), and EKVX (adenocarcinoma) are ND, 5.1, 0.2. ND, ND, ND, and 9.6, respectively. The SP of CLS1 cells was significantly reduced after CAF removal (FIG. 10d), and resistance to chemotherapeutic drugs (etoposide, docetaxel, vinorelbine ditartrate and cisplatin) was decreased (Table 6).

TABLE 6

The $IC_{50}$ of CLS1/CAF and CLS1 treated with chemotherapeutic compounds

| Drugs | $IC_{50}$ CLS1/CAF | CLS1 |
|---|---|---|
| Etoposide (VP-16) | 109.47 µM | 1.06 µM |
| Docetaxel | 54.8 nM | 4.2 nM |
| Vinorelbine ditartrate | 775.4 nM | 28.5 nM |
| Cisplatin | 0.31 µM | 0.20 µM |

F Removal Leads to "Differentiation" of CLS1 Lung CSCs

Figure 10:
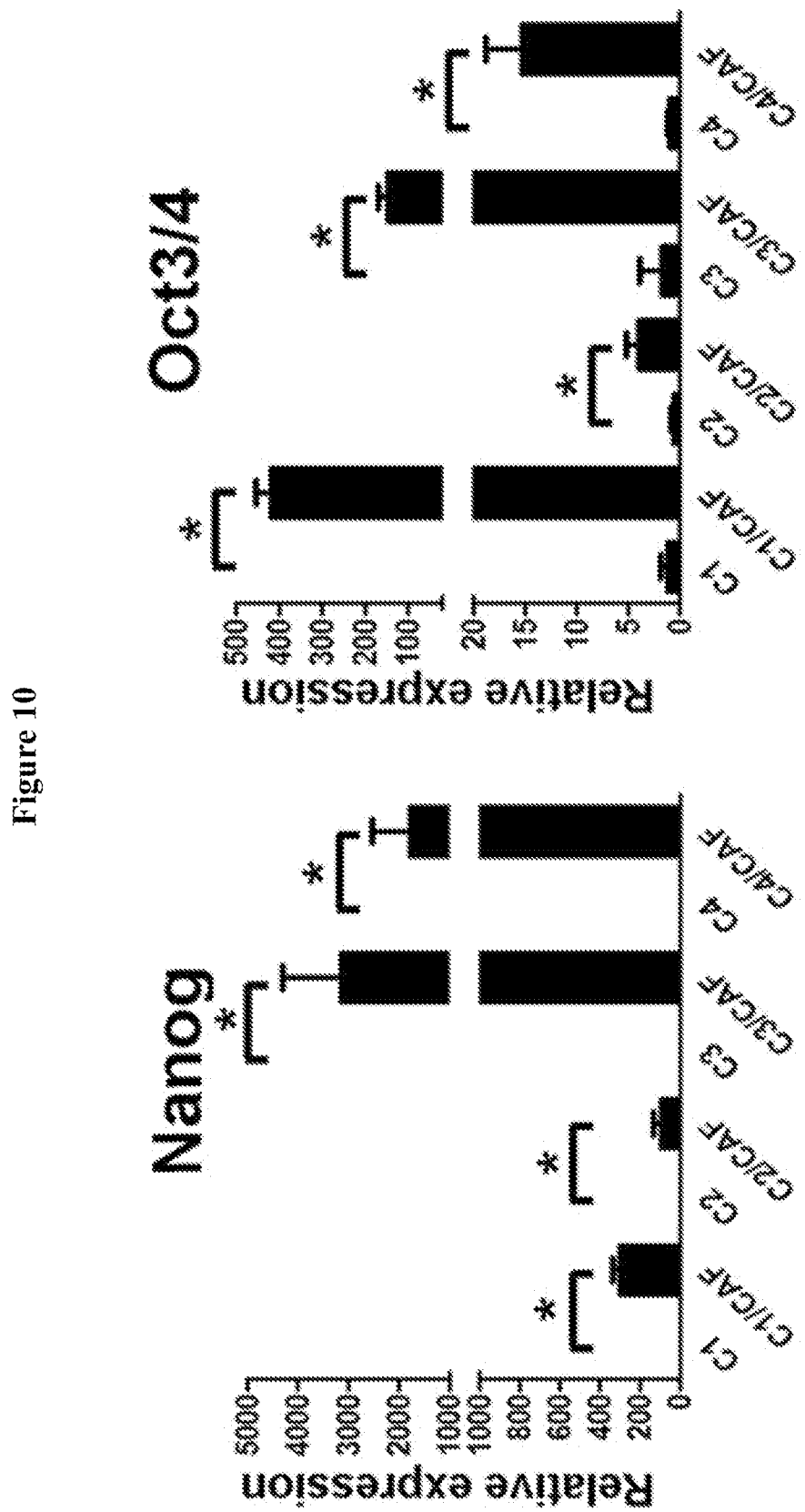
FIG. 10 includes charts showing that differentiated CLS1 can de-differentiate through re-co-culturing with CAFs. RT Q-PCR analysis of the stem cell markers Nanog and Oct3/4 in different clones of tumor cells (C1, C2, C3, and C4) co-cultured with CAFs (CLS1/CAF), comparing to different clones of tumor cells. (N=3) Data represent the mean±S.D. and tested for significance by Student's t-test *$P<0.05$. Data are representative of at least three independent biological experiments each.

CLS1 cells co-cultured with CAFs (CLS1/CAF) maintained their cancer stemness phenotype. However, CLS1 cells became anchorage-dependent and showed reduced Nanog and Oct3/4 expression after removal of the feeder cells. Some CLS1 cells even showed glandular differentiation concurrent with the loss of Oct3/4 (FIG. 2c, arrow head) and different expression patterns of adenocarcinoma and squamous carcinoma markers (TTF1, CK7, CK20, p63 and keratin 5/6 for squamous cell carcinoma) in different CLS1 single-cell clones (C1, 2, 3 and 4 clones). Immunohistochemistry (IHC) also showed differentiated cancer cells with different staining patterns (TTF1, CK7, CK20, p63, keratin 5/6, and mucin-1) in CLS1-formed xenografts. These results indicated that CLS1 cells with stemness characteristics could be differentiated into different types of lung cancer cells expressing different adenocarcinoma and squamous cell carcinoma markers. Importantly, this pattern could be reversed by re-co-culturing with CAFs, leading to a down-regulation of differentiation markers and a significant up-regulation of Nanog and Oct3/4 (FIG. 10).

(v) CAFs Promote Stem-Cell-Like Properties in Lung Cancer Cells

Figure 3:
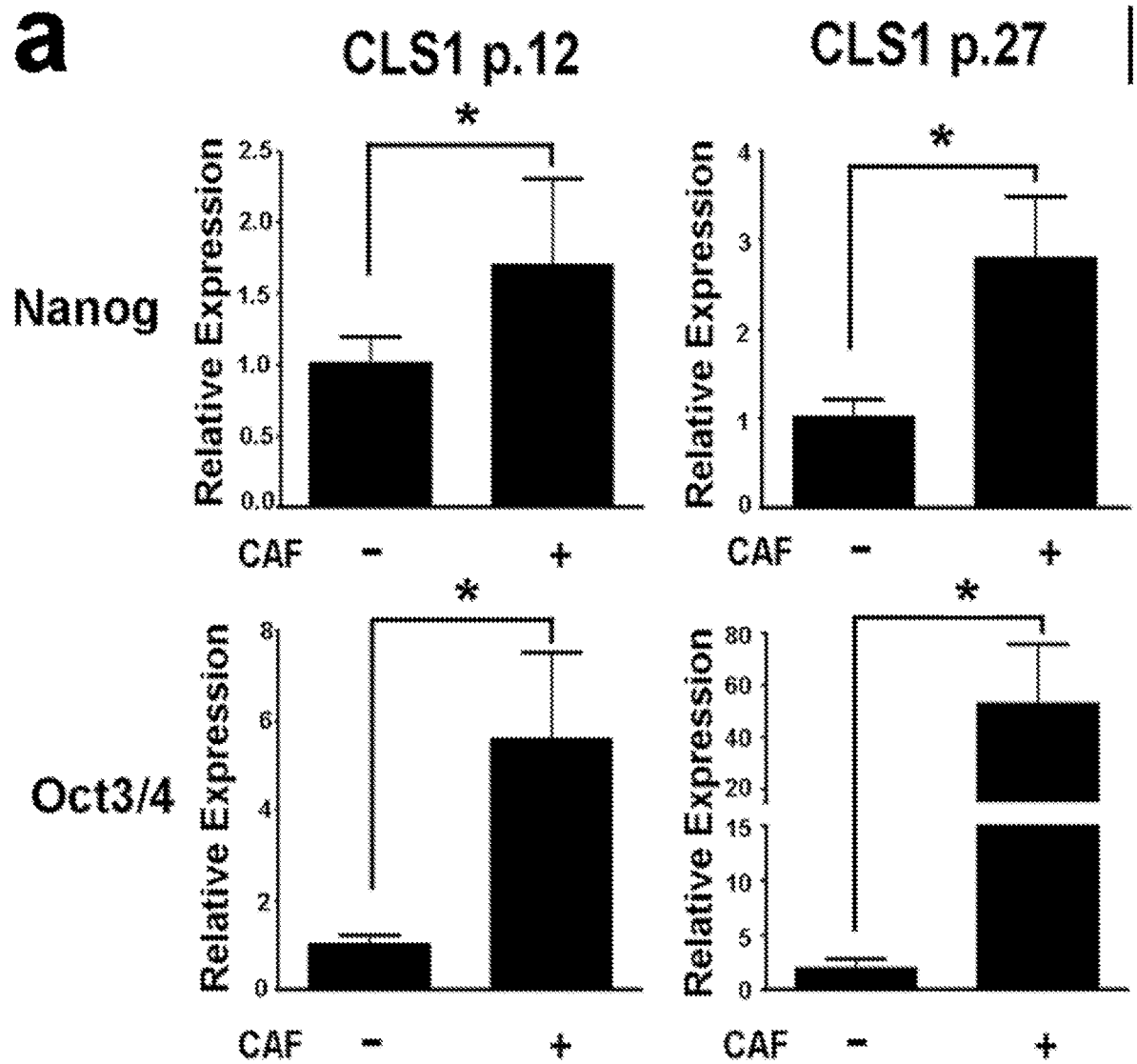
FIG. 3 include diagrams showing differentiated lung cancer cells can de-differentiate and re-acquire stem-cell-like properties through re-co-culturing with CAFs. (a): charts showing RT Q-PCR analysis which was performed to assess expression of the stemness markers Nanog and Oct3/4 in CLS1 p.12 and CLS1 p.27 cells cultured with or without CAFs (N=3). (b): photos and charts showing the incidence of mouse xenograft tumors from CLS1/CAF co-cultures (N=6 mice), differentiated CLS1 cells after 12 and 27 passages (p6 and p12; N=6 mice), A549 and CLS1 p.12/CAFs, CLS1 p.27/CAFs and A549/CAFs (N=6 mice), which was determined following the subcutaneous injection of different cell numbers ($1 \times 10^4$, $1 \times 10^3$ and $1 \times 10^2$ cells) into SCID mice. Scale bar, 200 μm. (c): a chart showing the incidence of mouse xenograft tumors derived from sorted ALDH- CLS1 cells after 3 passages (p3; N=6 mice) and ALDH- CLS1/CAFs (N=6 mice) following subcutaneous injection into SCID mice at different cell numbers ($1 \times 10^4$, $1 \times 10^3$ and $1 \times 10^2$ cells). (d): charts showing RT Q-PCR analysis, which was performed to assess expression of the stemness markers Nanog and Oct3/4 in ALDH- CLS1 cells cultured with or without CAFs (N=3). (e): diagrams showing the ALDH activity of ALDH- CLS1 cells cultured with or without CAFs. ALDH activity, which was evaluated by staining with the ALDEFLUOR dye in the absence (upper) or presence (lower) of DEAB (an ALDH inhibitor) for 30 min at 37° C. and analyzed by flow cytometry. The data represent the mean±S.D. and difference were tested by the Student's t-test *P<0.05. The data are representative of at least three independent biological experiments.
Figure 3:
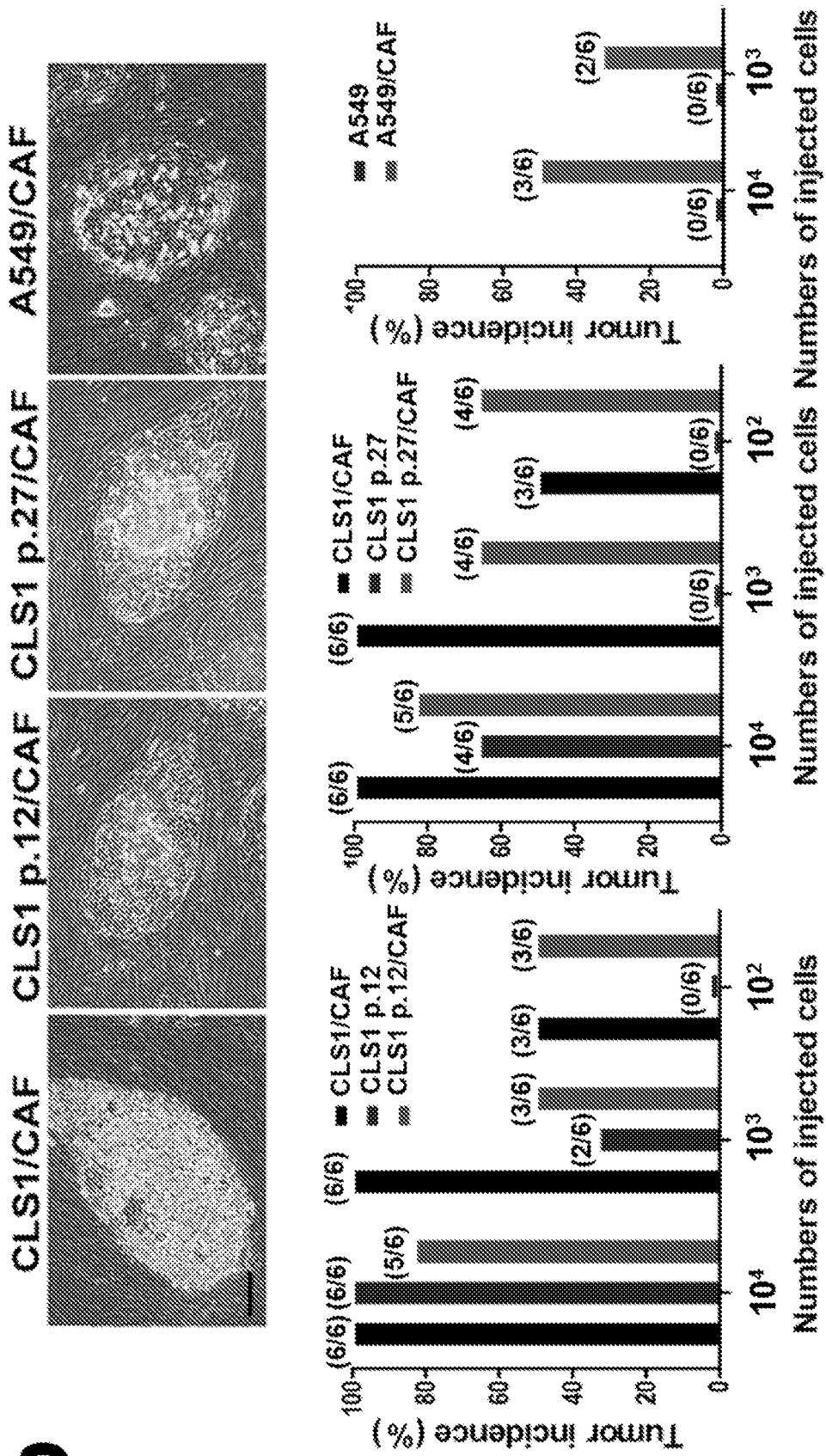
Figure 3:
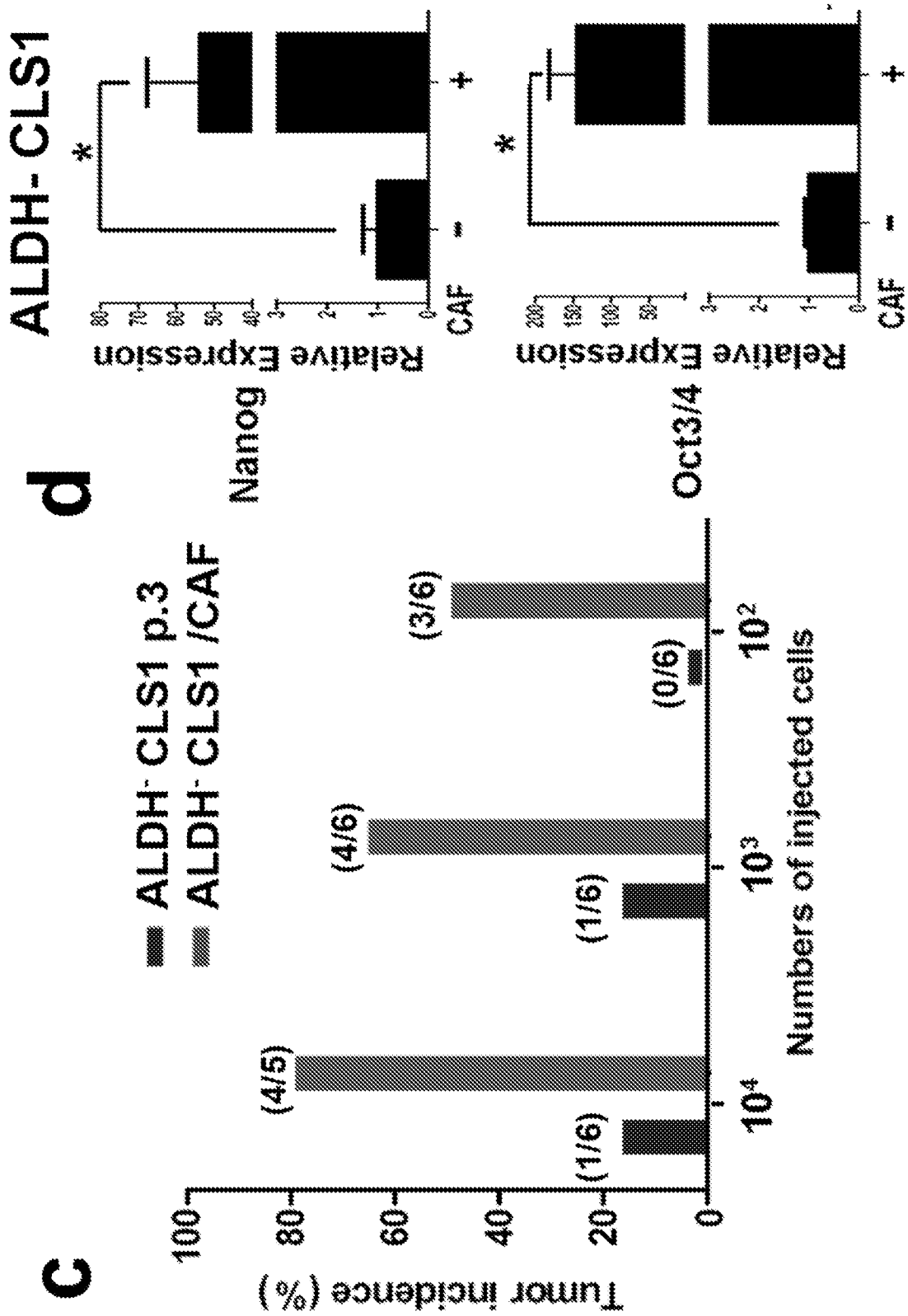
Figure 3:
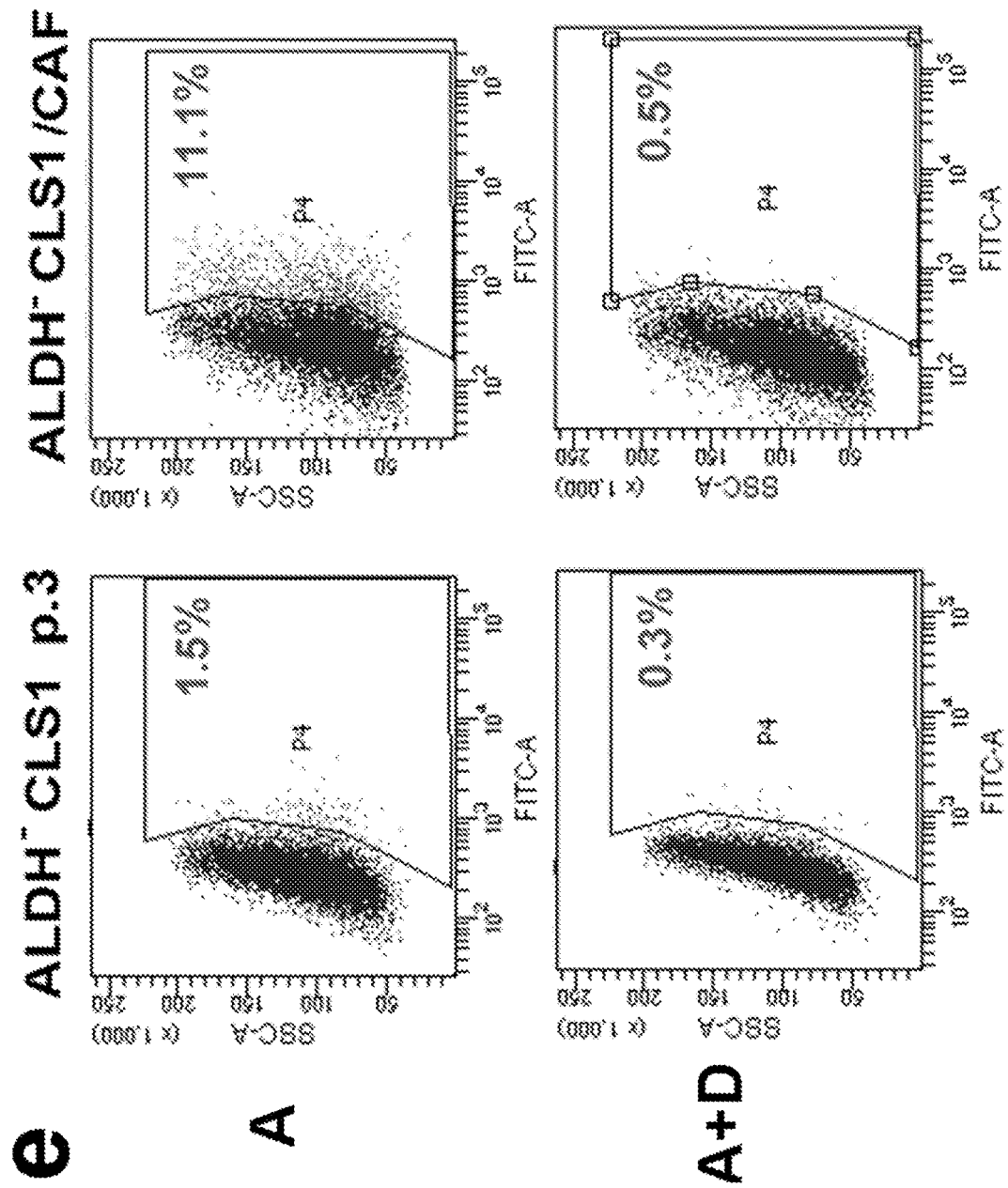

As noted above, removal of CAFs led to differentiation and loss of stemness characteristics among lung CSCs and the differentiated cancer cells (CLS1 p12, CLS1 p27 and A549 cells) could be de-differentiated by re-co-culturing with CAFs to regain cancer stem-like properties, with an increased expression of stemness markers (Nanog and Oct3/4; FIG. 3a) as well as the ability to form xenografts after the intradermal administration of as few as 100 cells (FIG. 3b). These data further support that differentiated lung cancer cells could be induced to "de-differentiate."

Next, CLS1 cells with negative ALDH activity (ALDH−) were sorted as the differentiated (non-CSC) population; then, these ALDH− CLS1 cells were co-cultured with CAFs to determine whether CAFs have the ability to promote tumorigenesis via an increase in cancer stemness. The results showed that the ALDH− population had very low tumorigenic ability in a xenograft model (FIG. 3c). Interestingly, these ALDH− CLS1 cells regained a high tumorigenic ability after re-co-culturing with CAFs; in particular, their cancer stemness properties were re-activated, and their expression of stemness markers increased (Nanog and Oct3/4 increased 53.8- and 145.3-fold, respectively; ALDH activity increased 8.83-fold; tumor-initiating frequency increased from 1/7,917 to 1/91; FIG. 3c-e).

These results suggest that the Oct3/4(+) and Nanog(+) CSC population can be maintained by CAF feeders but is reduced after CAF removal, and this population can also be re-programmed to regain stemness after re-co-culturing with CAFs (FIG. 2a). This CSC/CAF co-culture system therefore represents a good model to study how the microenvironment impacts CSCs, particularly how the differentiation of tumorigenic CSCs into less tumorigenic cancer cells is affected by the tumor microenvironment. Magee, et al., Cancer Cell 21, 283-296 (2012).

(vi) Transcriptomic Profiling Reveals a Stemness Pathway in CSCs

Figure 11:
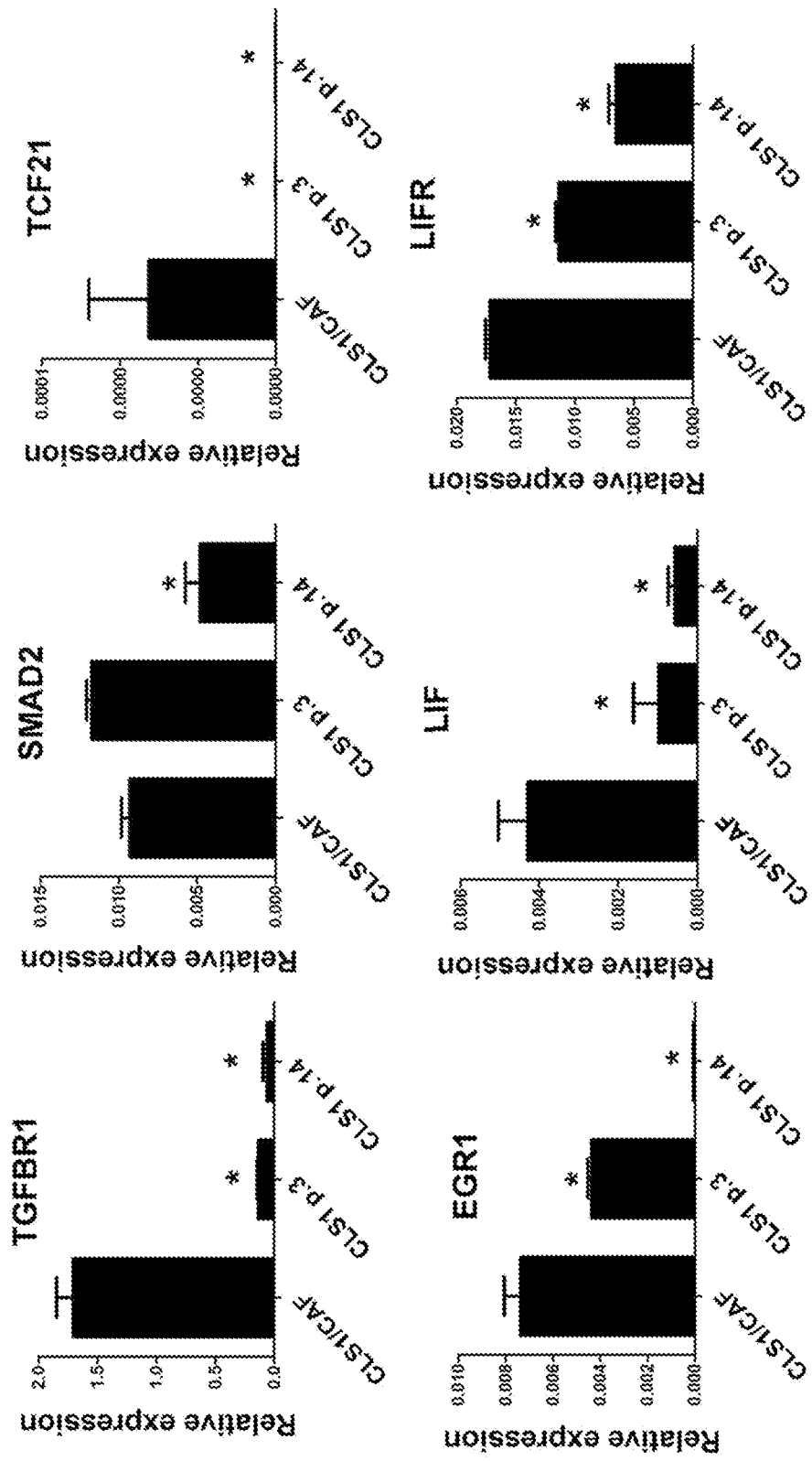
FIG. 11 includes charts showing key signaling pathways in CSCs as revealed by full genome gene expression profiling. Real-time RT Q-PCR analysis of TGF beta-related pathway molecules (TGFBR1 and SMAD2), a Wnt-related pathway molecule (TCF21), a EGFR-related pathway molecule (EGR1), and LIF-related pathway molecules (LIF and LIFR) in the CLS1/CAF co-culture for 10 days and after serial passages (p3 and p14) of CLS1 cells cultured in the absence of CAFs. Data represent the mean±S.D. and tested for significance by Student's t-test *$P<0.05$. Data are representative of three independent biological experiments each.

To discover cancer stemness-specific signaling pathways in lung CSCs, the gene expression profile of Oct3/4(+)/Nanog(+) CLS1 CSCs (CLS1/CAF) was analyzed and compared this profile with that of CLS1-differentiated cancer cells cultured without feeder cells through different passages (CLS1 p3, p6 and p12). According to the transcriptome and MetaCore software analysis, stemness pathways related to insulin-like growth factor 1 receptor (IGF1R), epithelial-mesenchymal transition (EMT), phosphatidylinositol 3-kinase (PI3K), TGF-β, WNT, and Hedgehog pathways, which regulate several stemness transcriptional factors (Oct3/4, Nanog and Sox2), were up-regulated in the CLS1/CAF co-culture, whereas dramatically reduced following serial passage without CAFs. Some of the pathways identified in these CLS1/CAF co-cultures, such as EMT, TGF-β and Hedgehog signaling, have been reported to be involved in maintaining cancer stemness. Chang, et al. Nat Cell Biol 13, 317-323 (2011); Mani, et al. Cell 133, 704-715 (2008); and Zhao, et al. Nature 458, 776-779 (2009). For instance, EMT regulated by multiple epigenetic mechanisms is known to repress the expression of epithelial markers and to convert epithelial cells into aggressive, invasive tumor cells with stem cell properties. Chang et al., 2011. These results indicated the presence of a complicated regulatory network for maintaining cancer stemness in lung CSCs. Some of the key regulators identified, including transforming growth factor receptor 1 (TGFBR1), transcription factor 21 (TCF21), leukemia inhibitory factor (LIF), leukemia inhibitory factor receptor (LIFR), early growth response 1 (EGR1) and SMAD2, were validated by Q-PCR, showing a decreasing trend following serial passage without CAFs (FIG. 11). Metacore pathway analysis showed up-regulation of genes involved in the EMT, PI3K, IGF1R, TGF-beta, WNT, and Hedgehog signaling pathways in CLS1/CAF co-cultures. Interestingly, these stemness pathways may be triggered via extracellular signaling, indicating that paracrine and autocrine regulation may contribute to maintaining the CSC population in vivo.

(vii) CAFs Regulate Cancer Stemness Through the Paracrine Network

To better understand how CAFs contribute to maintaining lung cancer stemness, both the transcriptional regulation network and the cytokine network in/between CAF and CLS1 cells were studied. Interestingly, CAFs highly express several growth factors, including IGF-II, hepatocyte growth factor (HGF), LIF and stromal cell-derived factor 1 (SDF1). Conversely, the receptors for these growth factor, including IGF1R, insulin-like growth factor receptor 2 (IGF2R), hepatocyte growth factor receptor (HGFR), LIFR and C-X-C chemokine receptor type 4 (CXCR4), as well as related signaling modulators such as insulin-like growth factor binding proteins (IGFBPs), were highly expressed in CLS1 cells (FIG. 4a, b). This observation suggested the presence of crosstalk and the existence of paracrine regulation between CAF and CLS1 cells. Most importantly, it was found that conditioned medium obtained from the CLS1/CAF co-culture system could significantly up-regulate Nanog expression in CLS1 cells (FIG. 4c). To explore this mechanism of paracrine regulation, the Human Chemokine and Cytokine Antibody Array (Ray Biotech, Inc. Norcross Ga.), including 274 specific antibodies, was used, which demonstrated that a number of cytokines were relatively abundant in the CLS1/CAF co-culture medium (FIG. 4d, e).

Figure 12:
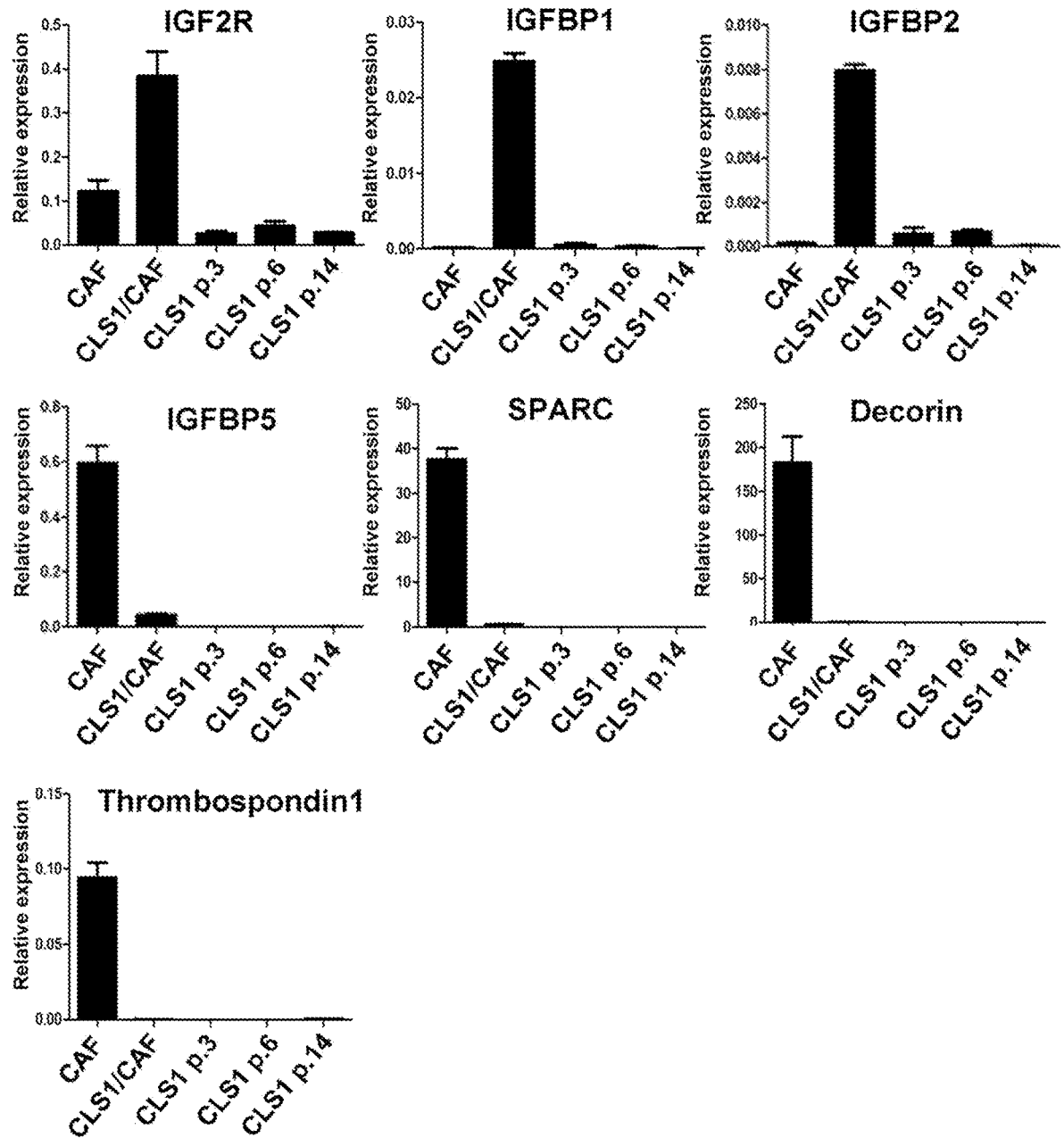
FIG. 12 includes charts showing potential paracrine interactions between CAFs and CLS1 cells validated by real-time RT Q-PCR. Candidate genes involved in paracrine crosstalk between CAFs and CSCs (CLS1), including IGF2R, IGFBP1, IGFBP2, IGFBP5, SPARC, decorin, and thromobospondin-1, were validated by Q-PCR. The CLS1 cells (after passage p3, p6, and p14) were derived from CLS1 spheres dissociated to single cells and then sub-cultured without CAFs. The CAFs served as the feeder cell control. Data represent the mean±S.D. and tested for significance by Student's t-test *$P<0.05$. Data are representative of three independent biological experiments each.

Among these candidate cytokines identified, it was found that IGF-II, soluble CD14, and HGF individually induced Nanog expression in CLS1 cells (FIG. 4f), with IGF-II showing the greatest effect. Interestingly, HGF and soluble CD14 synergistically increased the effects of IGF-II-induced Nanog expression by 20-fold in CLS1 cells (FIG. 4g). Importantly, it was found that IGF did not act as an autocrine factor, as it does in hepatocellular carcinoma. Shan, et al. Hepatology 56, 1004-1014 (2012). Instead, it was showed the paracrine regulation of IGF-II from CAFs acting on the IGF1R dominantly expressed in lung CSCs (CLS1) as well as other IGF-response factors (IGF2R, IGFBP1 and IGFBP2; FIG. 4b and FIG. 12). Immunofluorescence staining further confirmed that IGF1R was abundantly expressed in lung CSCs, whereas IGF-II was predominantly expressed in CAFs (FIG. 4h). In addition, HGFR and CXCR4 mRNAs were expressed in CLS1 cells, whereas HGF and SDF1 were more highly expressed in CAFs (FIG. 4a, b).

Figure 13:
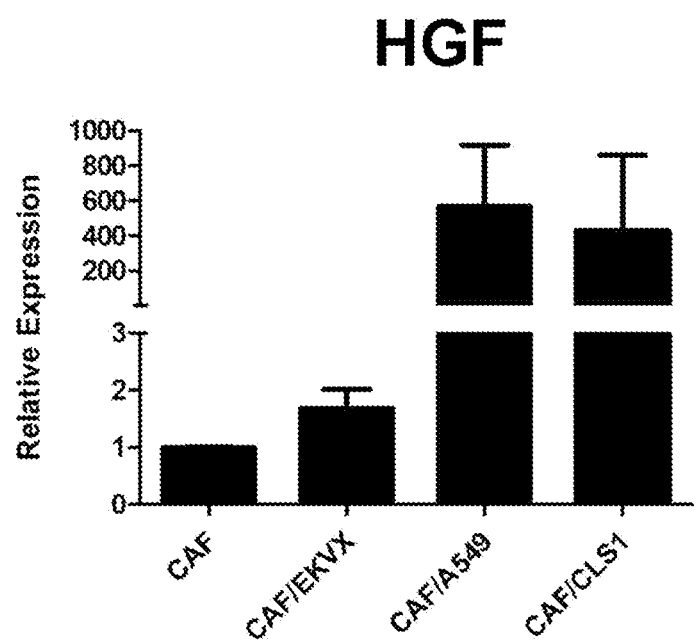
FIG. 13 includes charts showing reciprocal interaction of genes induced in CAFs by co-culture with lung carcinoma cells. RT Q-PCR analysis of HGF and SDF1 in different patient's CAFs (N=5 patients) cultured with or without A549, EKVX and CLS1 cells. Data represent the mean±S.D. and tested for significance by Student's t-test *$P<0.05$. Data are representative of at least three independent biological experiments each.
Figure 13:
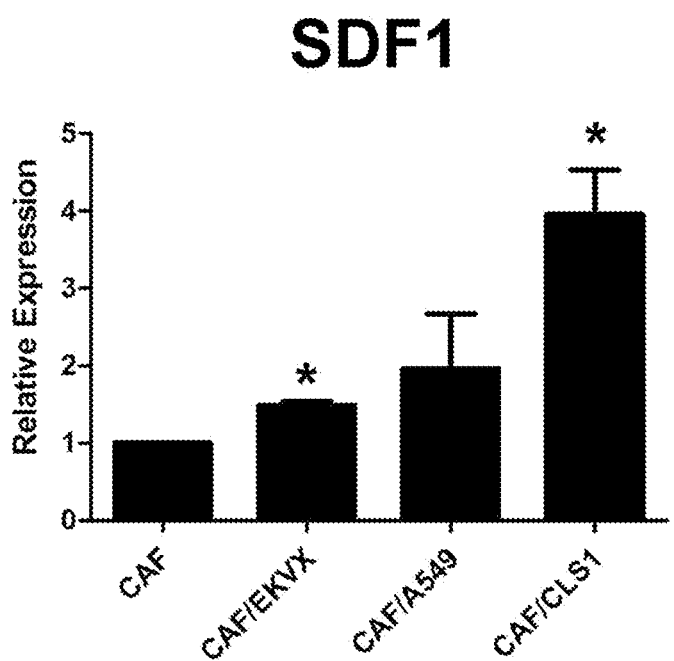

Furthermore, it was suggested that the reciprocal interaction of genes induced in CAFs by co-culture with lung cancer cells is also important in regulating the cancer stemness niche. In fact, it was found that several critical paracrine factors, including IGF-II, HGF and SDF-1, are released from CAFs and may play important roles in maintaining cancer stemness (FIG. 4b). Moreover, these factors could be regulated by co-culture with cancer cells (CLS1, A549 and EKVX cells; FIG. 4i and FIG. 13). Thus, the data suggest that the cancer stemness niche could involve two-way communication between cancer cells and CAFs.

(viii) CAFs Support Stemness Through IGF-II/IGF1R/Nanog Signaling

To further evaluate whether IGF-II could be produced in all tumor-derived CAFs, isolated CAFs from different lung cancer patients were co-cultured with different lung cancer cells. Laser-captured feeder cells from different CAF samples showed higher expression levels of IGF-II (N=6 with A549 cells and N=9 with EKVX cells) (FIG. 4i). Likewise, colony cells from cancer cells cultured with CAFs (N=4) showed higher IGF1R expression levels (FIG. 4j). The characteristics of the 12 CAF samples isolated from patients are shown in Table 2. Without being bound by theory, it was proposed a putative signaling crosstalk model involving paracrine interactions between CAFs and lung CSCs that contribute to cancer stemness (FIG. 4k).

Figure 5:
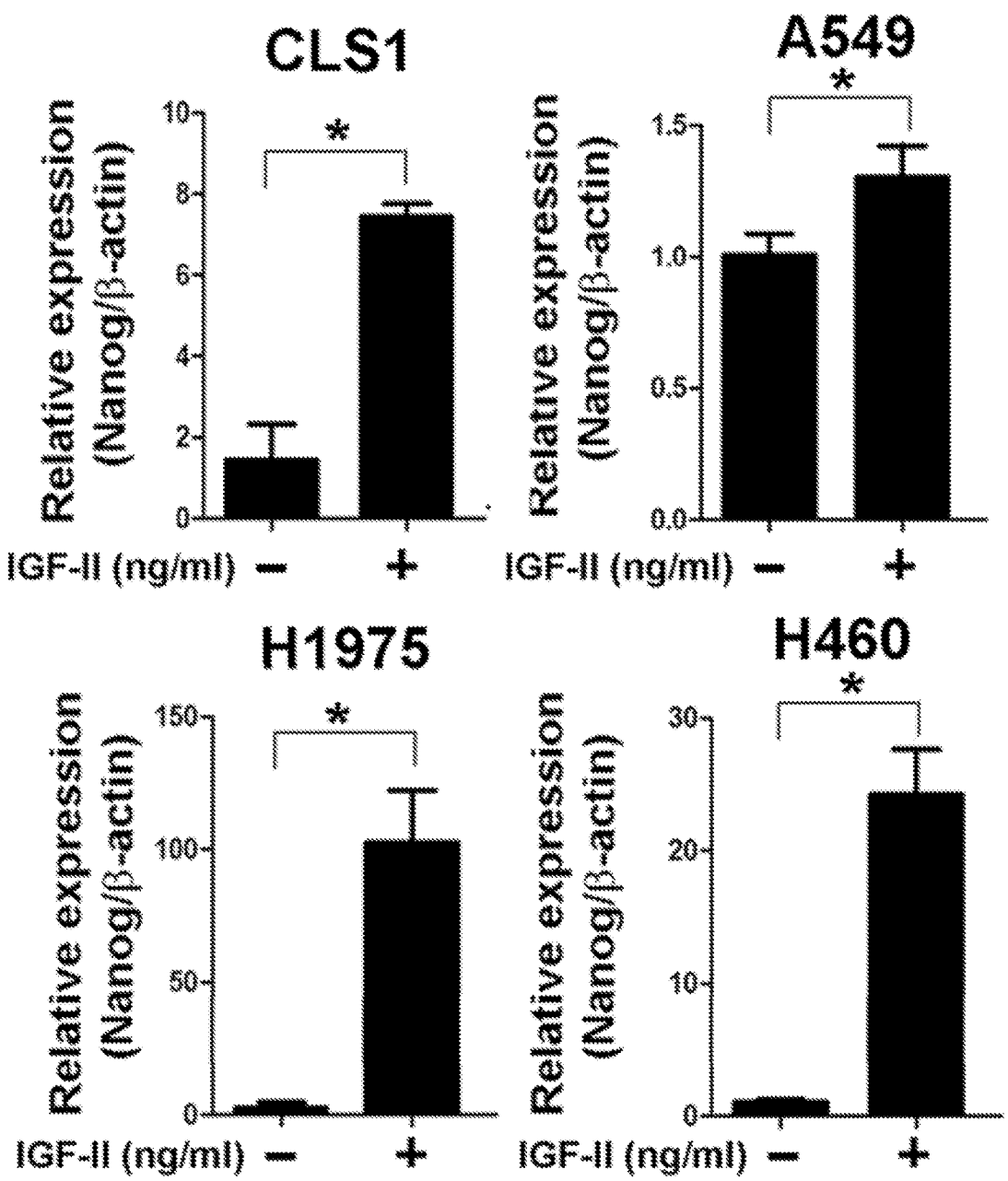
FIG. 5 include diagrams showing that the IGF-II/IGF1R/Nanog pathway is involved in microenvironmental paracrine signaling for maintaining the stemness of lung CSCs. (a): charts showing RT Q-PCR analysis of the stem cell marker Nanog for four different lung cancer cell lines (CLS1, A549, H1975 and H460) treated with IGF-II (100 ng/ml) (N=3). (b): photos and charts showing the sphere-forming ability (lower panel) and morphology (upper panel) of CLS1 cells treated with IGF-II (10 and 100 ng/ml) after culturing in MCDB201 medium with EGF (20 ng/ml) and bFGF (20 ng/ml) for 21 days. Scale bar, 100 μm. (c): photos showing Western blot analysis of IGF1R, AKT and Nanog expression in CLS1 cells treated with IGF-II (10 ng/ml) and in primary cell lines (CL141 and CL152 cells) treated with IGF-II (100 ng/ml) at the indicated time points (0, 10 and 30 min and 1, 2, 6 and 24 h). (d): a photo showing protein levels of Nanog-targeting shRNA Nanog (shN1 and shN2) or scrambled siRNA (shLuc) cells treated with IGF-II (10 ng/ml) for 24 h, which were examined through immunoblotting. β-Actin was used as an internal control. (e): photos and charts showing sphere-forming ability (Numbers of sphere, N=6; Average area of sphere, N=10) and morphology of CLS1 cells treated with IGF-II (10 ng/ml) and analysis of the specific knockdown of Nanog after culturing in MCDB201 medium with EGF (20 ng/ml) and bFGF (20 ng/ml) for 14 days. Scale bar, 50 μm. (f): Photos showing protein levels of Nanog in Nanog-targeted shRNA cells (shN1 and shN2) or scrambled siRNA (shLuc) cells, which were examined through immunoblotting. β-Actin was used as an internal control. Scale bar, 200 μm. (g): a chart showing the incidence of xenograft tumors formed from CLS1/CAF cells with or without shRNA-mediated Nanog knockdown. The tumors were generated by the injection of 1,000 CLS1/CAF cells (N=8 mice). (h): a chart showing the tumor volumes formed by CLS1/CAF cells with or without Nanog knockdown (N=8 mice). The data represent the mean±S.D. and were tested for significance by the Student's t-test (a) or one-way ANOVA with Tukey's post hoc corrections (b-h); *P<0.05. The data are representative of three independent experiments, with three or more replicates in each experiment.
Figure 5:
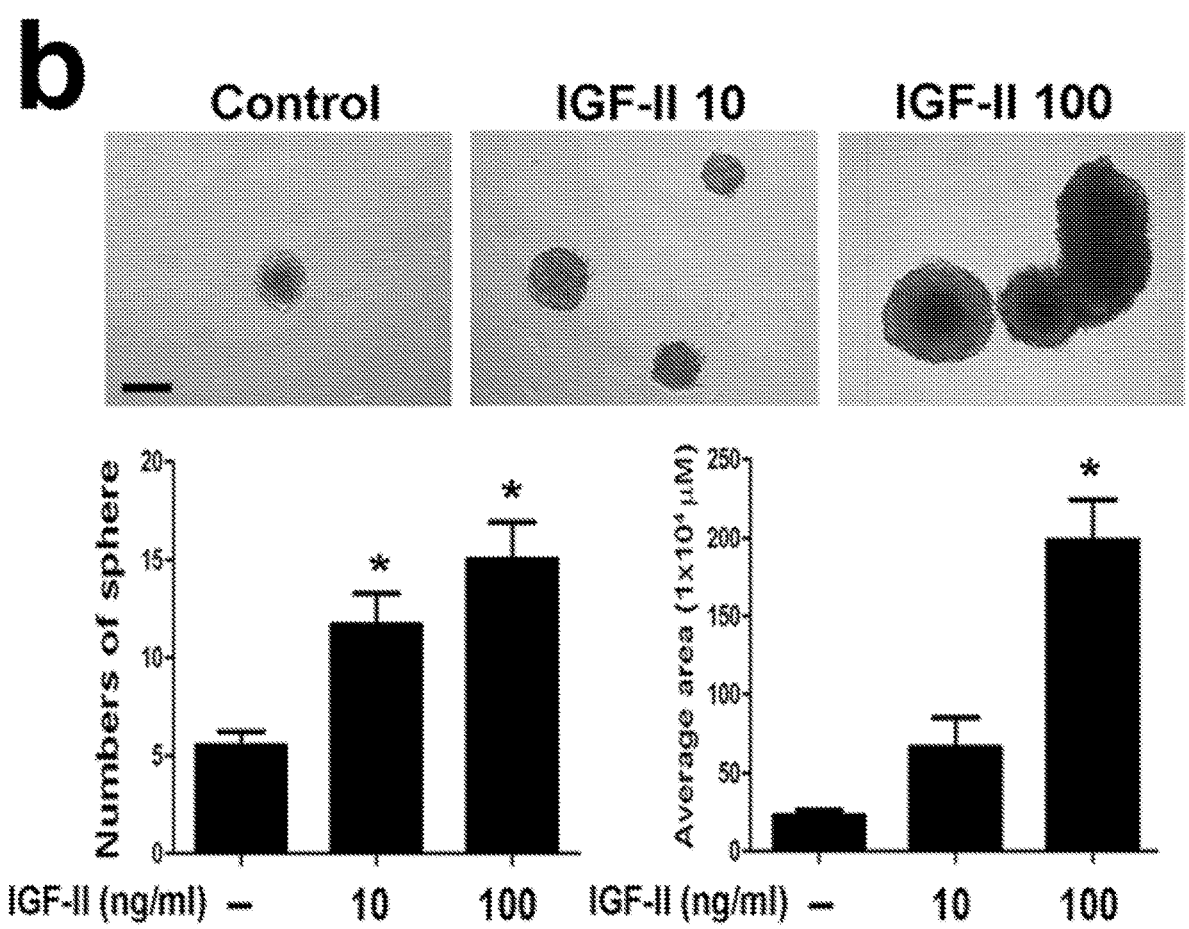
Figure 5:
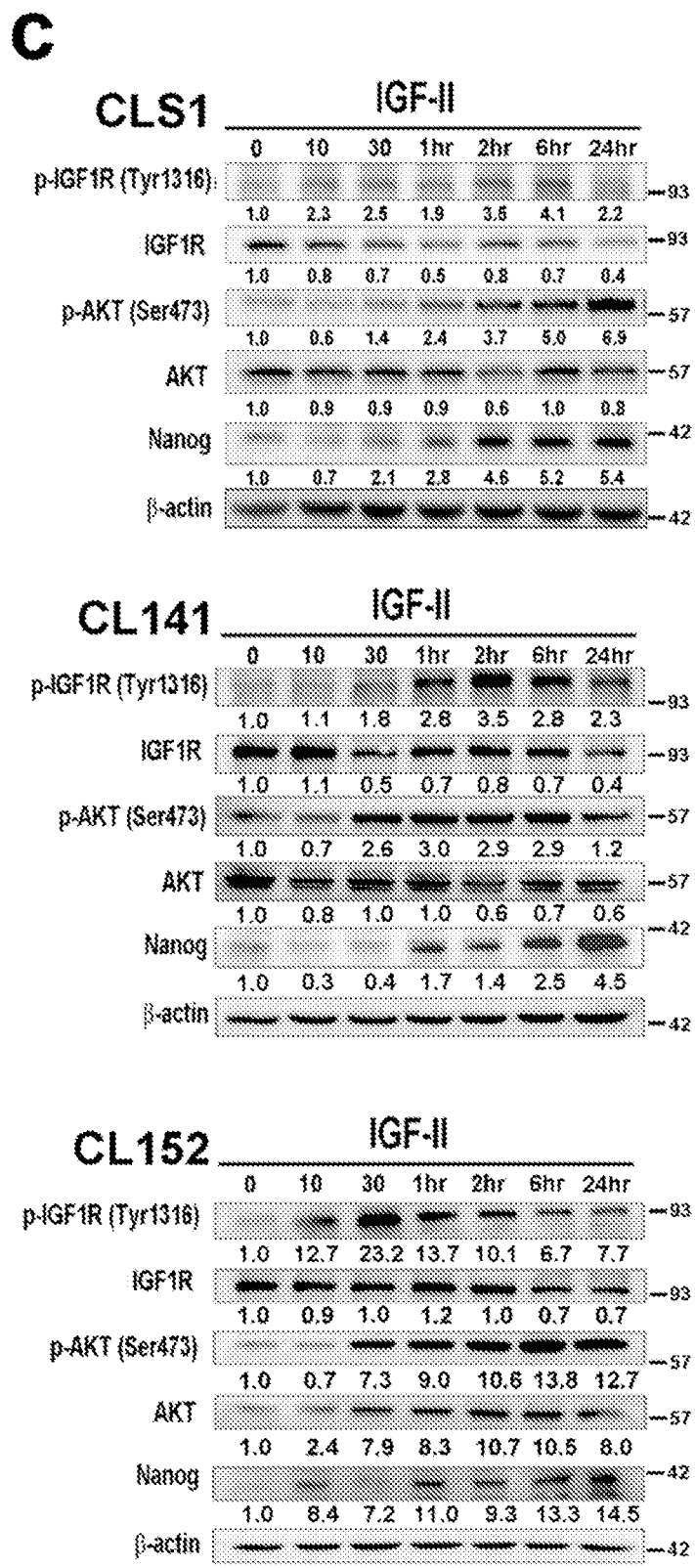
Figure 5:
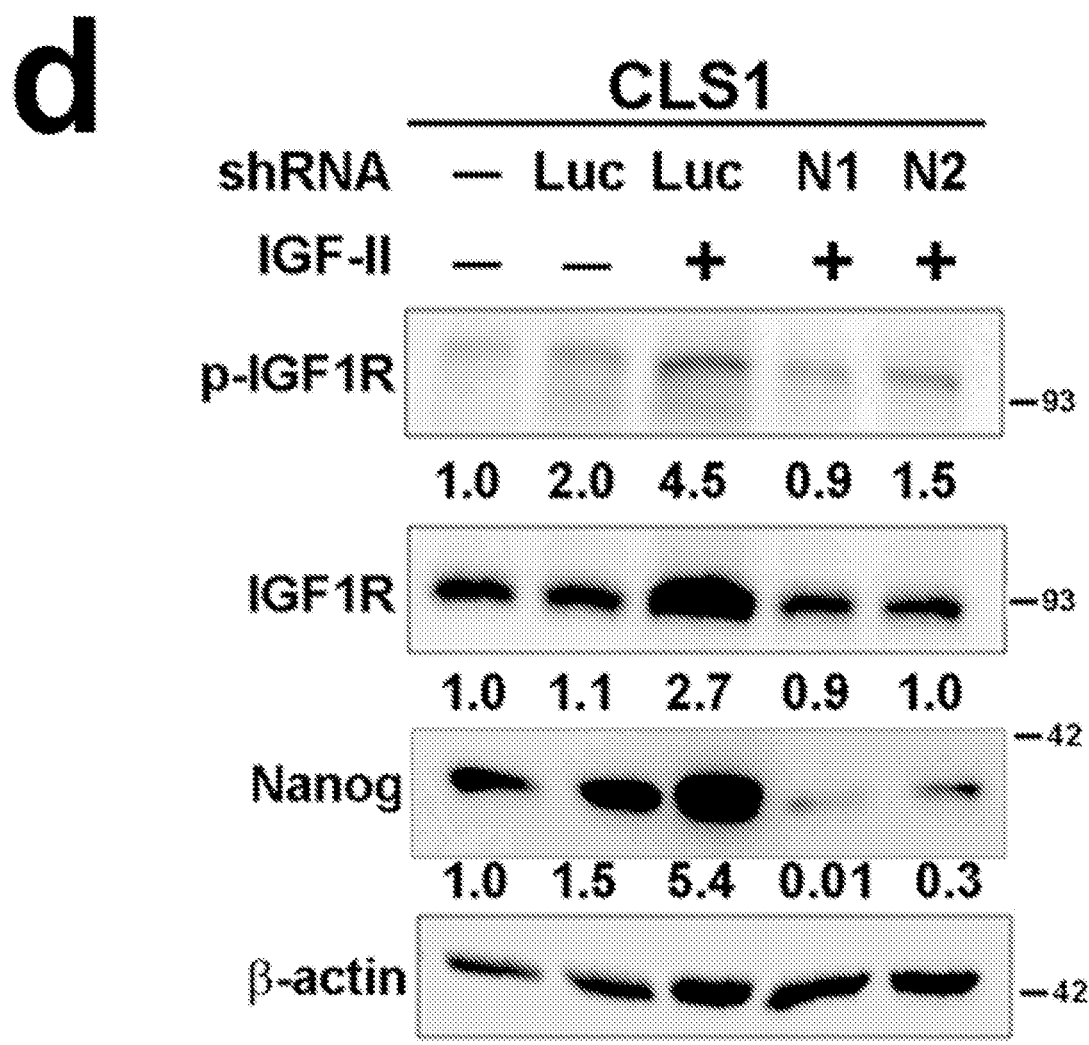
Figure 5:
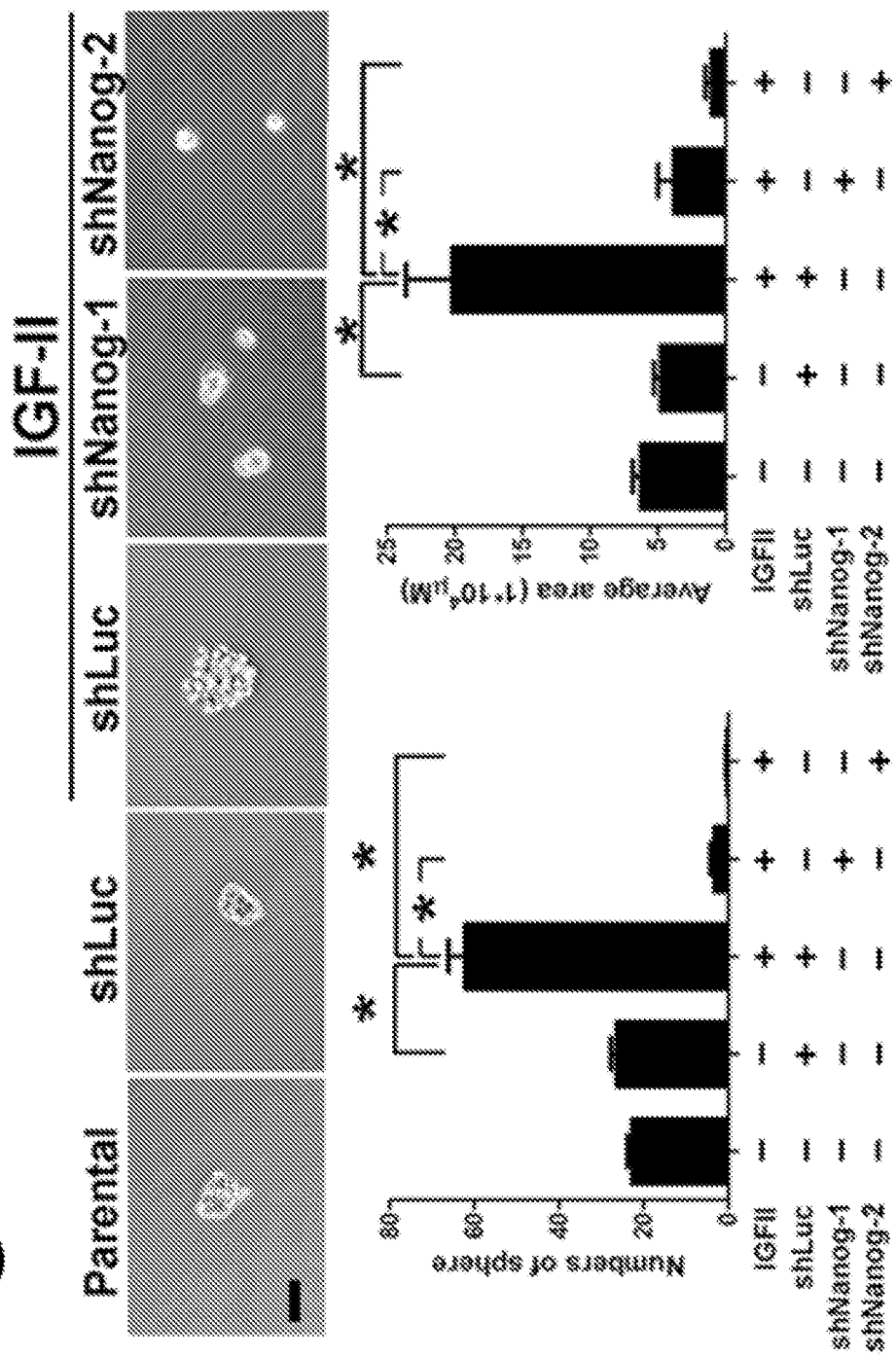
Figure 5:
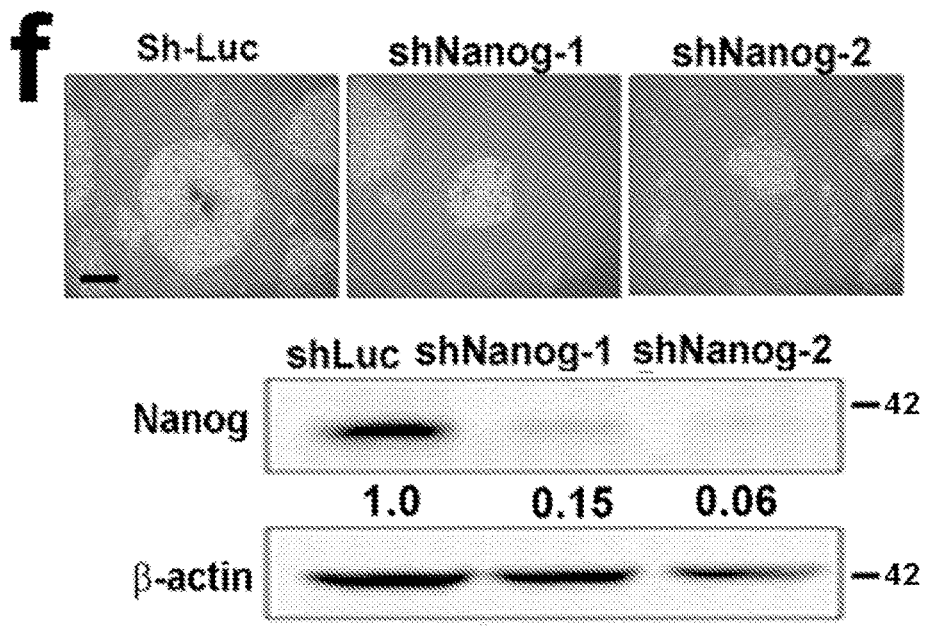
Figure 5:
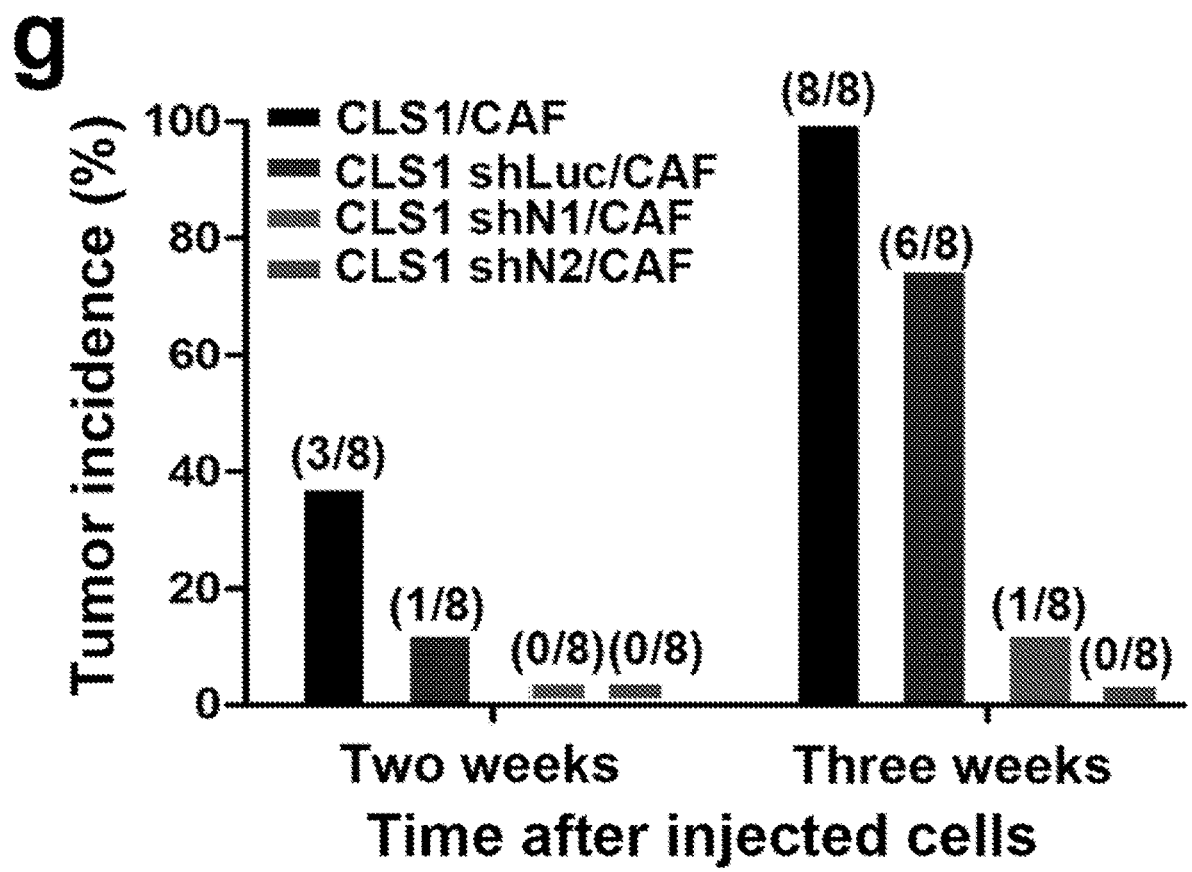
Figure 5:
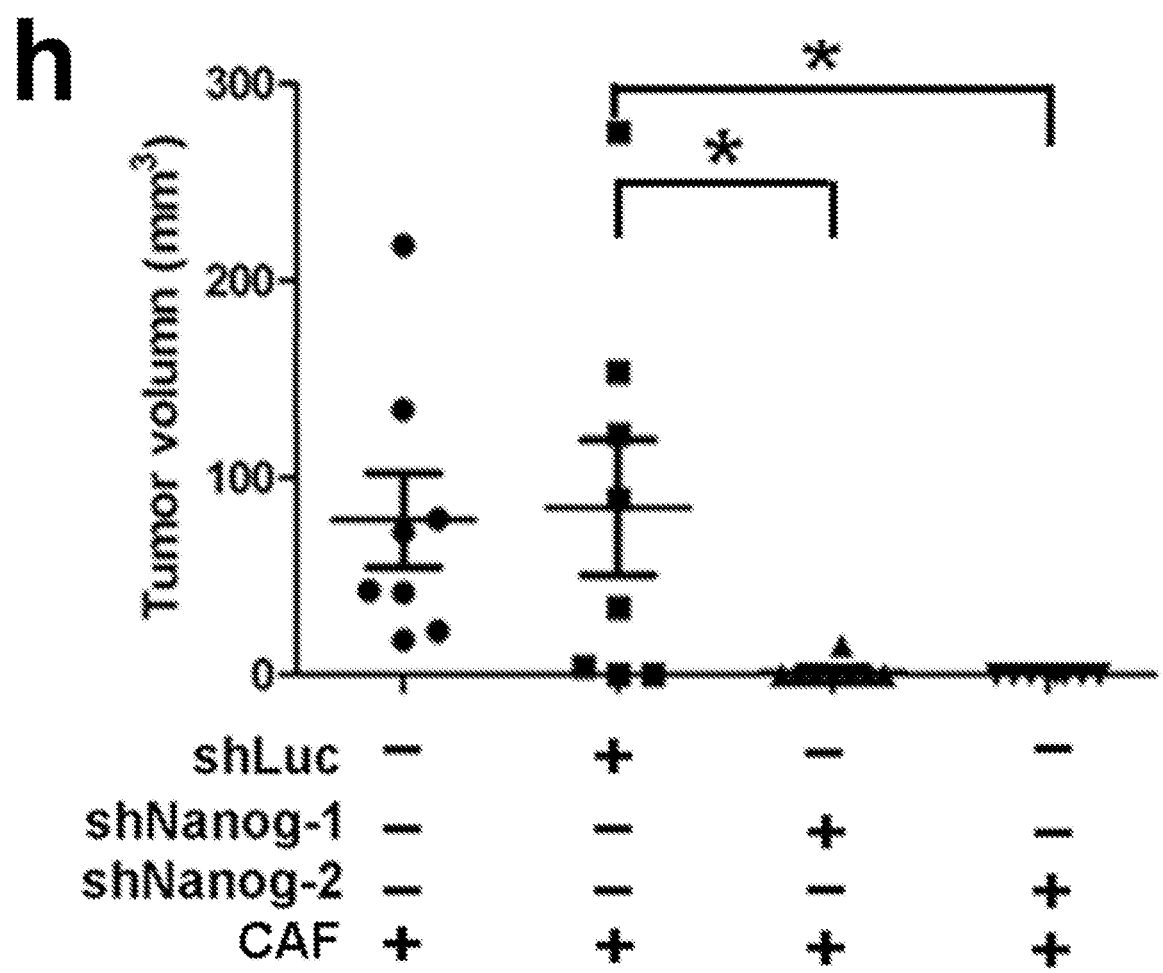
Figure 14:
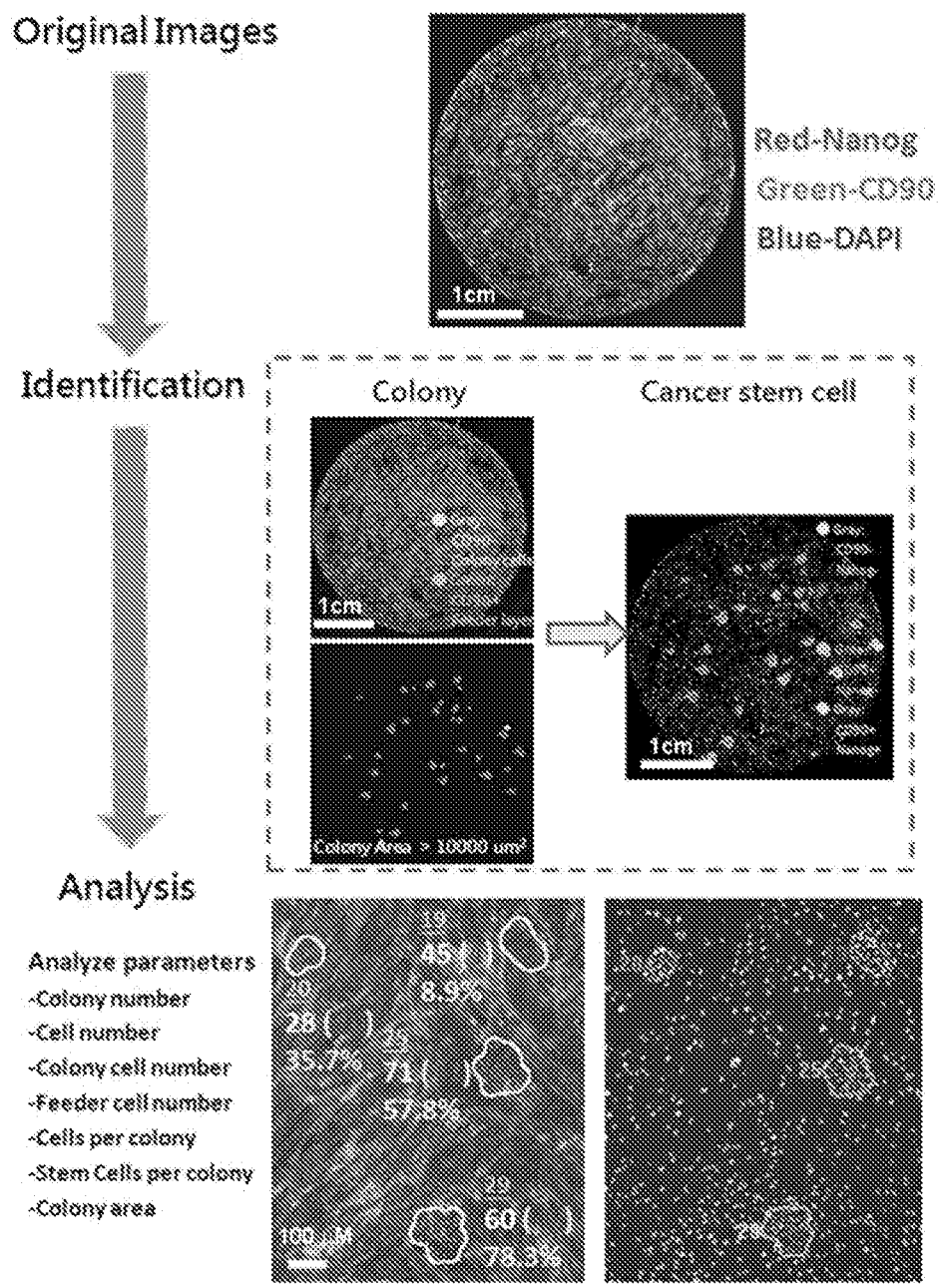
FIG. 14 include diagrams showing the procedures of identifying cancer stem cells through high content analysis. (a) CD90 as the CAF marker; Nanog for the stemness cells; DAPI staining for the nuclei and helpful for identifying the CSC colony by image-based high content analysis. Colony numbers, area, cells per colony, and Nanog-positive cells. (b) Image-based high content analysis showing the Nanog (+) colony-forming ability of CLS1 cells increased under the treatment of IGF-II (10 and 100 ng/ml). Data represent the mean±S.D. and tested for significance by Student's t-test *$P<0.05$. Data are representative of three independent biological experiments each.
Figure 14:
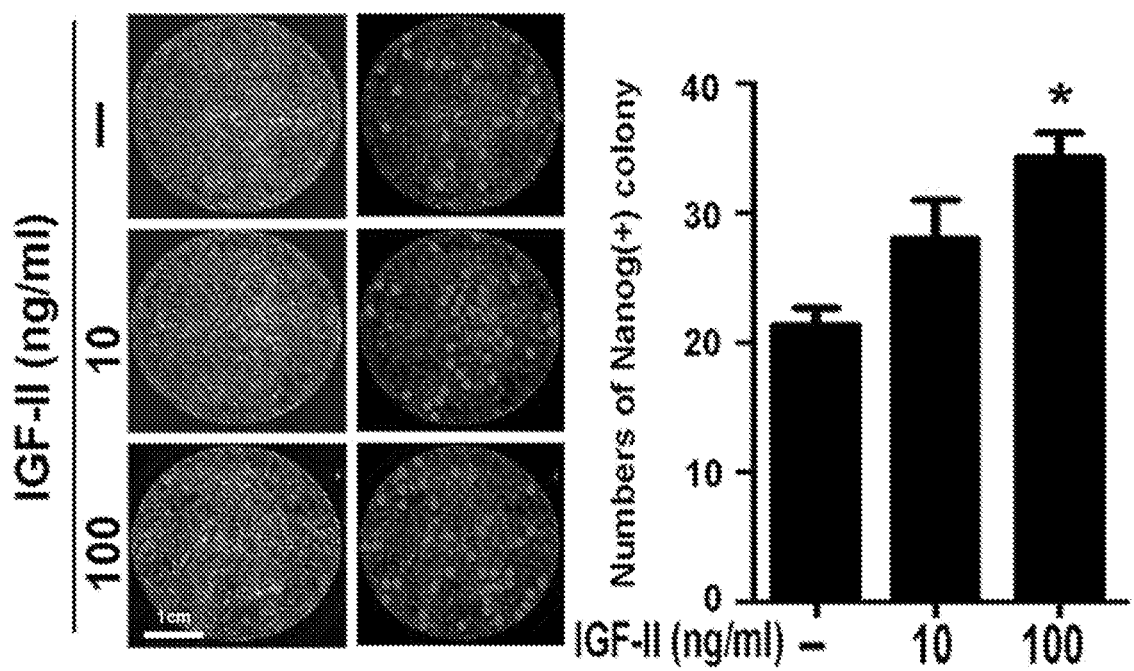
Figure 15:
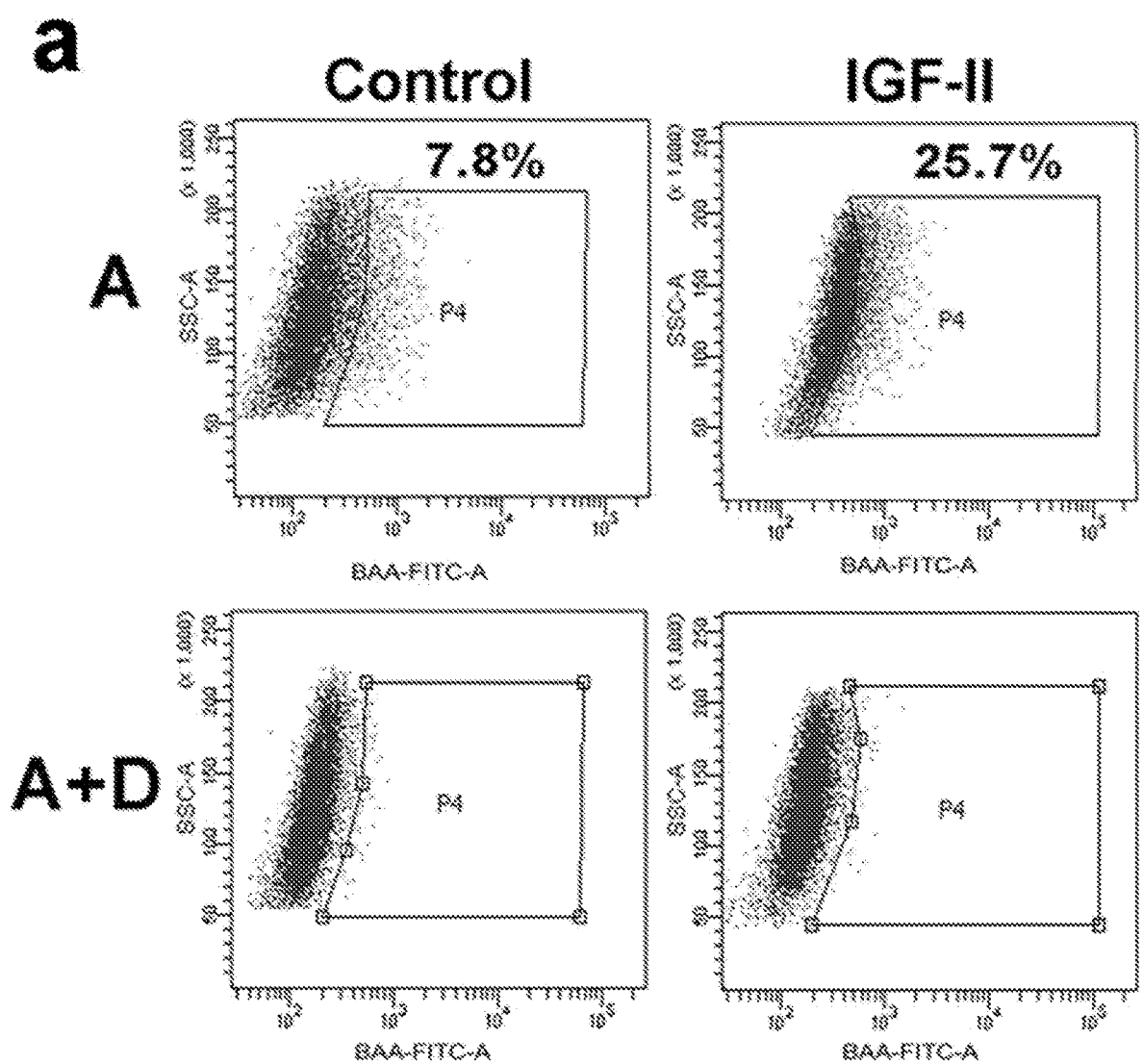
FIG. 15 includes diagrams showing IGF-II induced stemness in different lung cancer cell lines. (a) Flow cytometric analysis with ALDEFLUOR assay of CLS1/CAFs cells treated with IGF-II (100 ng/ml). The fluorescence intensity corresponding to the ALDH activity was measured without DEAB (upper panel) and with DEAB (lower panel). (b) The ALDH activity was examined by flow cytometry in four different lung cancer cell lines (CLS1/CAFs, A549, H1975, and EKVX) treated with IGF-II (100 ng/ml). Data represent the mean±S.D. and tested for significance by Student's t-test *$P<0.05$. Data are representative of three independent biological experiments each.
Figure 15:
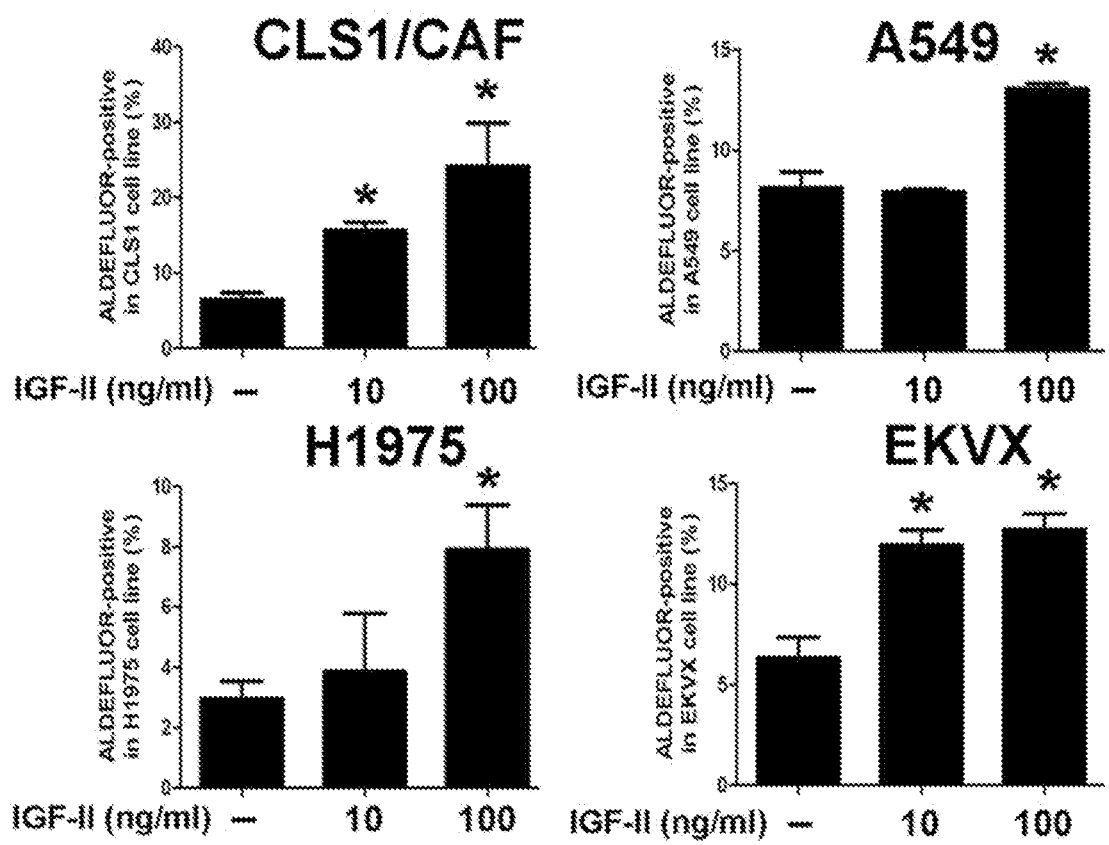
Figure 16:
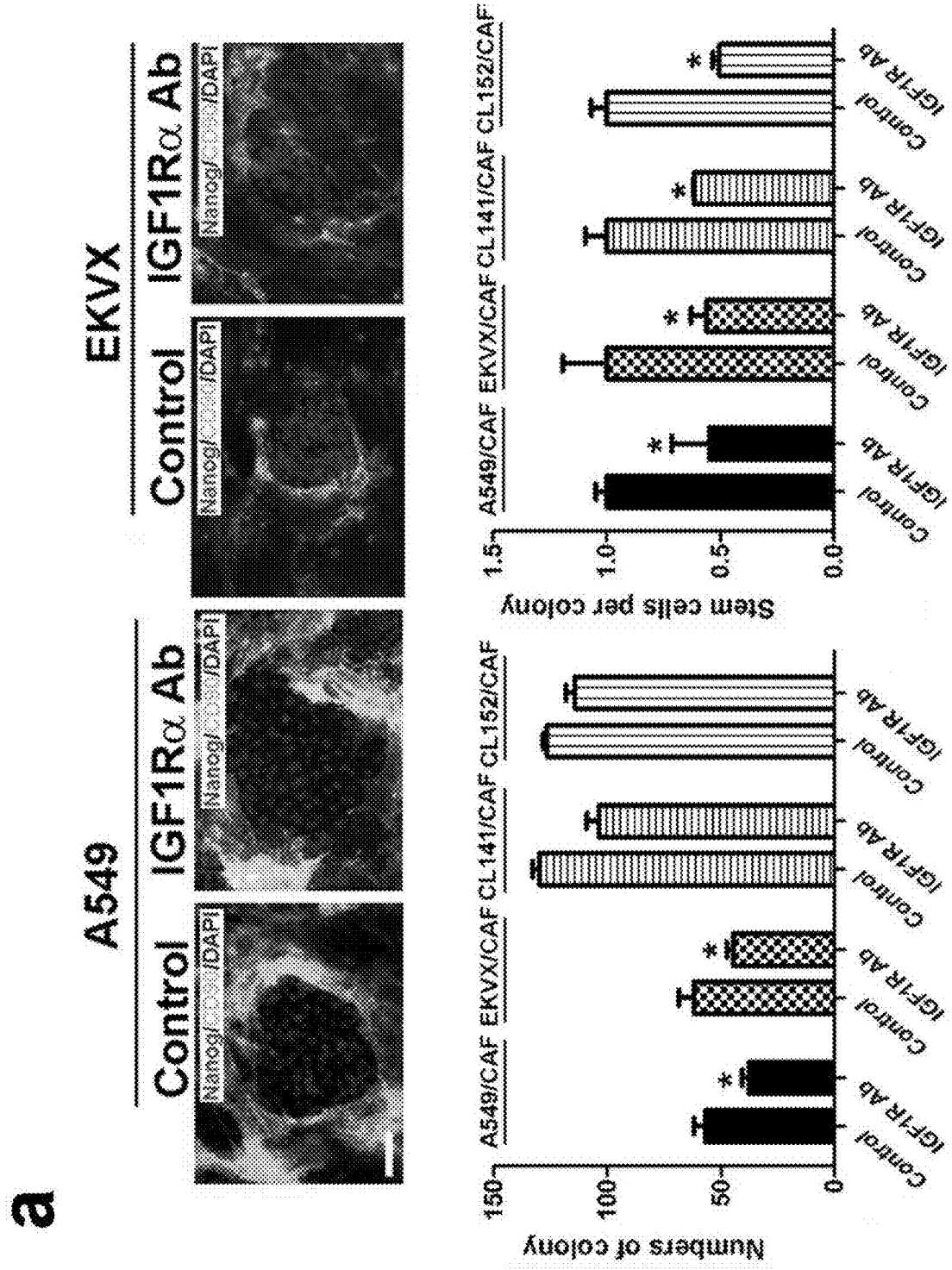
FIG. 16 includes diagrams showing that blockage of IGF1R signaling by IGF1R neutralize Ab or inhibitor suppresses stemness in different lung cancer celllines. (a) The A549, and EKVX cells were co-cultured with CAFs treated with or without IGF1Rα Ab (1 µg/ml); the number of Nanog-positive stem cells per colony was examined. (N=3) (b) The Nanog-positive stem cells per colony were analyzed by image-based high content analysis. The different primary lung cancer cell lines (CLS1, CL141 and CL152) were co-cultured with CAFs treated with or without the IGF1R kinase inhibitor (AEW541 under 1, 5 10 µM/ml). (N=3) (c) The sphere-forming morphology and ability (Numbers of sphere, N=6; Average area of sphere, N=10) of the lung cancer cell lines, including A549 and EKVX, were significantly reduced by treatment with IGF1Rα Ab (1 µg/ml). Data represent the mean±S.D. and tested for significance by Student's t-test *$P<0.05$. Data are representative of at least three independent biological experiments each.
Figure 16:
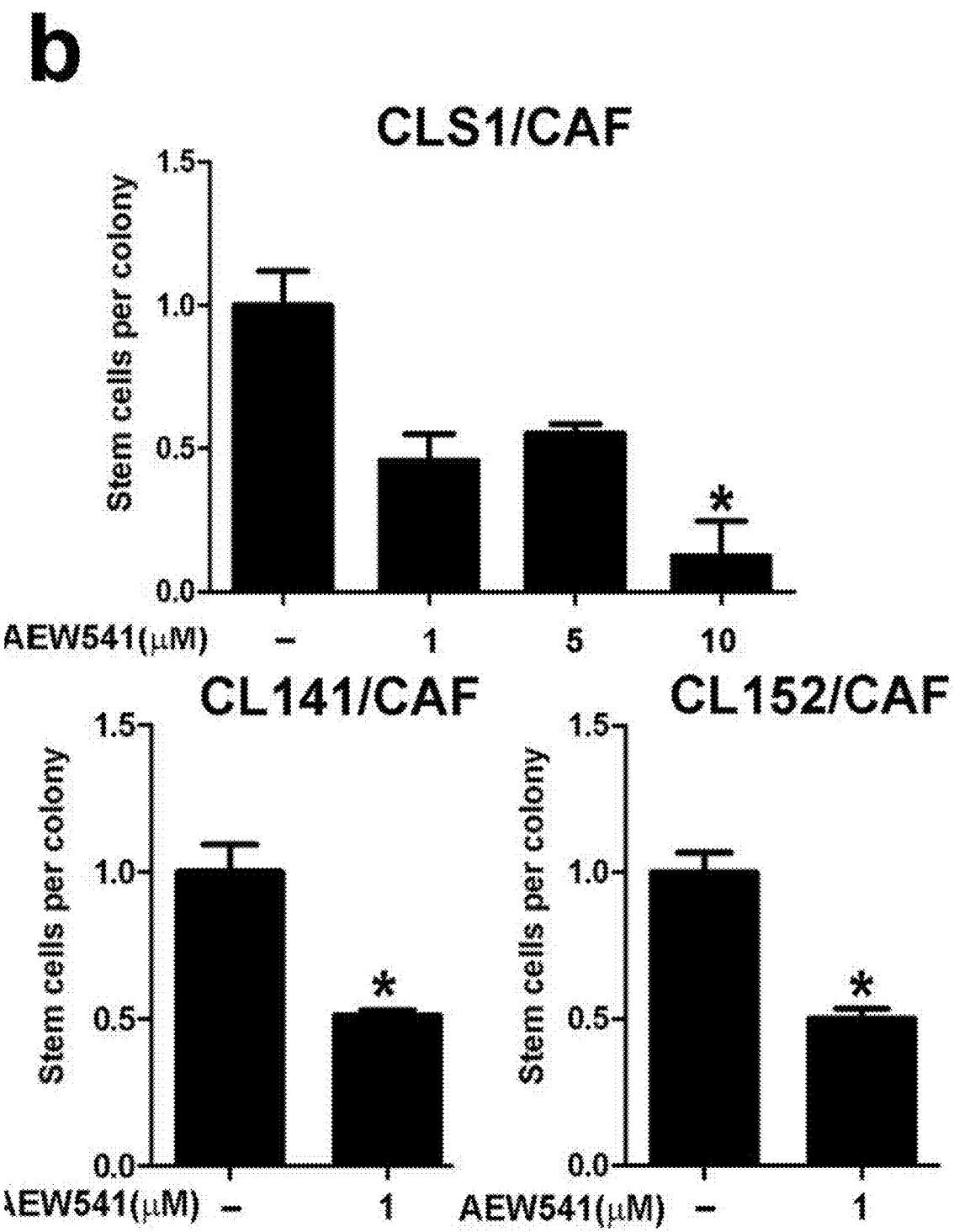
Figure 16:
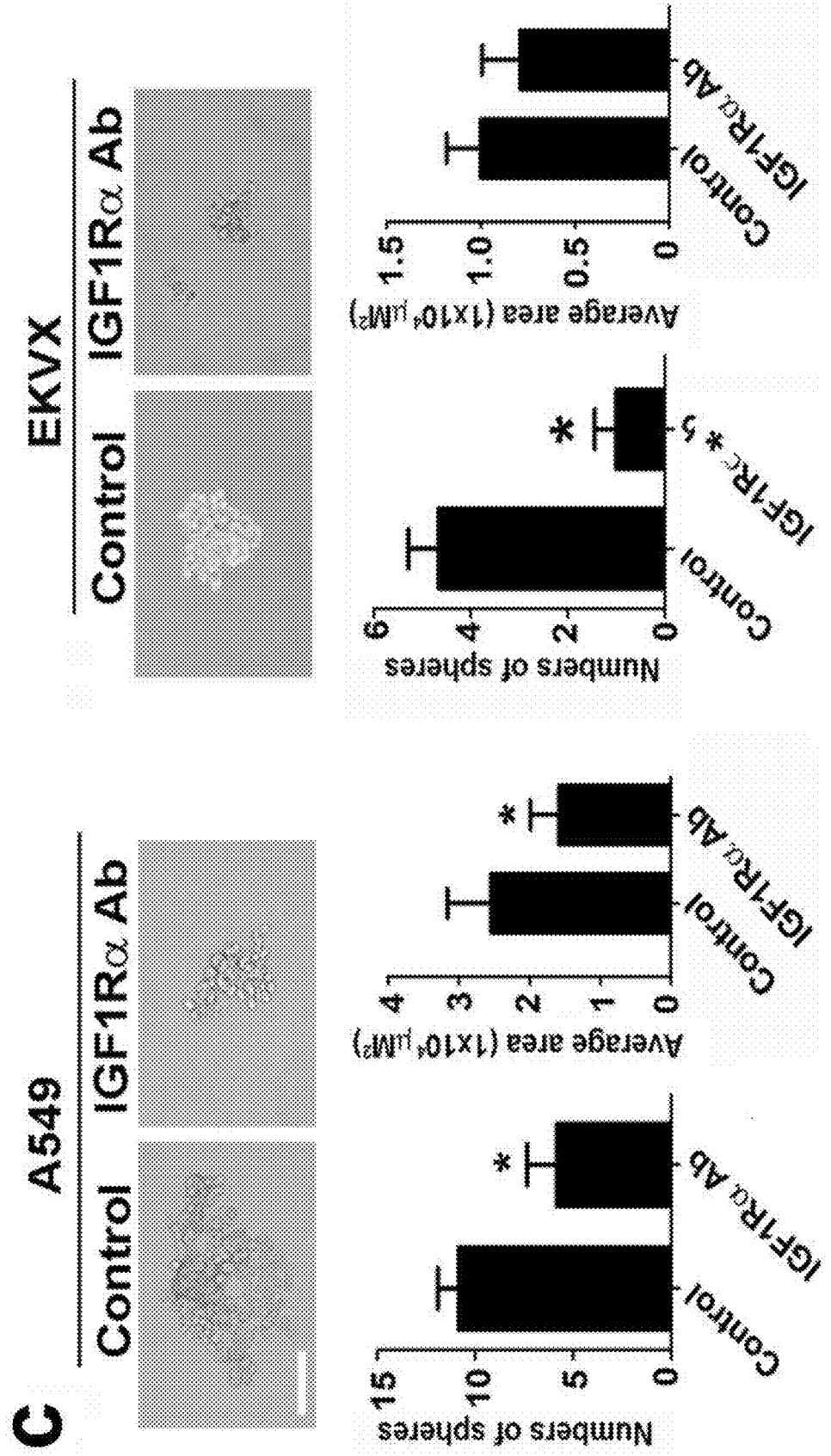

To further validate the roles of IGF-II signaling on cancer stemness in lung CSCs, several cancer stemness characteristics were examined in CLS1 and other lung cancer cell lines. It was found that IGF-II increased the Nanog expression (FIG. 5a), and enlarged the sphere numbers and size (FIG. 5b), facilitated the number of Nanog-positive cells per colony through image-based high-content analysis (HCA; FIG. 14a, b. See also Example 2) and increased the ALDEFLUOR-positive ratio (FIGS. 15a and 15b) in various lung cancer cells (CLS1/CAFs, A549, H1975 and EKVX). Western blotting further showed that IGF-II induced IGF1R and Akt phosphorylation and downstream Nanog expression in a time-dependent manner in primary lung cancer cells (CLS1, CL141 and CL152; FIG. 5c). Moreover, the PI3K inhibitor LY294002 significantly reduced the number of Nanog-positive cells per colony in primary lung cancer cells (CLS1, CL141 and CL152) co-cultured with CAFs. In addition, LY294002 (at 1, 5, and 10 µM/ml) inhibited IGF-II-induced Akt-phosphorylation and Nanog expression and reduce the tumorigenicity of CLS1 cells ($10^3$ cells) in NOD/SCID mice. Together, these results suggest that PI3K could be the intermediary component of the IGF-II/IGF1R/Nanog signaling pathway and that blocking PI3K signaling may thereby reduce IGF-II-regulated cancer stemness.

Furthermore, it was found that IGF-II-regulated cancer stemness could be attenuated by the specific knockdown of Nanog. As shown in FIG. 5d, an shRNA against Nanog inhibited IGF-II-induced p-IGF1R and Nanog expression and reduced sphere-forming ability in vitro (FIG. 5e, f) and tumorigenicity in NOD/SCID mice (FIG. 5g, h), indicating the importance of Nanog in IGF-II-induced lung cancer stemness.

(ix) Blockade of IGF1R Signaling Suppresses Lung Cancer Stemness

Figure 6:
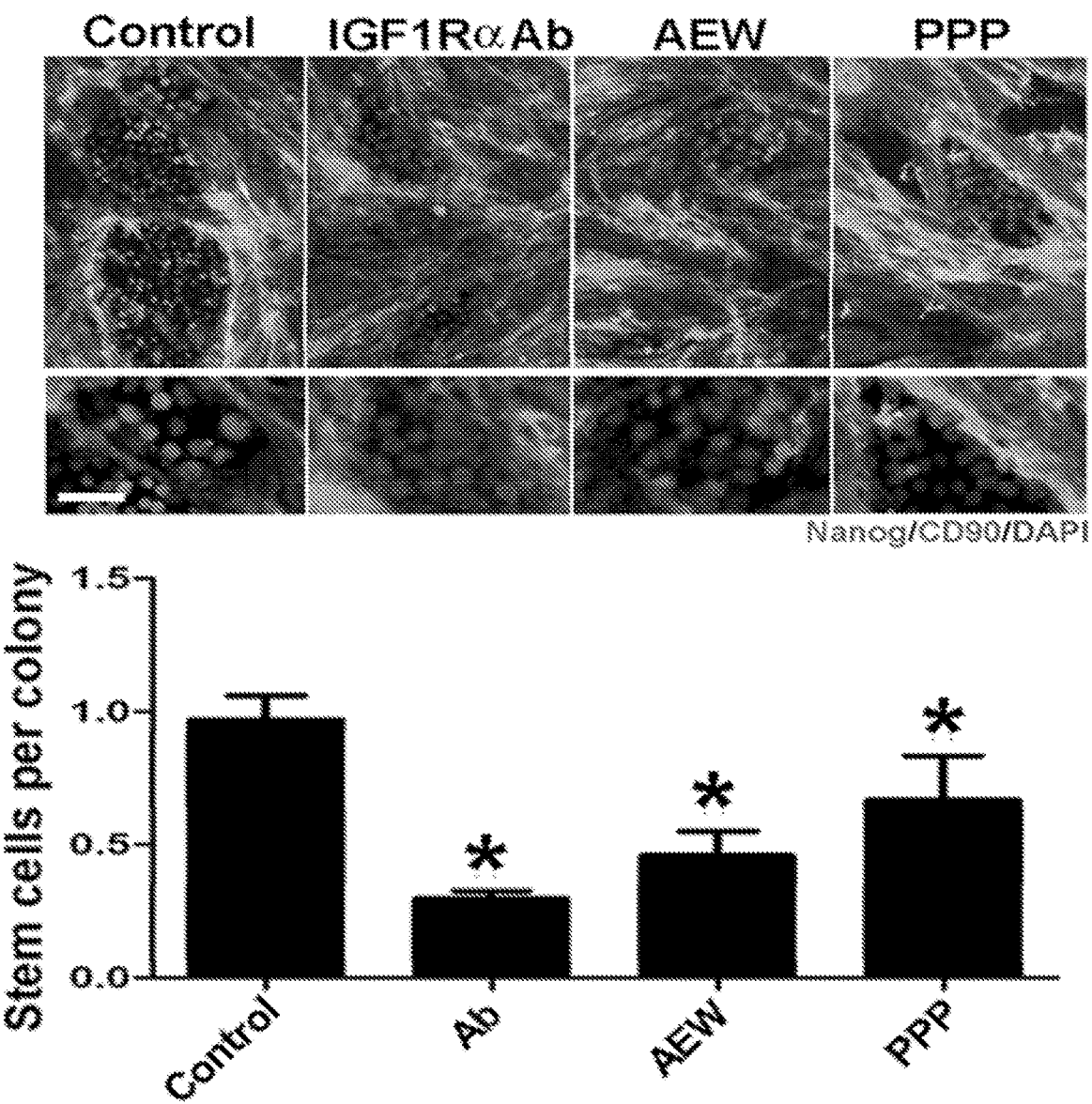
FIG. 6 includes diagrams showing the IGF-II/IGF1R signaling pathway as a target to suppress lung cancer stemness and tumorigenicity. (a): photo and chart showing Nanog-positive stem cells per colony, which were analyzed through image-based high-content analysis. CLS1 cells were co-cultured with CAFs treated with or without an IGF1R-neutralizing antibody (IGF1Rα Ab; 1 μg/ml) and an IGF signaling inhibitor (AEW541 and PPP 1 μM/ml) (N=3). Scale bar, 50 μm. (b): photo and chart showing the sphere-forming morphology and ability (Numbers of sphere, N=6; Average area of sphere, N=10) of the CLS1, which were significantly reduced by treatment with IGF1Rα Ab (1 μg/ml). Scale bar, 200 μm. (c): charts showing ALDH activity, which was examined using flow cytometry for four different lung cancer cell lines (CLS1, A549, H1975 and EKVX) treated with IGF-II (100 ng/ml) or IGF-II in combination with IGF1Rα Ab (N=3). (d): charts showing RT Q-PCR analysis of the stem cell marker Nanog expressed in CLS1, A549, H1975 and H460 cells treated with IGF-II (100 ng/ml) or IGF-II in combination with IGF1Rα Ab (N=3). (e): photos showing Western blot analysis of IGF1R-p/IGF1R, AKT-p/AKT and Nanog in CLS1 cells treated with IGF-II or IGF-II in combination with IGF1Rα Ab (1 μg/ml) for 6 h (CLS1 cells) or 24 h (CL141 and CL152 cells). (f): photos and a chart showing the incidence of xenograft tumors formed from CLS1/CAF cells, which was reduced following treatment with 1 μg/ml IGF1Rα Ab. The tumors were generated by the injection of 1,000 CLS1/CAF cells (N=5 mice). The tumor-forming ability of CLS1/CAF cells was inhibited by IGF1Rα Ab (1 μg/ml) treatment (N=5 mice) (100% (5/5) in control vs. 40% (2/5) in IGF1Rα Ab-treated group). The data represent the mean±S.D. and were tested for significance by one-way ANOVA with Turkey's post hoc corrections (a) or the Student's t-test (b-d); *P<0.05. The data are representative of three independent experiments, with three or more replicates in each experiment.
Figure 6:
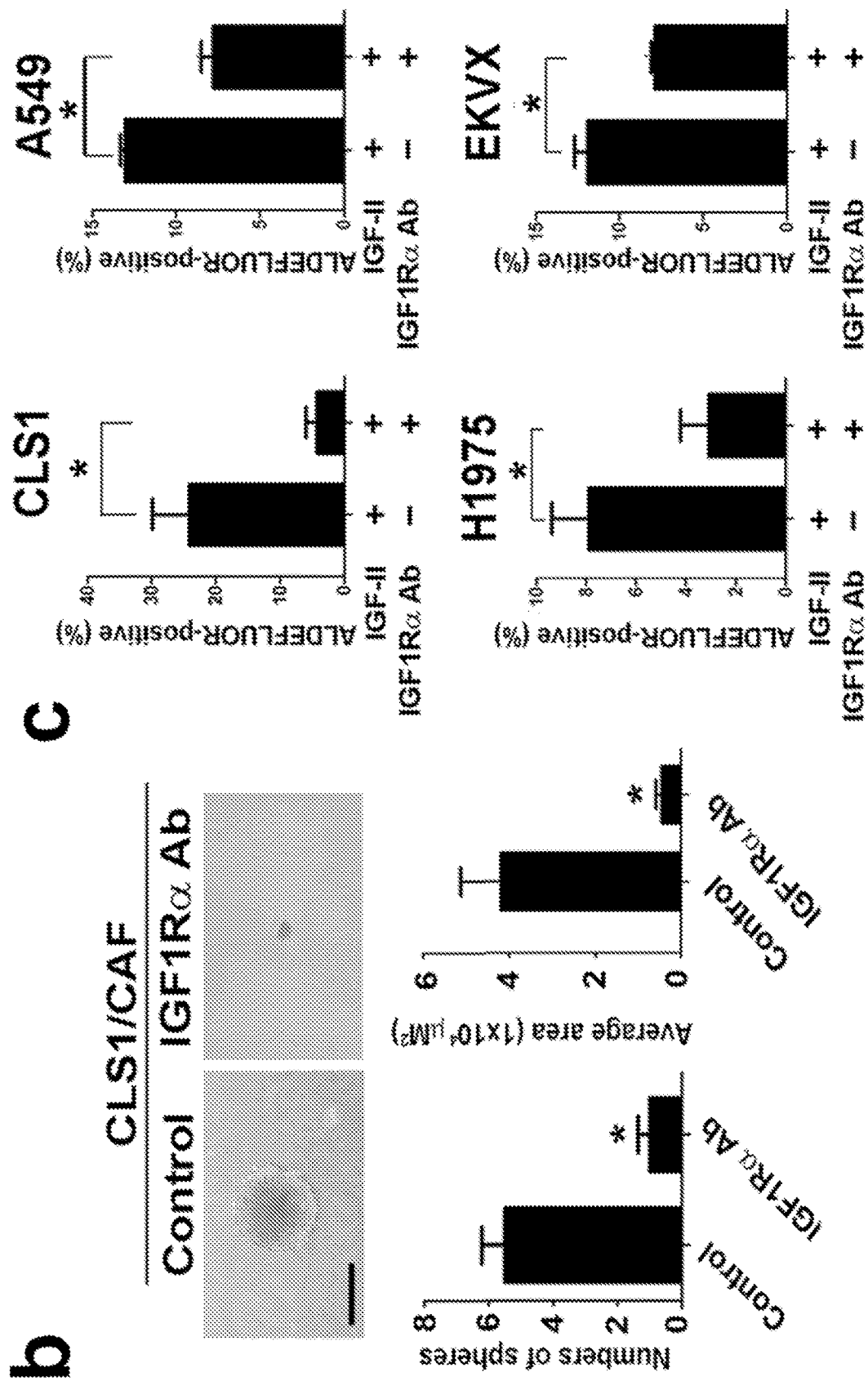
Figure 6:
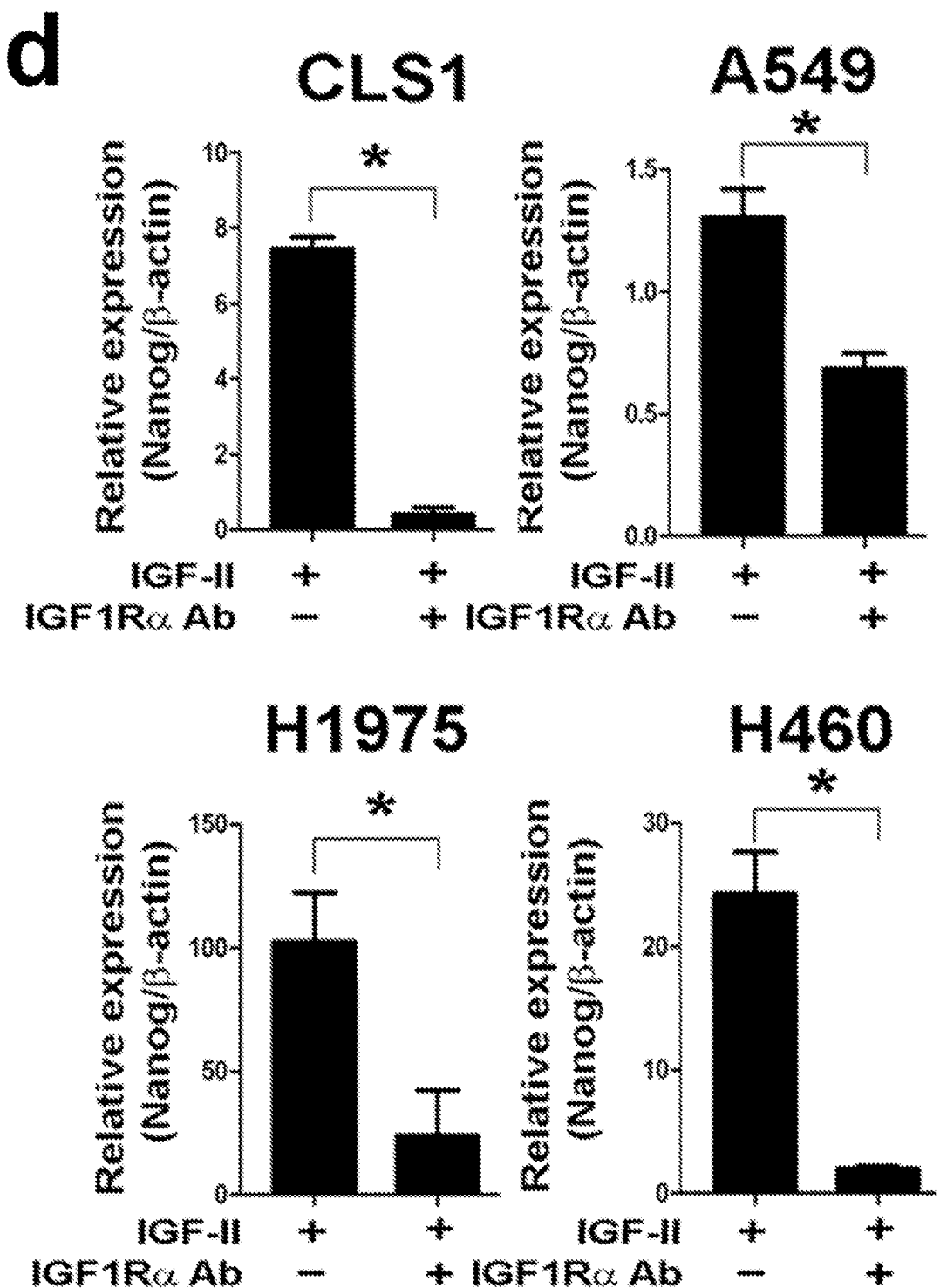
Figure 6:
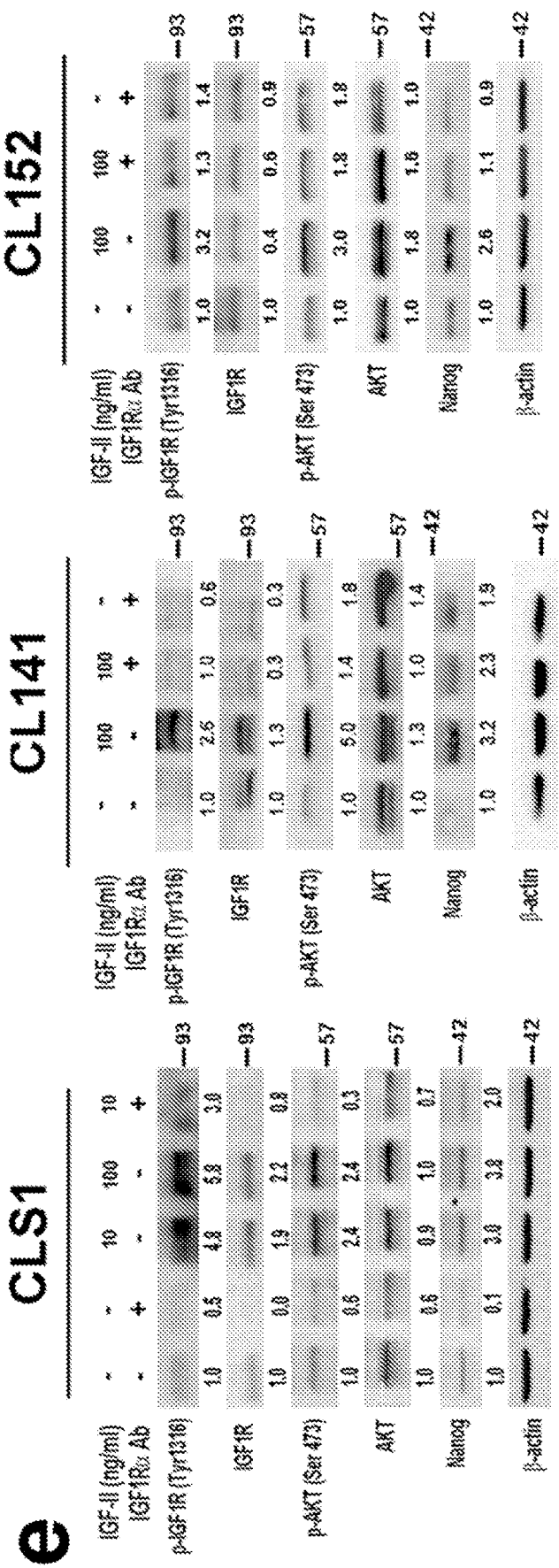
Figure 6:
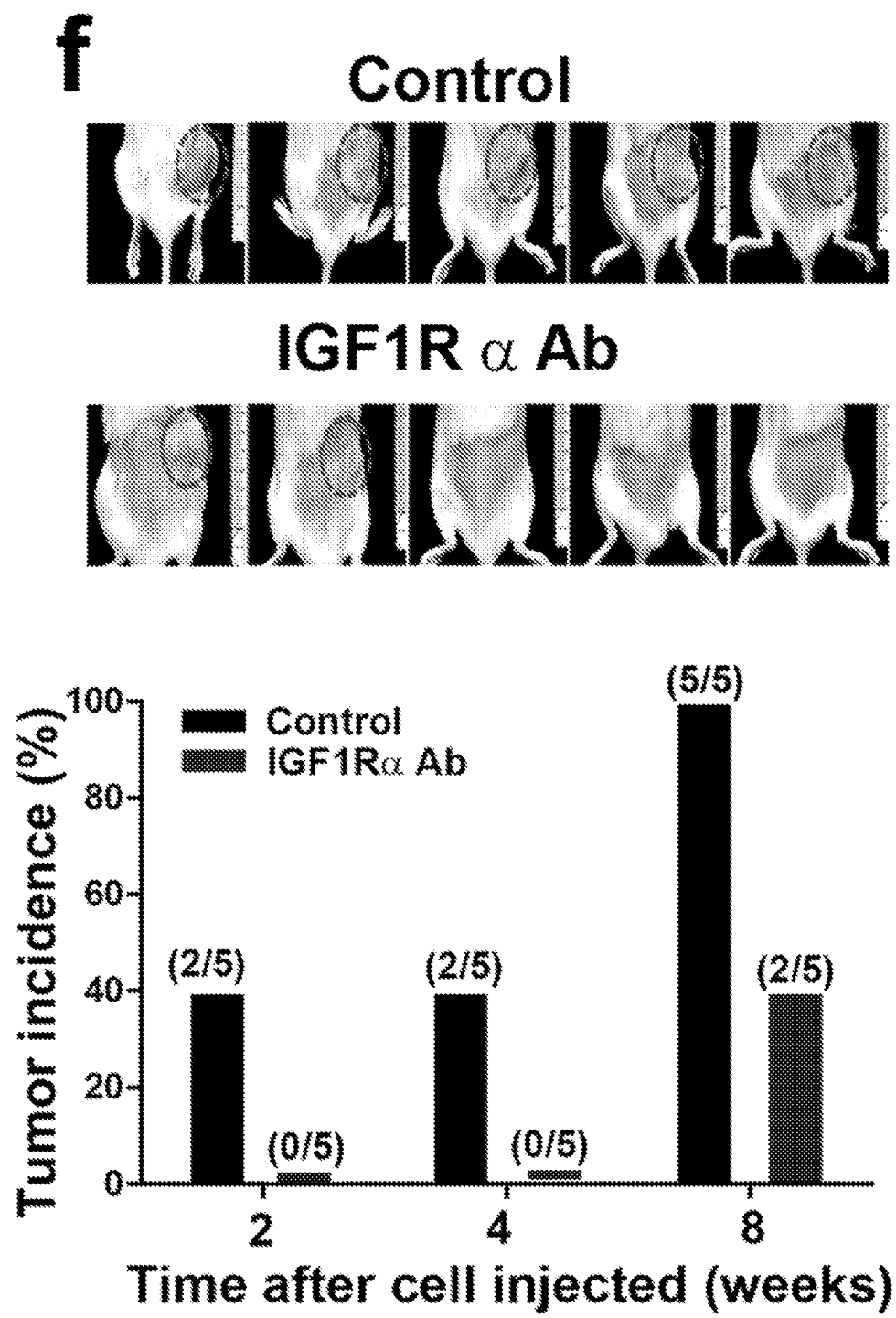
Figure 17:
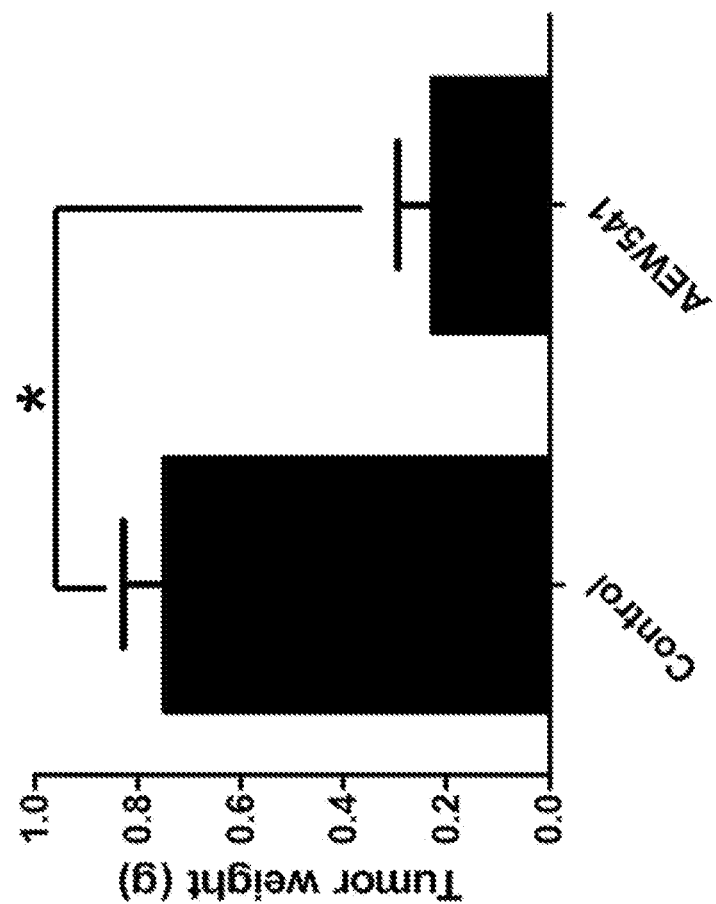
FIG. 17 includes diagrams showing that blockage of IGF1R signaling by IGF1R kinase inhibitors suppresses lung cancer stemness in vivo. The tumorigenesis ability of xenograft tumors from CLS1/CAF cells was reduced by treatment with AEW541. The tumors were generated by the injection of 1,000 CLS1/CAF cells. The tumor weight of the CLS1/CAF cells was decreased by the AEW541 (5 μM/ml) treatment (N=5 mice each group).
Figure 17:
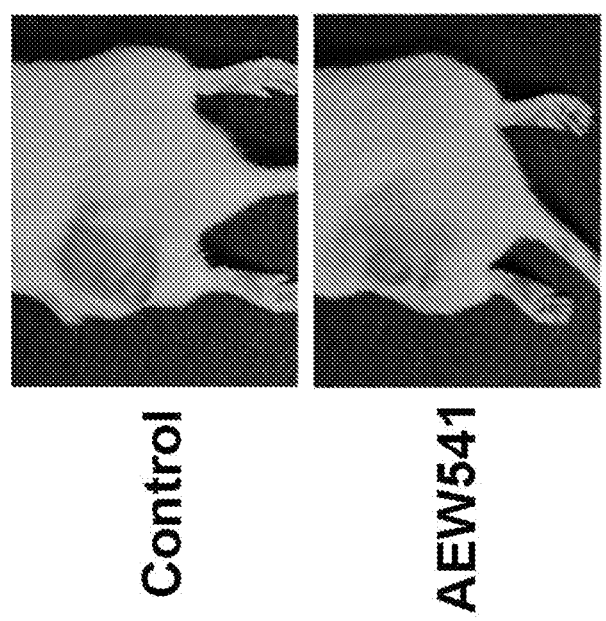

To further evaluate whether IGF-II signaling is a druggable pathway for anti-cancer therapy by targeting lung CSCs, specific IGF1R blockade strategies were used. Image-based HCA showed that the Nanog-positive cells in each colony were significantly inhibited in the presence of a specific IGF1R antibody or IGF1R inhibitors (picropodophyllin, PPP and AEW541) in lung cancer cell lines (A549, EKVX) and primary lung cancer cells (CLS1, CL141 and CL152; FIG. 6a). Using an IGF1R blocking antibody (IGF1Rα Ab), it was further confirmed that the sphere-forming ability of CLS1 cells was reduced following blockade of IGF1R signaling (FIG. 6b); similar effects were observed in A549 and EKVX cells. It was also found that the ALDEFLUOR-positive ratio, which was substantially increased after IGF-II treatment, was blocked following the addition of IGF1Rα Ab in lung cancer cell lines (CLS1, A549, H1975 and EKVX; FIG. 6c). Moreover, the IGF-II-mediated up-regulation of Nanog expression was also inhibited when IGF1R signaling was blocked (FIG. 6d), as well as IGF-II-induced IGF1R phosphorylation, Akt phosphorylation and downstream Nanog signaling in CLS1, CL141 and CL152 cells (FIG. 6e). Most importantly, the IGF1Rα Ab and inhibitor (AEW541) significantly reduced the tumorigenicity of CLS1 cells ($10^3$ cells) injected into NOD/SCID mice (FIG. 6f and FIG. 17), revealing that IGF-II signaling represents a potential anti-cancer target for lung CSCs.

(x) Concomitant IGF-II-IGF1R/Nanog Correlates with Poor Prognosis

The present studies have demonstrated that CAFs act as "feeders" that secrete IGF-II and act on IGF1R in lung cancer cells, driving stemness pathways and maintaining the cancer stemness characteristics. To examine the clinical relevance and importance of IGF-II/IGF1R/Nanog paracrine regulation in the early stages of tumorigenesis, tumor specimens from 80 patients with stage-I NSCLC who had not received preoperative chemo- or radiotherapy were collected, and serial sections of each specimen were stained with antibodies against IGF-II, IGF1R and Nanog via IHC. The clinical characteristics of these patients are summarized in Tables 7-9 below. The levels of IGF-II in CAFs and of IGF1R/Nanog in tumor cells were scored and dichotomized to high (score median risk score) or low (score<median risk score) IGF-II, IGF1R and Nanog protein expression categories.

TABLE 7

Clinical Characteristics of IGF-II and IGF1R Expression in Lung Cancer Patients

|  | High (%) | Low (%) | p-value |
|---|---|---|---|
| IGF-II | N = 39 | N = 41 |  |
| Age (mean ± SD) | 63.1 ± 10.1 | 62.8 ± 9.2 | 0.900 |
| Gender |  |  |  |
| Female | 16 (41.0) | 25 (61.0) | 0.117 |
| Male | 23 (59.0) | 16 (39.0) |  |
| Cell type |  |  |  |
| Adenocarcinoma | 33 (84.6) | 31 (75.6) | 0.401 |
| Others | 6 (15.4) | 10 (24.4) |  |
| Size (mean ± SD) | 3.6 ± 2.1 | 3.3 ± 1.4 | 0.331 |

TABLE 7-continued

Clinical Characteristics of IGF-II and IGF1R Expression in Lung Cancer Patients

|  | High (%) | Low (%) | p-value |
|---|---|---|---|
| Proliferative marker |  |  |  |
| High | 23 (56.1) | 18 (43.9) | 0.189 |
| Low | 16 (41) | 23 (59.0) |  |
| Tumor grade |  |  |  |
| MD | 30 (54.5) | 23 (45.5) | 0.152 |
| WD | 9 (36) | 16 (64) |  |
| IGF1R | N = 43 | N = 37 |  |
| Age (mean ± SD) | 62.8 ± 10.0 | 63.1 ± 9.4 | 0.901 |
| Gender |  |  |  |
| Female | 17 (39.5) | 24 (64.9) | 0.027 |
| Male | 26 (60.5) | 13 (35.1) |  |
| Cell type |  |  |  |
| Adenocarcinoma | 35 (81.4) | 29 (78.4) | 0.785 |
| Others | 8 (18.6) | 8 (21.6) |  |
| Size (mean ± SD) | 3.9 ± 2.1 | 2.9 ± 1.0 | 0.012 |
| Proliferative marker |  |  |  |
| High | 26 (63.4) | 15 (36.6) | 0.116 |
| Low | 17 (43.6) | 22 (56.4) |  |
| Tumor grade |  |  |  |
| MD | 33 (60) | 22 (40) | 0.146 |
| WD | 10 (40) | 15 (60) |  |
| Nanog | N = 39 | N = 41 |  |
| Age (mean ± SD) | 63.6 ± 9.6 | 62.4 ± 9.8 | 0.589 |
| Gender |  |  |  |
| Female | 21 (53.9) | 20 (48.8) | 0.662 |
| Male | 18 (46.2) | 21 (51.2) |  |
| Cell type |  |  |  |
| Adenocarcinoma | 28 (71.8) | 36 (87.8) | 0.096 |
| Others | 11 (28.2) | 5 (12.2) |  |
| Size (mean ± SD) | 3.6 ± 1.4 | 3.3 ± 2.0 | 0.479 |
| Proliferative marker |  |  |  |
| High | 22 (53.7) | 19 (46.3) | 0.382 |
| Low | 17 (43.6) | 22 (56.4) |  |
| Tumor grade |  |  |  |
| MD | 33 (60) | 22 (40) | 0.004 |
| WD | 6 (24) | 19 (76) |  |

Continuous variables: t test
Categories variables: Fisher's exact test
MD: moderate differentiation;
WD: well differentiation
Proliferative marker r: proliferating cell nuclear antigen (PCNA)

TABLE 8

Clinical Characteristics of IGF-II Combine IGF1R Expression in Lung Cancer Patients

| IGF-II + IGF1R | IGF-$II^{hi}$IGF1$R^{hi}$<br>N = 33 | IGF-$II^{hi}$ or IGF1$R^{hi}$<br>N = 16 | IGF-$II^{low}$IGF1$R^{low}$<br>N = 31 | p-value |
|---|---|---|---|---|
| Age (mean ± SD) | 62.6 ± 10.5 | 64.4 ± 8.1 | 62.6 ± 9.6 | 0.795 |
| Gender |  |  |  |  |
| Female | 13 (39.4) | 7 (43.8) | 21 (67.7) | 0.057 |
| Male | 20 (60.6) | 9 (56.3) | 10 (32.3) |  |

TABLE 8-continued

Clinical Characteristics of IGF-II Combine IGF1R Expression in Lung Cancer Patients

| IGF-II + IGF1R | IGF-II$^{hi}$IGF1R$^{hi}$ N = 33 | IGF-II$^{hi}$ or IGF1R$^{hi}$ N = 16 | IGF-II$^{low}$IGF1R$^{low}$ N = 31 | p-value |
|---|---|---|---|---|
| Cell type | | | | |
| Adenocarcinoma | 29 (87.9) | 10 (62.5) | 25 (80.7) | 0.125 |
| Others | 4 (12.1) | 6 (37.5) | 6 (19.4) | |
| Size (mean ± SD) | 3.8 ± 2.2 | 3.7 ± 1.7 | 2.9 ± 1.1 | 0.125 |
| Proliferative marker | | | | |
| High | 20 (48.8) | 9 (22.0) | 12 (29.3) | 0.208 |
| Low | 13 (33.3) | 7 (18.0) | 19 (48.7) | |
| Tumor grade | | | | |
| MD | 25 (45.5) | 13 (23.6) | 17 (30.9) | 0.115 |
| WD | 8 (32) | 3 (12) | 14 (56) | |

TABLE 9

Clinical Characteristics of IGF-II Combine IGF1R and Nanog Expression in Lung Cancer Patients

| IGF-II + IGF1R + Nanog | IGF-II$^{hi}$IGF1R$^{hi}$Nanog$^{hi}$ N = 24 | IGF-II$^{hi}$ or IGF1R$^{hi}$ N = 31 | IGF-II$^{low}$IGF1R$^{low}$Nanog$^{low}$ N = 25 | p-value |
|---|---|---|---|---|
| Age (mean ± SD) | 64.0 ± 9.7 | 62.5 ± 10.2 | 62.5 ± 9.3 | 0.824 |
| Gender | | | | |
| Female | 10 (41.7) | 16 (51.6) | 15 (60.0) | 0.477 |
| Male | 14 (58.3) | 15 (48.4) | 10 (40.0) | |
| Cell type | | | | |
| Adenocarcinoma | 20 (83.3) | 23 (74.2) | 21 (84.0) | 0.640 |
| Others | 4 (16.7) | 8 (25.8) | 4 (16.0) | |
| Size (mean ± SD) | 3.5 ± 1.1 | 3.8 ± 2.4 | 2.9 ± 1.1 | 0.153 |
| Proliferative marker | | | | |
| High | 15 (36.6) | 15 (36.6) | 11 (26.8) | 0.424 |
| Low | 9 (23.1) | 16 (41.0) | 14 (35.9) | |
| Tumor grade | | | | |
| MD | 21 (38.2) | 22 (40) | 12 (21.8) | 0.012 |
| WD | 3 (12) | 9 (36) | 13 (52) | |

Figure 7:
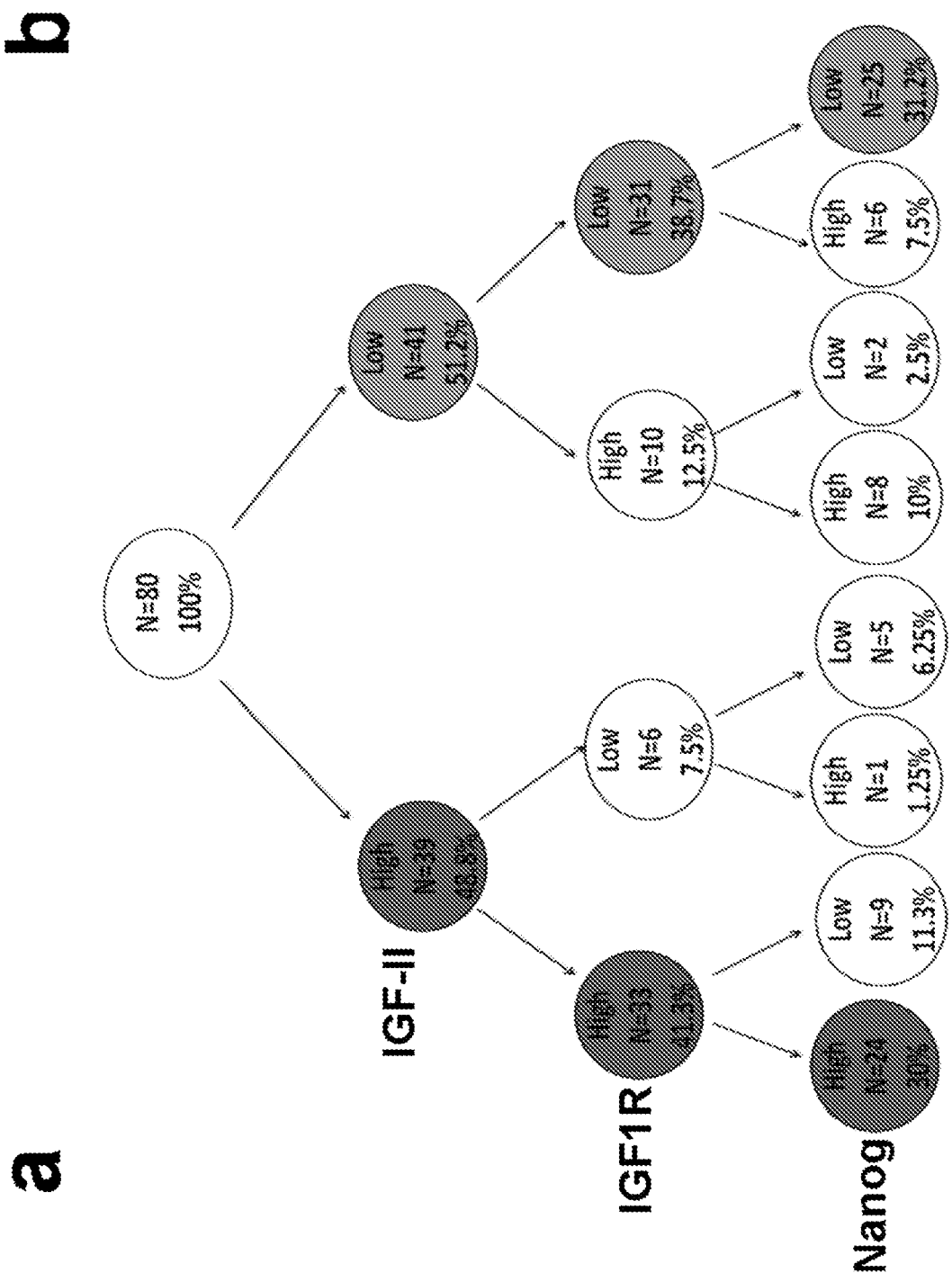
FIG. 7 include diagrams showing clinical significance of IGF-II in CAFs and IGF1R as well as Nanog in cancer cells for stage I NSCLC patients. (a): A tree diagram showing the proportions of patients with high and low IGF-II expression levels in CAFs and IGF1R/Nanog expression in tumor cells. (b): photos showing IHC staining of IGF-II in CAFs and IGF1R/Nanog in cancer cells from serial dissections of primary tumor specimens obtained from a clinical cohort of 80 patients with stage I NSCLC who underwent surgical resections. The images were obtained from different patients with low (score<median risk score) and high (score≥median risk score) expression of IGF-II in CAFs and IGF1R/Nanog in cancer cells (original magnification, 100×). (c-d): graphs showing that the patients were designated as having high or low IGF-II, IGF1R and Nanog expression (cut-off value=median risk score). The results showed a significant difference in the Kaplan-Meier estimates of overall (c) and relapse-free (d) survival between the high and low expression groups. P values were obtained from two-sided log-rank tests. (e): graphs showing the results by combining the expression levels of IGF-II in CAFs and IGF1R/Nanog in cancer cells, the patients were divided into three groups: a high IGF-II/high IGF1R/high Nanog group, a low IGF-II/low IGF1R/low Nanog group and others. The results showed a significant difference in Kaplan-Meier estimates of overall and relapse-free survival. P values were obtained from 2-sided log-rank tests.
Figure 7:
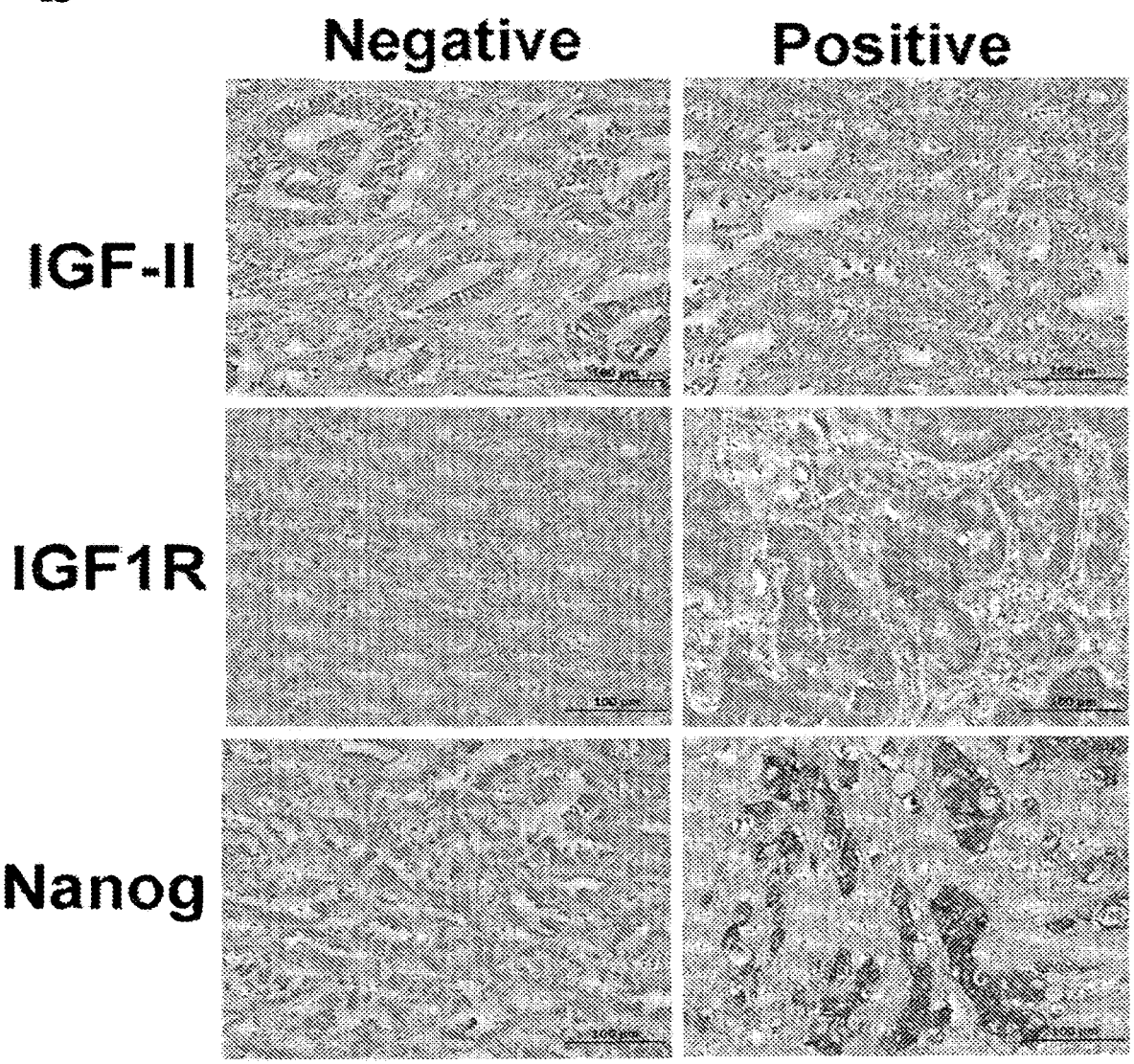
Figure 7:
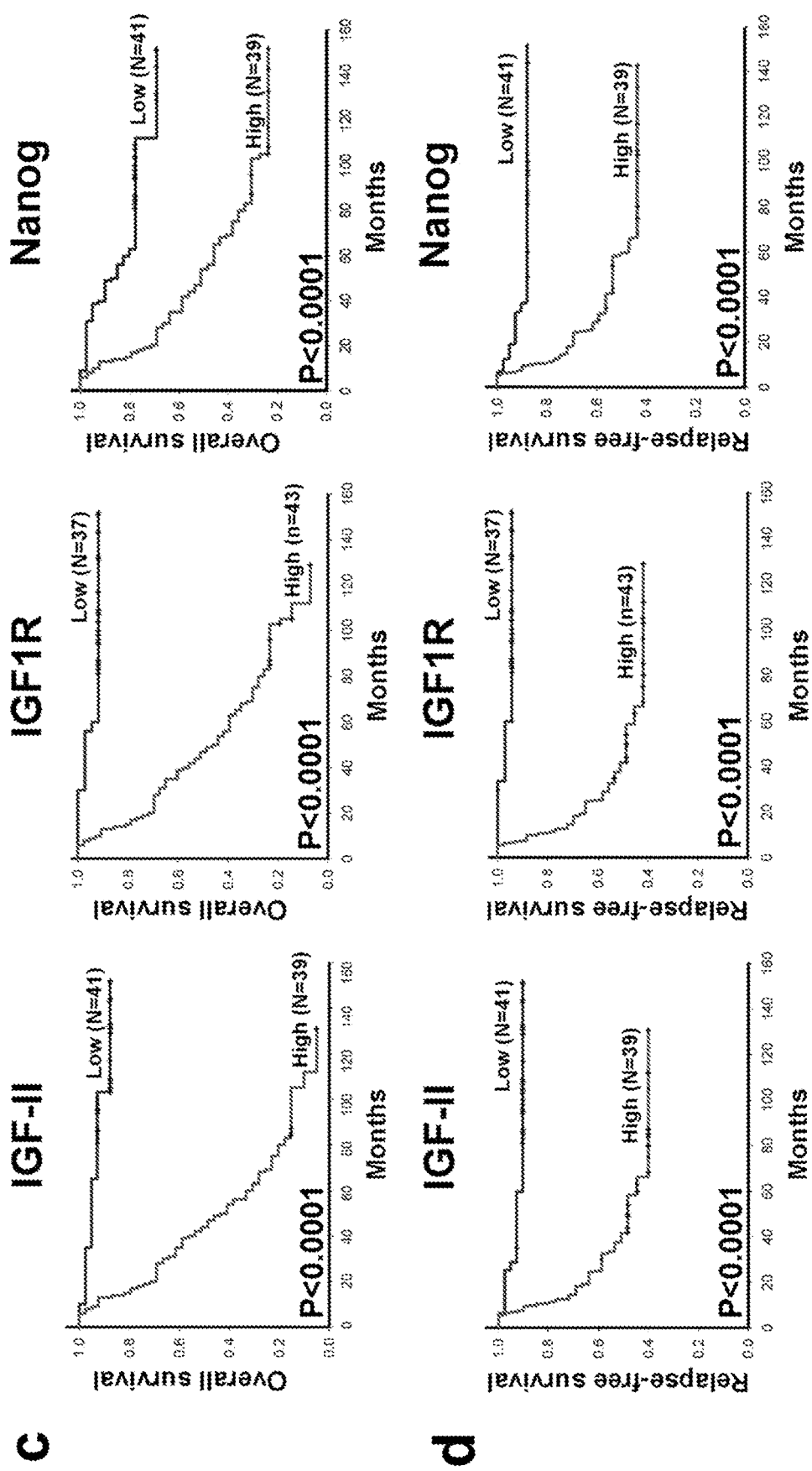
Figure 7:
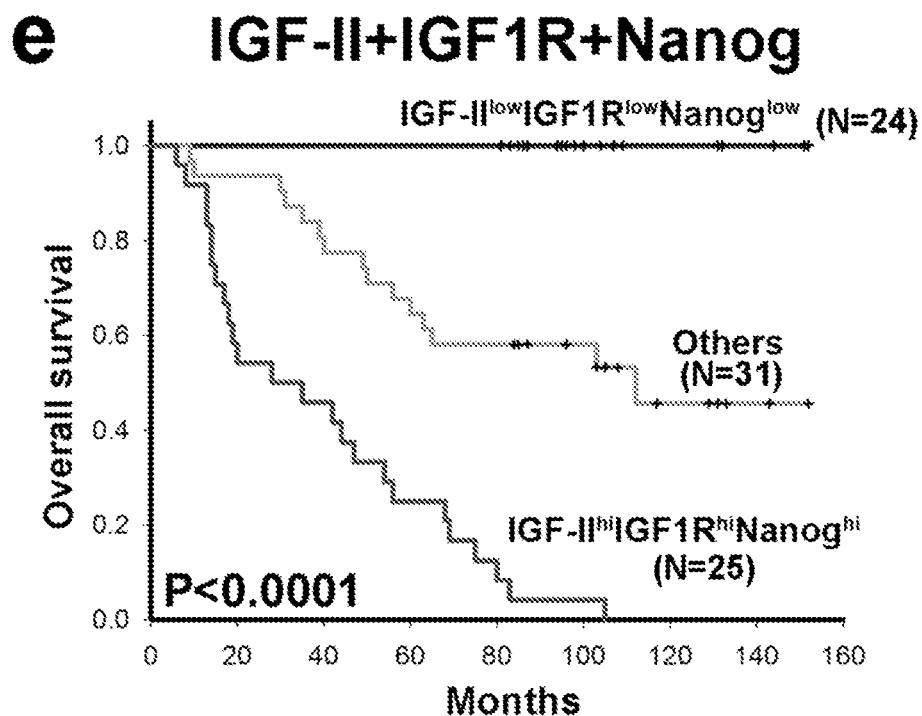
Figure 7:
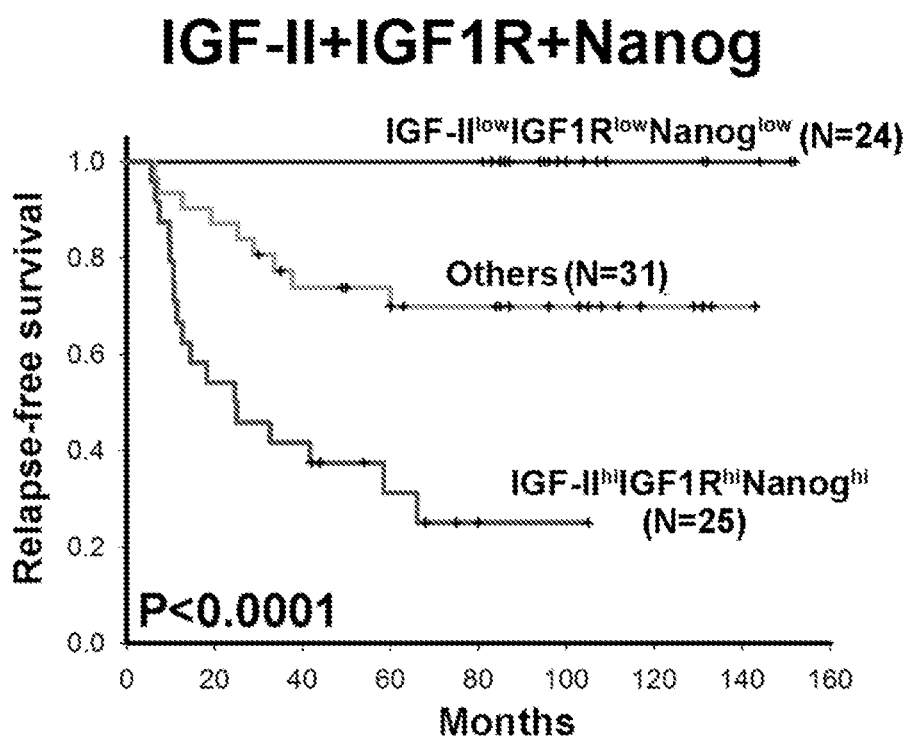

A tree diagram was created to display the conditional probabilities of IGF-II, IGF1R and Nanog expression, as shown in FIG. 7a. These results indicated that 72% of patients with high IGF-II and high IGF1R expression levels also demonstrated high Nanog expression levels, whereas 80.6% of patients with low expression levels of IGF-II and IGF1R demonstrated lower Nanog expression levels. Next, serial sections of each specimen were stained with antibodies against IGF-II in CAFs and against IGF1R and Nanog in tumor cells, as shown in FIG. 7b. These results indicated that patients with high-level of IGF-II in CAFs and IGF1R or Nanog in tumor cells demonstrated significantly poorer overall survival (P<0.0001, Kaplan-Meier analysis; FIG. 7c) and relapse-free survival (P<0.0001, Kaplan-Meier analysis; FIG. 7d) compared to patients with low-level expression.

Multivariable Cox proportional hazards regression analyses were used to evaluate the 9 associations of various independent prognostic factors with patient survival (Table 9).

TABLE 9

Multivariate Cox Proportional Hazards Regression Analysis with Covariates Age, Gender, Cell type, Tumor Size, Proliferative marker and Tumor grade for Overall survival of Cancer Stem Cell Markers

| | Hazard ratio | 95% HR C.I. | | p-value* |
|---|---|---|---|---|
| IGF-II | | | | |
| IGF-II | 19.15 | 6.32 | 58.00 | <0.0001 |
| Age | 0.99 | 0.96 | 1.03 | 0.623 |
| Gender | 1.60 | 0.75 | 3.41 | 0.221 |
| Cell type† | 0.48 | 0.21 | 1.11 | 0.086 |
| Tumor size | 1.09 | 0.94 | 1.26 | 0.250 |
| Proliferative marker | 1.27 | 0.64 | 2.52 | 0.491 |
| Tumor grade | 0.60 | 0.24 | 1.50 | 0.273 |
| IGF1R | | | | |
| IGF1R | 15.80 | 5.85 | 65.96 | <0.0001 |
| Age | 1.00 | 0.96 | 1.03 | 0.613 |
| Gender | 1.56 | 0.64 | 2.48 | 0.499 |
| Cell type† | 0.57 | 0.28 | 1.36 | 0.230 |

TABLE 9-continued

Multivariate Cox Proportional Hazards Regression Analysis with Covariates Age, Gender, Cell type, Tumor Size, Proliferative marker and Tumor grade for Overall survival of Cancer Stem Cell Markers

| | Hazard ratio | 95% HR C.I. | | p-value* |
|---|---|---|---|---|
| Size | 1.06 | 0.91 | 1.21 | 0.515 |
| Proliferative marker | 1.51 | 0.76 | 3.00 | 0.238 |
| Tumor grade | 0.56 | 0.23 | 1.35 | 0.198 |
| Nanog | | | | |
| Nanog | 4.84 | 2.17 | 10.80 | 0.0001 |
| Age | 1.00 | 0.97 | 1.03 | 0.806 |
| Gender | 2.51 | 1.25 | 5.05 | 0.010 |
| Cell type† | 0.94 | 0.41 | 2.14 | 0.876 |
| Size | 1.22 | 1.04 | 1.43 | 0.016 |
| Proliferative marker | 1.70 | 0.86 | 3.37 | 0.130 |
| Tumor grade | 0.57 | 0.23 | 1.37 | 0.207 |
| Combination of IGF-II and IGF1R | | | | |
| IGF-II and IGF1R | 15.92 | 6.25 | 40.54 | <0.0001 |
| Age | 1.00 | 0.97 | 1.03 | 0.867 |
| Gender | 1.88 | 0.87 | 4.06 | 0.107 |
| Cell type† | 0.46 | 0.18 | 0.99 | 0.047 |

TABLE 9-continued

Multivariate Cox Proportional Hazards Regression Analysis with Covariates Age, Gender, Cell type, Tumor Size, Proliferative marker and Tumor grade for Overall survival of Cancer Stem Cell Markers

|  | Hazard ratio | 95% HR C.I. |  | p-value* |
|---|---|---|---|---|
| Size | 1.04 | 0.90 | 1.21 | 0.605 |
| Proliferative marker | 1.23 | 0.60 | 2.51 | 0.577 |
| Tumor grade | 0.60 | 0.25 | 1.44 | 0.256 |
| Combination of IGF-II, IGF1R, and Nanog | | | | |
| IGF-II, IGF1R, and Nanog | 8.37 | 3.84 | 18.26 | <0.0001 |
| Age | 1.00 | 0.97 | 1.03 | 0.913 |
| Gender | 1.66 | 0.82 | 3.35 | 0.159 |
| Cell type† | 0.65 | 0.29 | 1.45 | 0.288 |
| Size | 1.24 | 1.05 | 1.46 | 0.010 |
| Proliferative marker | 1.56 | 0.79 | 3.11 | 0.204 |
| Tumor grade | 0.81 | 0.32 | 2.07 | 0.659 |

The results revealed that the independent prognostic factors included IGF-II expression (hazard ratio (HR)=19.15, 95% CI=6.32 to 58.00; P<0.0001, Cox proportional hazards regression analysis), IGF1R expression (HR=15.80, 95% CI=5.85 to 65.96; P<0.0001, Cox proportional hazards regression analysis) and Nanog expression (HR=4.84, 95% CI=2.17 to 10.80; P=0.0001, Cox proportional hazards regression analysis). The independent prognostic factors associated with metastasis were IGF-II expression (HR=7.37, 95% CI=2.43 to 22.35; P=0.0004, Cox proportional hazards regression analysis), IGF1R expression (HR=13.29, 95% CI=3.09 to 57.23; P=0.0005, proportional hazards regression analysis) and Nanog expression (HR=7.59, 95% CI=2.67 to 21.62; P=0.0001, Cox proportional hazards regression analysis. Table 10.

TABLE 10

Multivariate Cox Proportional Hazards Regression Analysis with Covariates Age, Gender, Cell type, Tumor Size, Proliferative marker and Tumor grade for Relapse free survival of Cancer Stem Cell Markers

|  | Hazard ratio | 95% HR C.I. |  | p-value |
|---|---|---|---|---|
| IGF-II | 7.37 | 2.43 | 22.35 | 0.0004 |
| Age | 1.01 | 0.97 | 1.06 | 0.543 |
| Gender | 2.78 | 1.14 | 6.75 | 0.024 |
| Cell type | 1.47 | 0.49 | 4.41 | 0.494 |
| Size | 0.95 | 0.77 | 1.17 | 0.612 |
| Proliferative marker | 1.21 | 0.52 | 2.81 | 0.653 |
| Tumor grade | 0.54 | 0.19 | 1.50 | 0.235 |
| IGF1R | 13.29 | 3.09 | 57.23 | 0.0005 |
| Age | 1.02 | 0.98 | 1.07 | 0.3393 |
| Gender | 2.70 | 1.10 | 6.60 | 0.023 |
| Cell type | 1.34 | 0.44 | 4.10 | 0.607 |
| Size | 0.94 | 0.75 | 1.17 | 0.555 |
| Proliferative marker | 1.43 | 0.63 | 3.28 | 0.396 |
| Tumor grade | 0.51 | 0.19 | 1.39 | 0.189 |
| Nanog | 7.59 | 2.67 | 21.62 | 0.0001 |
| Age | 1.03 | 0.98 | 1.07 | 0.263 |
| Gender | 3.98 | 1.62 | 9.77 | 0.003 |
| Cell type | 2.14 | 0.68 | 6.73 | 0.191 |
| Size | 1.04 | 0.80 | 1.36 | 0.749 |
| Proliferative marker | 1.30 | 0.56 | 3.04 | 0.539 |
| Tumor grade | 0.63 | 0.22 | 1.76 | 0.373 |
| IGF-II + IGF1R | 4.83 | 2.24 | 10.39 | <0.0001 |
| Age | 1.02 | 0.98 | 1.07 | 0.382 |
| Gender | 2.86 | 1.14 | 7.16 | 0.025 |
| Cell type | 1.35 | 0.43 | 4.22 | 0.605 |
| Size | 0.92 | 0.75 | 1.14 | 0.431 |
| Proliferative marker | 1.09 | 0.47 | 2.55 | 0.845 |
| Tumor grade | 0.56 | 0.20 | 1.53 | 0.258 |
| IGF-II + IGF1R + Nanog | 5.02 | 2.41 | 10.47 | <0.0001 |
| Age | 1.02 | 0.97 | 1.06 | 0.488 |
| Gender | 2.80 | 1.14 | 6.84 | 0.024 |
| Cell type | 1.69 | 0.55 | 5.20 | 0.363 |
| Size | 1.00 | 0.78 | 1.27 | 0.972 |
| Proliferative marker | 1.19 | 0.51 | 2.76 | 0.692 |
| Tumor grade | 0.91 | 0.32 | 2.66 | 0.869 |

Analysis of the combined effect of both the ligand and receptor on patient prognoses revealed that patients with high-level expression of IGF-II in CAFs and high-level expression of IGF1R and Nanog in tumor cells demonstrated the worst overall (IGF-II+IGF1R+Nanog, P<0.0001, Kaplan-Meier analysis; FIG. 7e; HR=8.37, 95% CI=33.84 to 18.26; P<0.0001, Cox proportional hazards regression analysis; Table 1,) and relapse-free survival (IGF-II+IGF1R+Nanog, P<0.0001, Kaplan-Meier analysis; FIG. 7e; HR=5.02, 95% CI=2.41 to 10.47; P<0.0001, Cox proportional hazards regression analysis; Supplementary Table 7) compared to those with low-level expression of IGF-II in CAFs and low-level expression of IGF1R and Nanog in tumor cells. These results further demonstrate that IGF-II, IGF1R and Nanog paracrine signaling may provide a novel prognostic index for predicting metastasis (P<0.0001, Cox proportional hazards regression analysis) and overall survival (P<0.0001, Cox proportional hazards regression analysis) in early stage NSCLC patients (Table 9 and Table 10).

DISCUSSION

One key factor that hinders CSC research is the lack of a powerful culture system to support CSC growth while preserving stemness. Moreover, traditional embryonic stem cell culture systems that use fibroblasts as feeder cells have not yet successfully translated into a working model for CSC research. Here, a primary cultures of lung CSCs from lung cancer patients was established for use in studying CSC properties and in identifying cancer drugs targeting CSCs. Importantly, lung CSCs could be sub-cultured while maintaining the characteristics of cancer stemness using CAFs as feeder cells.

Figure 8:
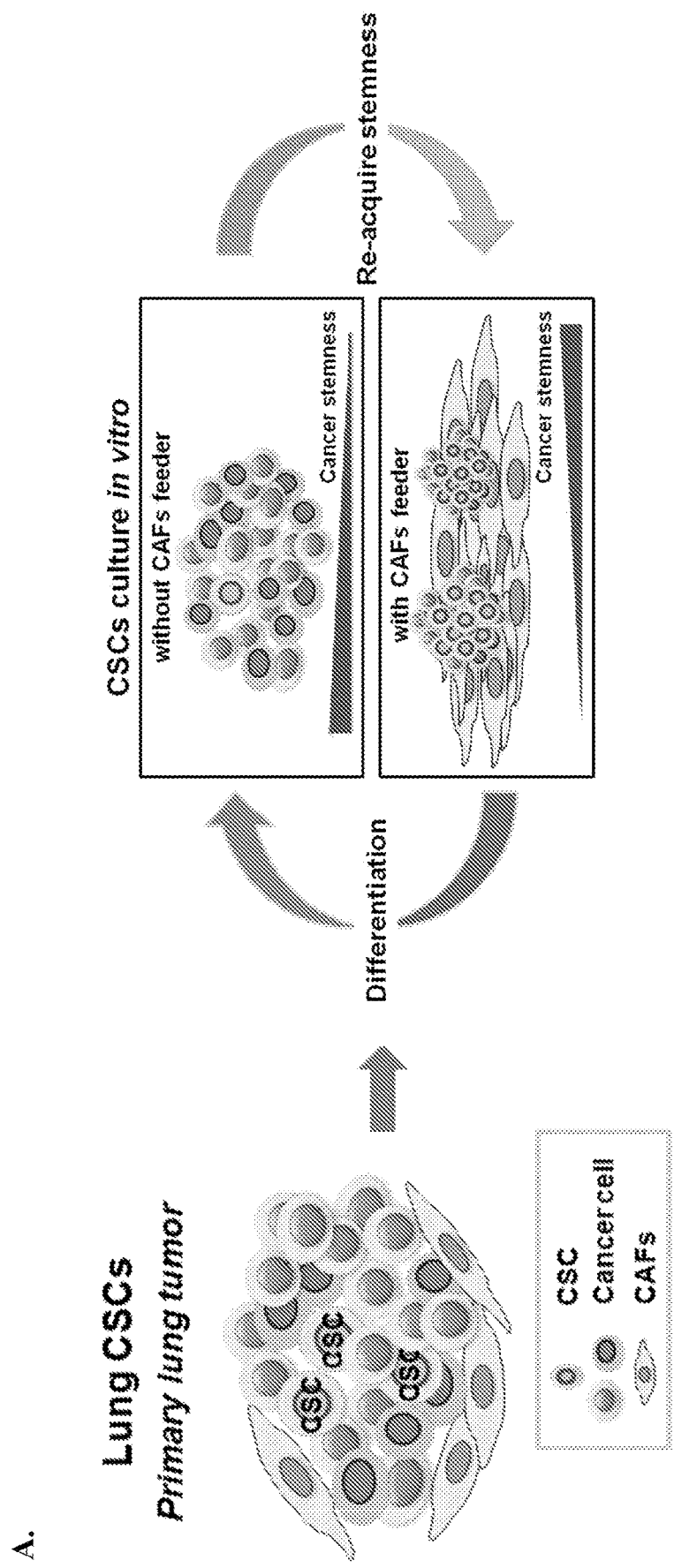
FIG. 8 is a schematic illustration of the crosstalk between CAFs and lung CSCs. A and B: CAFs secrete IGF-II, which activates IGF1R/Nanog in lung CSCs through IGF1R signaling and Akt phosphorylation. Upon triggering the paracrine IGF-II/IGF1R pathway, other autocrine (LIF and LIFR; TGF-β and TGFBR1; WNT and Frizzled receptor) and paracrine (HGF and HGFR/c-MET; SDF-1 and CXCR4) signaling between CAFs and CSCs may contribute synergistically to the maintenance of lung CSC stemness.
Figure 8:
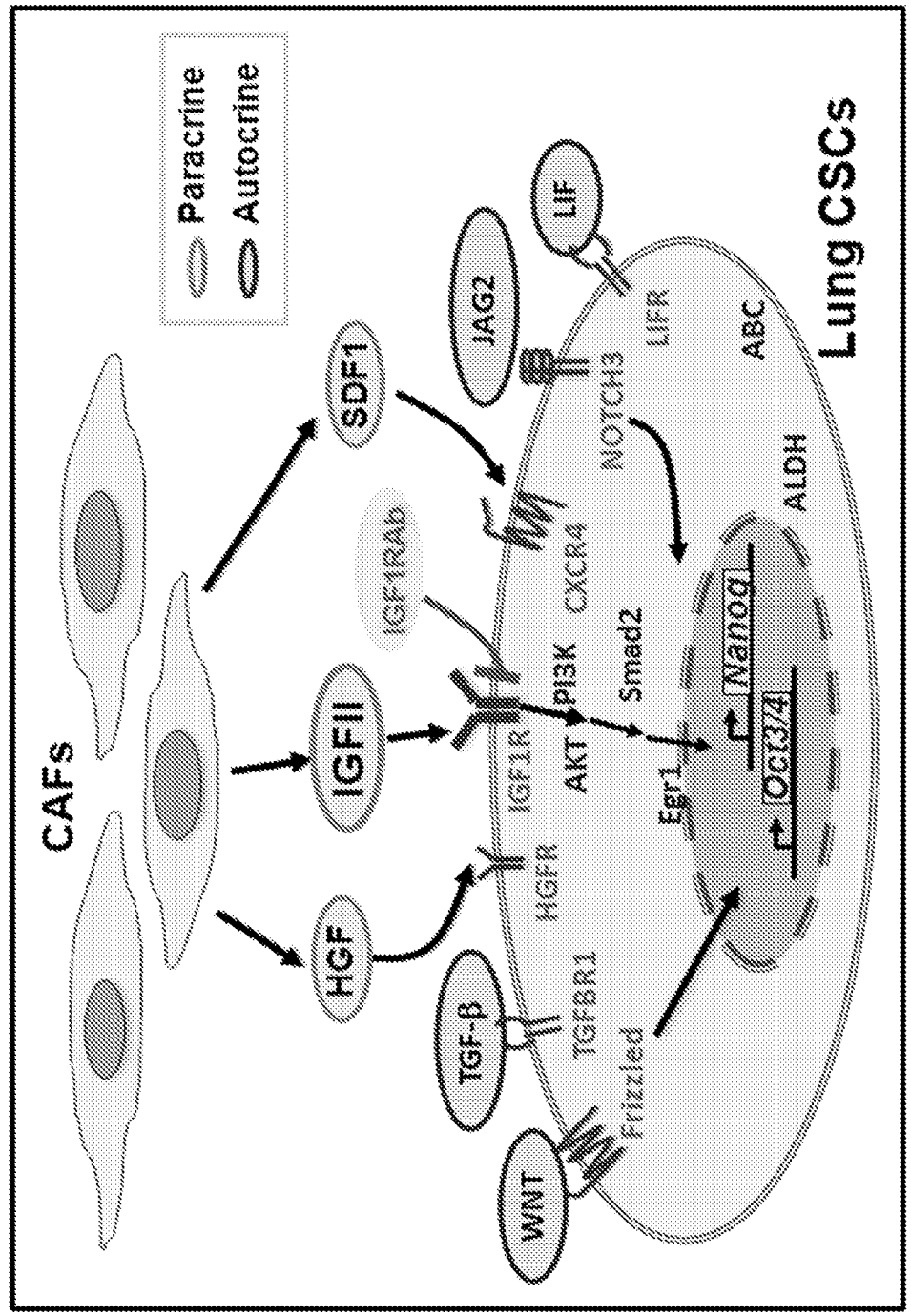

In this study, it was demonstrated that CAFs (but not NFs) supported CSC growth. These CSCs isolated from primary cultures of lung tumors and cancer cell lines maintained their ability to express stemness markers and generate tumors in mouse xenografts at low cell numbers (<100 cells), and CAFs were essential for maintaining this stemness phenotype. Without the support of CAF feeder cells, lung CSCs differentiated into cancer cells. Interestingly, the addition of CAFs as niche cells could facilitate the conversion of differentiated tumor cells to CSC state through paracrine activation of EMT/MET, WNT, Notch, Hedgehog signaling. Giannoni, et al. *Cancer Res* 70, 6945-6956; 2010. Most importantly, It was found that CAFs regulate CSC growth in a paracrine fashion by overexpression of growth factors such as IGF-II, HGF and SDF1 and by inducing expression of the corresponding receptors in CSCs, including IGF1R, IGF2R, HGFR and CXCR4. Moreover, the CAFs secreted IGF-II to stimulate the IGF1R on CSCs and thus activate the IGF-II/IGF1R/Nanog signaling pathway, which maintained lung cancer stemness in vitro and in vivo. In summary, the data obtained from this study support the CSC model and suggest the presence of autocrine regulation (Richards et al., *Nat Biotechnol* 20, 933-936; 2002); however, there were paracrine interactions between CAFs and CSCs that were crucial for maintaining the cancer stemness niche of lung CSCs (FIG. 8).

Importantly, using CAF-feeder cells, the CSCs could be sub-cultured while retaining their cancer stemness characteristics. The present study compared CAFs to paired NFs from different patients, and was found that CAFs, but not NFs, stimulated the sphere-forming ability of CSCs and led to the expression of stemness markers in lung cancer cell lines, indicating that CAFs supported CSC growth in vitro. Previously described strategies for isolating CSCs include sorting CSCs from the tumor bulk using specific markers or via forming mamospheres on ultra-low adherent plates. See, e.g., Fuchs, et al., *Cell* 116, 769-778 (2004); and Sneddon, et al., *Cell Stem Cell* 1, 607-611 (2007). However, these methods do not allow for the maintenance or sub-culturing of CSCs in vitro. It was established in the present disclosure that using CAFs as feeder cells, CSCs could be sub-cultured while retaining their cancer stemness, and this concept is similar to the ability of mouse embryonic fibroblasts (MEFs) to maintain the stemness of human embryonic stem (hES) cells. Thomson, et al., *Science* 282, 1145-1147 (1998); and Richards et al., 2002. Based on this concept, a new model for culturing lung CSCs involving the use CAFs obtained from cancer patients as feeder cells was suggested herein to overcome the current difficulty of maintaining cancer stemness in vitro. This method supports long-term lung CSC growth and sub-culturing while maintaining the cancer stemness phenotype, and this platform should prove useful for drug screening and development of novel therapeutic strategies targeting CSCs or the stemness niche.

Previous studies have revealed the types of cells involved in the tumor microenvironment, including infiltrating immune cells (e.g., tumor-associated macrophages), and CAFs are crucial for driving the hallmarks of cancer, including tumorigenesis, angiogenesis and metastasis. Doedens, et al. *Cancer Res* 70, 7465-7475 (2010); and Xu, et al., *Cell Biol Int* 35, 509-517 (2011). However, it remains less well understood how the tumor microenvironment supports cancer stemness[52,53]. Xu et al., 2011; and Hanahan, et al., *Cancer Cell* 21, 309-322 (2012). ES cell research has shown that feeder cells are essential for supporting stem cell growth and the inhibition of differentiation through the secretion of certain factors (e.g., TGF-β1, LIF and bFGF) that activate important signaling (WNT, Notch, Hedgehog and EMT signaling). Mannello, et al., *Stem Cells* 25, 1603-1609 (2007). The present data demonstrated that CAFs (HGF, IGF-II, SDF-1, bFGF, WNT and oncostatin M) regulate CSC-like characteristics in a paracrine manner through the counterpart receptor/signaling components (EMT, TGF-β, WNT, Notch and Hedgehog) and stemness factors (Oct3/4, Sox2 and Nanog) in lung CSCs. Moreover, the present data confirmed the importance of the IGF-II/IGF1R/Nanog pathway in regulating lung CSC growth, predominantly in a paracrine manner in the tumor microenvironment, and in supporting lung cancer stemness. Through the interaction between lung CSCs and CAFs, lung CSCs could stimulate CAFs to produce IGF-II, which is important for triggering IGF1R signaling in CSCs.

Further, the two-way paracrine communication between CSCs and CAFs and its role in promoting cancer stemness were investigated, and the results indicated that CAFs secreted IGF-II, HGF and SDF-1. These factors may play important roles in maintaining cancer stemness and were up-regulated following co-culture with CSCs or cancer cells. The present data suggest that cytokines, including bFGF, HGF, IGFBP2, GM-CSF and PARC, which were abundant in CSC conditioned medium, may be released by CAFs after the induction of IGF-II expression. Additional evidence from previous studies indicates that bFGF and TGF-β released from cancer cells may be involved in fibroblast activation. Kalluri, et al., *Nat Rev Cancer* 6, 392-401 (2006); and Franco, et al., *Cancer Res* 71, 1272-1281 (2011). The results provided herein indicate that the cancer stemness niche may share similar paracrine loops as those regulating hES cells. Bendall, et al., *Nature* 448, 1015-1021 (2007).

Furthermore, the present data revealed two-way communication between cancer cells and CAFs. The regulation of CAFs in terms of IGF-II secretion could be up-regulated by lung cancer cells or CSCs through bFGF and other cytokines, whereas the IGF-II/IGF1R axis promoted Nanog expression in cancer cells. A positive feedback loop may therefore exist, leading to increased IGF1R expression in CSCs and maintenance of CSC stemness. Shan et al., 2012. This evidence supports the role of cancer-stroma interactions and the importance of the tumor microenvironment in regulating cancer stemness. The present data further indicated that blockade of IGF-II/IGF1R/Akt/Nanog signaling could reduce cancer stemness in CSCs, suggesting the potential clinical application of targeted therapy using an IGF1R inhibitor for lung CSCs.

Recently, many new therapeutic strategies have been designed to target and eliminate CSCs; however, the tumor microenvironment has been suggested to play a dominant role in determining the malignant characteristics of CSCs. Vermeulen, et al., *Lancet Oncol* 13, e83-89 (2012). It is particularly important to determine whether the "de-differentiation" of non-tumorigenic cancer cells towards CSCs can occur in certain niches. Previous studies have suggested that cell plasticity and de-differentiation in normal somatic cells could be controlled by environmental factors or artificial transduction with the right factors. Bjornson, et al., *Science* 283, 534-537 (1999); and Takahashi, et al., *Cell* 131, 861-872 (2007). Recently, tumor microenvironment stromal cells have been shown to induce the de-differentiation of intestinal epithelial cells that acquire tumor-initiating capacity during intestinal tumorigenesis. Schwitalla, et al., *Cell* 152, 25-38 (2013). In this study, it was found that differentiated cancer cells (CLS1 p12, CLS1 p27 and A549 cells) and the non-cancerous stem cell population (ALDH– CLS1 cells) might be possibly de-differentiated through co-culture with CAFs to regain CSC-like properties and re-expression of stemness markers (Nanog and Oct3/4). The present finding provides evidence that de-differentiation of differentiated cancer cells may occur under the influence of the tumor microenvironment, i.e., CAFs.

Furthermore, this study examined if IGF-II/IGF1R paracrine and stemness marker Nanog could serve as novel prognostic markers in stage I NSCLC patients. Previously, most prognostic factor studies focused on cancer cells rather than on CAFs; only an 11-gene prognostic CAF signature has been reported to be associated with NSCLC patient survival. Navab et al., 2011. However, the clinical impact of paracrine regulation between CAFs and CSCs has not been well studied. For the first time, an IHC staining was performed to clearly distinguish the levels of IGF-II in CAFs and IGF1R/Nanog in cancer cells as important prognostic markers for early stage lung cancer patients. In fact, the IGF-II levels in CAFs individually or in combination with the IGF1R and Nanog levels in cancer cells strongly correlated with the overall and relapse-free survivals. It was concluded that IGF-II/IGF1R/Nanog paracrine signaling on tumor progression could serve as a prognostic marker for early stage lung cancer.

In conclusion, this study provides new insights into the crosstalk between the tumor microenvironment and CSCs. The CLS1/CAF co-culture model represents a new platform for anticancer drug screening to derive compounds targeting CSCs and tumor-associated stromal cells. Moreover, the finding that CAFs regulate CSCs in a paracrine fashion through the IGF-II/IGF1R/Nanog pathway provides new potential targets for anticancer therapy.

Example 2: Image-Based High-Content Assay

Lung CSCs or cancer cells (200 cells/well) were added to 96-well plates pre-seeded with CAFs (2000 cells/well) and were allowed to attach to the plates overnight. After different treatments, cells were processed following the immunofluorescence protocol with the Nanog (ReproCELL) (1:300) primary antibody (as the cancer stem-cell marker) and the mouse anti-human CD90 FITC-conjugated (5E10, BD Pharmingen) antibody (as the CAF marker) overnight at 4° C. Next, the primary antibodies were incubated with the TRITC-conjugated secondary antibody [goat anti-rabbit IgG (H+L) Conjugate, Invitrogen] for 2 h at room temperature. The nuclei were counterstained with the Hoechst 33342 dye (Invitrogen). To determine the background fluorescence level of the secondary antibody, each plate included control wells containing only the secondary antibody (stained with the Hoechst 33342 dye). Images of the stained cells were acquired using the automated fluorescence microscopy platform.

Image acquisition and analysis were performed as follows. Stained cells were imaged using the high-content analysis platform with a 4× objective. Twelve fields per well for each wavelength were captured and montaged for further image analysis. The images were analyzed using the MetaXpress® software (Molecular Devices). First, the cancer cell nuclei (cells without FITC staining, CD90−) were identified using Multi-Wavelength Cell Scoring. The segmented cancer cell nuclei were dilated and smoothed using Morphology Filters to create a cell cluster mask. Cell clusters greater than 10000 $\mu m^2$ were defined as cancer cell colonies. Finally, the TRITC-stained cell count and the total cell count were determined. The stemness of each colony was calculated as the ratio of Nanog-positive (TRITC-stained) cells to total cells. The colony density was defined as the total cell count divided by the colony area.

An illustrative diagram showing the process of an exemplary image-based high content assay is provided in FIG. 14a.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for identifying an anti-cancer drug, comprising:

providing an in vitro co-culture system comprising cancer associated fibroblasts (CAFs), a population of cancer cells, and a drug candidate; wherein the CAFs are CD90+, wherein in the in vitro co-culture system, the ratio between the cancer cells and the CAFs ranges from 1:100 to 1:10; and wherein the CAFs maintain or induce stemness of the cancer cells in the co-culture system;

determining the level of cancer cell stemness in the co-culture, and identifying the drug candidate as an anti-cancer drug, if the level of cancer cell stemness in the co-culture is decreased as compared to that of a co-culture of cancer cells and CAFs of the same type as those in the in vitro co-culture system in the absence of the drug candidate.

2. The method of claim 1, wherein the population of cancer cells in the in vitro co-culture, system are from an established cancer cell line, or wherein the cancer cells are primary cancer cells obtained from a cancer patient.

3. The method of claim 1, wherein the population of cancer cells are lung cancer cells, breast cancer cells, kidney cancer cells, prostate cancer cells, ovary cancer cells, skin cancer cells, cervical cancer cells, colon cancer cells, liver cancer cells, melanoma cells, oral cancer cells, or pancreatic cancer cells.

4. The method of claim 1, wherein the CAFs in the in vitro co-culture system are obtained from a cancer patient.

5. The method of claim 1, wherein the level of cancer cell stemness is determined by:

measuring the level of Oct3/4$^+$ and Nanog$^+$ cells in the co-culture;

measuring the drug resistance of the cancer cells in the co-culture, measuring the level of one or more of IGF-II, HGF, LIF, and SDF1 expressed in the CAFs, the level of one or more of IGF1R, IGF2R, LIFR, CXCR4, and Nanog expressed in the cancer cells, or both, or measuring the ratio of cancer stem cells (CSCs) to total cells in a cancer cell colony formed in the co-culture.

6. The method of claim 1, wherein the determining step comprises:

(i) staining the in vitro co-culture system comprising the CAFs and the cancer cells with a first agent for detecting Nanog, wherein the first agent is conjugated with a first label directly or indirectly; and a second agent for detecting CD90, wherein the second agent is conjugated with a second label directly or indirectly, the second label being different from the first label;

(ii) imaging the CAFs and the cancer cells stained with the first and second agents; and (iii) determining stemness of the cancer cells in the in vitro co-culture system based on the signals released from the first and second labels.

7. The method of claim 1, wherein the population of cancer cells are non-small cell lung cancer cells.

8. The method of claim 7, wherein the CAFs are obtained from a non-small cell lung cancer patient.

9. The method of claim 6, wherein the first label, the second label, or both are fluorescent dyes.

10. The method of claim 6, further comprising staining the in vitro co-culture system with a third agent for detecting nuclei.

* * * * *

UNITED STATES PATENT AND TRADEMARK OFFICE
CERTIFICATE OF CORRECTION

| | | |
|---|---|---|
| PATENT NO. | : 10,865,388 B2 | Page 1 of 1 |
| APPLICATION NO. | : 15/513804 | |
| DATED | : December 15, 2020 | |
| INVENTOR(S) | : Yang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 204 days.

Signed and Sealed this
Twenty-fourth Day of January, 2023

Katherine Kelly Vidal
*Director of the United States Patent and Trademark Office*